United States Patent
Batra et al.

(10) Patent No.: US 10,005,753 B2
(45) Date of Patent: Jun. 26, 2018

(54) METHODS FOR PRODUCING BERAPROST AND ITS DERIVATIVES

(71) Applicant: Lung Biotechnology PBC, Silver Spring, MD (US)

(72) Inventors: Hitesh Batra, Herndon, VA (US); Sudersan M. Tuladhar, Silver Spring, MD (US); Sri Harsha Tummala, Owings Mills, MD (US); Raju Penmasta, Herndon, VA (US); David A. Walsh, Spotsylvania, VA (US)

(73) Assignee: Lung Biotechnology PBC, Silver Spring, MD (US)

( * ) Notice: Subject to any disclaimer, the term of this patent is extended or adjusted under 35 U.S.C. 154(b) by 0 days. days.

(21) Appl. No.: 15/312,295

(22) PCT Filed: May 19, 2015

(86) PCT No.: PCT/US2015/031616
§ 371 (c)(1),
(2) Date: Feb. 2, 2017

(87) PCT Pub. No.: WO2015/179427
PCT Pub. Date: Nov. 26, 2015

(65) Prior Publication Data
US 2017/0166545 A1  Jun. 15, 2017

Related U.S. Application Data

(60) Provisional application No. 62/000,800, filed on May 20, 2014, provisional application No. 62/006,360, filed on Jun. 2, 2014.

(51) Int. Cl.
*C07D 307/93* (2006.01)
*C07C 69/65* (2006.01)
*C07C 233/20* (2006.01)
*C07C 67/307* (2006.01)
*C07C 67/00* (2006.01)

(52) U.S. Cl.
CPC ............ *C07D 307/93* (2013.01); *C07C 67/00* (2013.01); *C07C 67/307* (2013.01); *C07C 69/65* (2013.01); *C07C 233/20* (2013.01); *C07C 2101/10* (2013.01)

(58) Field of Classification Search
CPC .................................................. C07D 307/93
USPC ................................................. 549/458, 214
See application file for complete search history.

(56) References Cited

U.S. PATENT DOCUMENTS

| 5,202,447 | A | 4/1993 | Ohno et al. |
| 7,345,181 | B2 | 3/2008 | Kim et al. |
| 9,388,154 | B2 * | 7/2016 | Yiannikouros ...... C07D 307/93 |
| 2004/0209945 | A1 | 10/2004 | Szabo et al. |
| 2005/0272943 | A1 | 12/2005 | Kim et al. |
| 2012/0323025 | A1 | 12/2012 | Sharma et al. |

FOREIGN PATENT DOCUMENTS

WO   WO 2013/040068 A2   3/2013

OTHER PUBLICATIONS

Greene, TW, et al., "Protecting Groups," 1991, 1-11.
Lucet et al., "First Synthesis of Both Enantiomers of the Biotin Vitamer 8-Amino-7-oxopelargonic Acid," Tetrahedron: Asymmetry, 1996, 7(4):985-988.
Myers et al., "Pseudoephedrine as a Practical Chiral Auxiliary for the Synthesis of Highly Enantiomerically Enriched Carboxylic Acids, Alcohols, Aldehydes, and Ketones," J. Am. Chem. Soc., 1997, 119:6496-6511.
Nagase et al,. "Synthesis of (+)-5,6,7-Trinor-4,8-Inter-$m$-Phenylene $PGI_2^{1)}$," Tetrahedron Letters, 1990, 31(31):4493-4494.
Lee et al., "Efficient Synthesis of Benzoprostacyclins Using Free-Radical and Palladium-Catalyzed Tandem Alkene Insertion Strategies," Bull. Korean Chem. Soc,., 2001, 22(8):857-866.
PubChem Substance Record for SID 77245144, create date: Jun. 12, 2009, 5 pages.
Larock et al., "Efficient Free-Radical and Palladium-Catalyzed Tandem Alkene Insertions: A New Approach to Benzoprostacyclins," J. Org. Chem., Oct. 1, 1991, 56:6253-6254.

* cited by examiner

*Primary Examiner* — Niloofar Rahmani
(74) *Attorney, Agent, or Firm* — Foley & Lardner LLP

(57) ABSTRACT

The present invention is directed to methods for preparing Beraprost and novel synthetic intermediates for Beraprost. In one aspect, a process is provided to produce a pharmaceutical compound represented by the general Formula (I) via a radical cyclization route. The process is completed in fewer steps than the known synthetic methods and may be conducted to prepare commercially useful quantities. In another aspect, synthetic methods are provided for producing Beraprost and its derivatives, which are stereoselective, efficient, scalable and economical. In another aspect, substantially isomerically pure compounds and intermediates are produced by the above processes.

13 Claims, No Drawings

METHODS FOR PRODUCING BERAPROST AND ITS DERIVATIVES

CROSS-REFERENCE TO RELATED PATENT APPLICATIONS

This application is the U.S. National Stage of PCT/US2015/031616, filed May 19, 2015, which claims priority from U.S. Provisional Application 62/000,800, filed May 20, 2014 and U.S. Provisional Application 62/006,360, filed Jun. 2, 2014, incorporated herein by reference in their entirety.

FIELD

The present technology generally relates to a process for synthesis of prostacyclin compounds and novel intermediate compounds useful in the process.

BACKGROUND OF THE INVENTION

Prostacyclin derivatives, including Treprostinil, Beraprost, Iloprost, and Epoprostenol, are useful pharmaceutical compounds possessing activities such as platelet aggregation inhibition, gastric secretion reduction, lesion inhibition, and bronchodilation. They are useful for preventing, controlling and treating a variety of diseases and pathological conditions.

Beraprost is a synthetic benzoprostacyclin analogue of natural prostacyclin that is currently under clinical trials for the treatment of pulmonary hypertension and vascular disease (excluding renal disease) in North America and Europe. Beraprost and its isomers have the following structure:

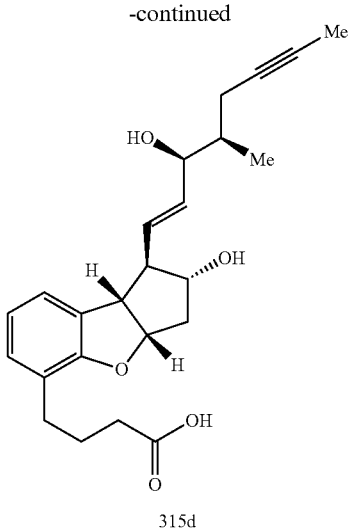

Beraprost (314d)

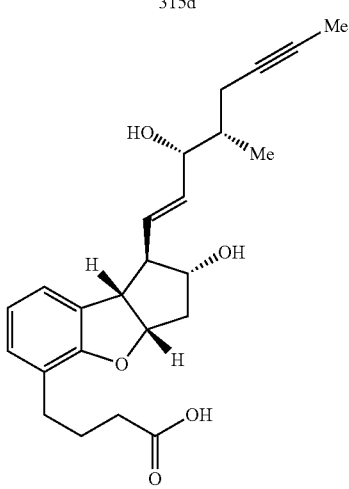

315d alpha hydroxy isomer

Beraprost and related benzoprostacyclin analogues are disclosed in U.S. Pat. No. 5,202,447 and Tetrahedron Lett. 31, 4493 (1990). Furthermore, as described in U.S. Pat. No. 7,345,181, several synthetic methods are known to produce benzoprostacyclin analogues. Methods of making Beraprost and related compounds are disclosed, for example, in US patent application publication no. 2012/0323025 and PCT publication WO2013/040068. The entire teaching of these documents are incorporated herein by reference in their entirety. The methods described in these patent documents however, do not describe a feasible production method for producing stereochemically pure Beraprost because, for example, the methods require the use of expensive reagents and tedious chromatographic purification techniques. Therefore, there is a need in the art for an economical, efficient and simplified method for preparing Beraprost and its synthetic intermediates, which can be scaled for commercial production.

SUMMARY OF THE INVENTION

In one aspect, a process is provided to produce a pharmaceutical compound represented by the general Formula (I) via a radical cyclization route. The process is completed in fewer steps than the known synthetic methods and may be conducted to prepare commercially useful quantities. In another aspect, synthetic methods are provided for producing Beraprost and its derivatives, which are stereoselective, efficient, scalable and economical. In another aspect, substantially isomerically pure compounds and intermediates are produced by the above processes. In addition, the present invention includes methods of treating pulmonary hypertension comprising administering the compounds to a subject in need thereof.

In various embodiments, provided is a method of preparing represented by the structural Formula (I):

(I)

and salts thereof.

In the process described below, unless mentioned otherwise, X is a halogen, preferably F, Cl, Br or I; $R^1$ is an alkyl, cycloalkyl or TBDMS; and $R^2$ is independently H, acetyl group or an alcohol protecting group. The process comprises:

(a) reacting a substituted halophenol with 6-oxabicyclo[3.1.0]hex-2-ene in the presence of a suitable catalyst, preferably a palladium catalyst, to form an ether compound represented by structural Formula (III):

(II)

(b) Acetylating the ether compound of Formula (III) to form a compound of Formula (IV)

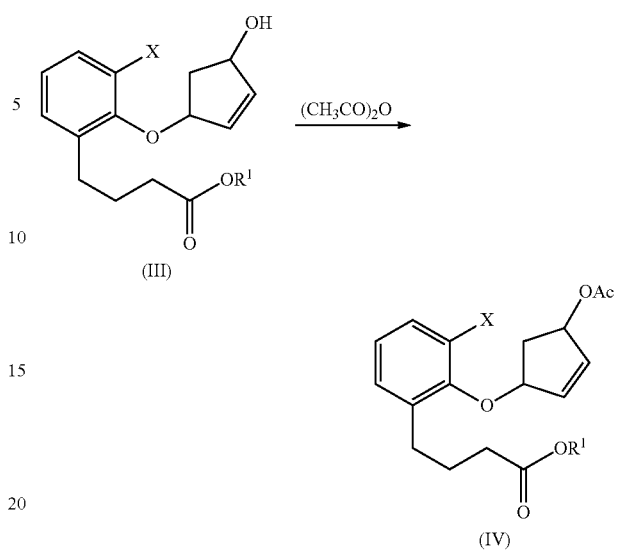

(c) Allylating the compound of Formula (IV), preferably with allyltributylstannane in the presence of AIBN, to form the allylation product (V)

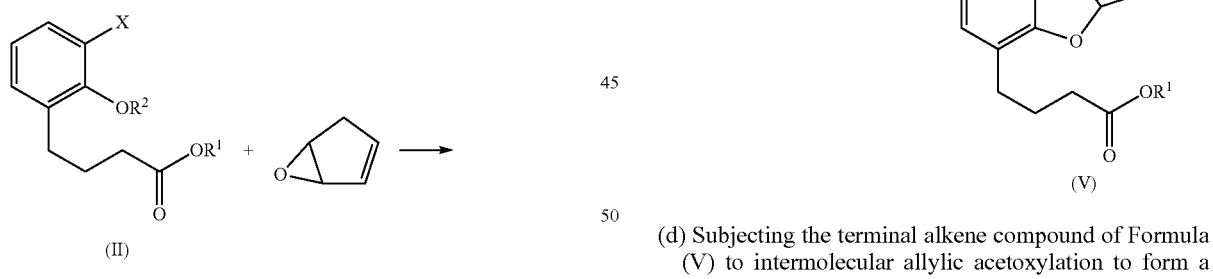

(d) Subjecting the terminal alkene compound of Formula (V) to intermolecular allylic acetoxylation to form a compound of Formula (VI)

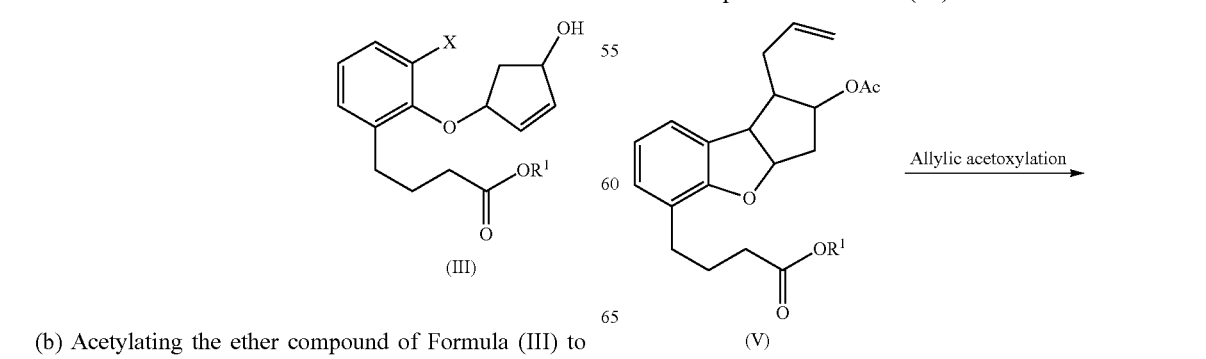

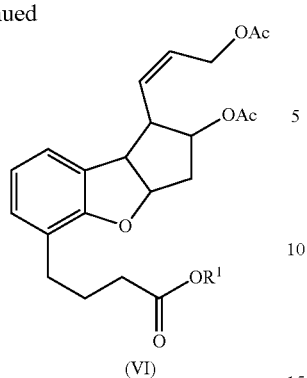

(VI)

(e) Subjecting the compound of Formula (VI) to dihydroxylation to form a compound of Formula (VII)

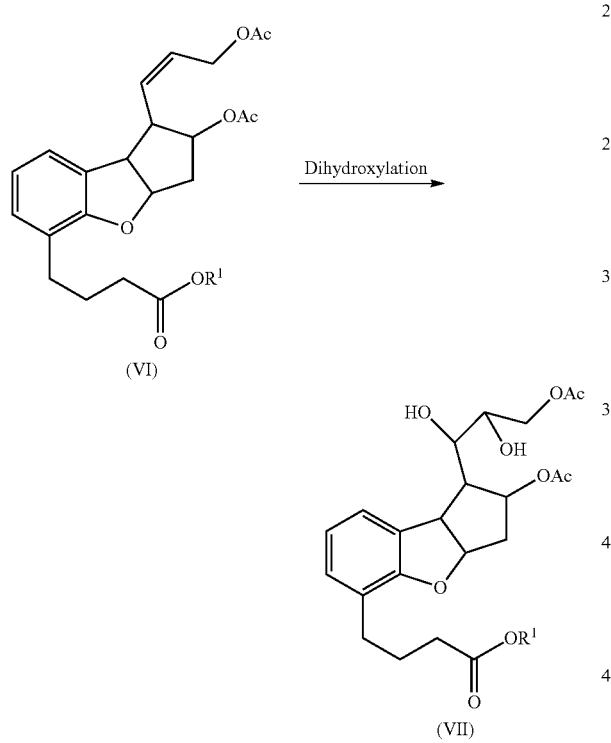

(f) Subjecting the dihydroxy compound (VII) to oxidation to form an aldehyde compound of Formula (VIII)

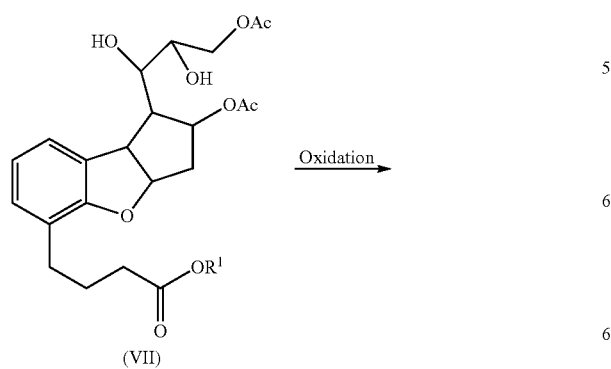

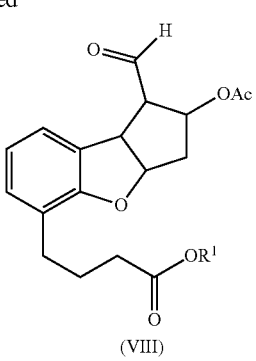

(VIII)

(g) Reducing the aldehyde compound of Formula (VIII) and removing the acetyl group to provide the diol compound of Formula (IX); and

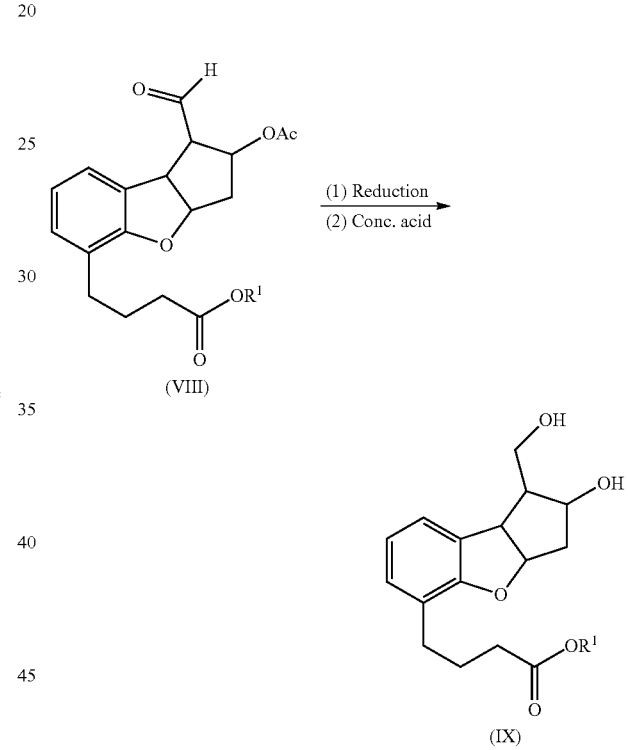

(h) Converting the diol of Formula (IX) to a protected aldehyde of Formula (VIIIA)

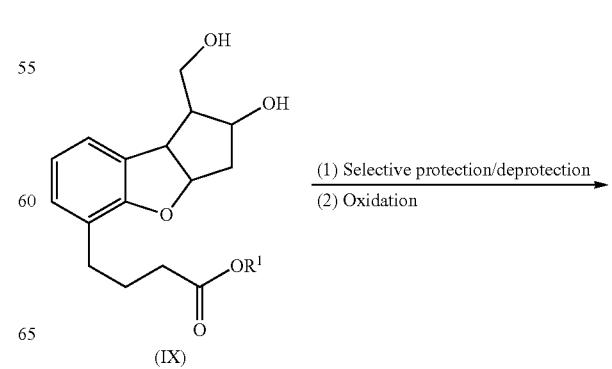

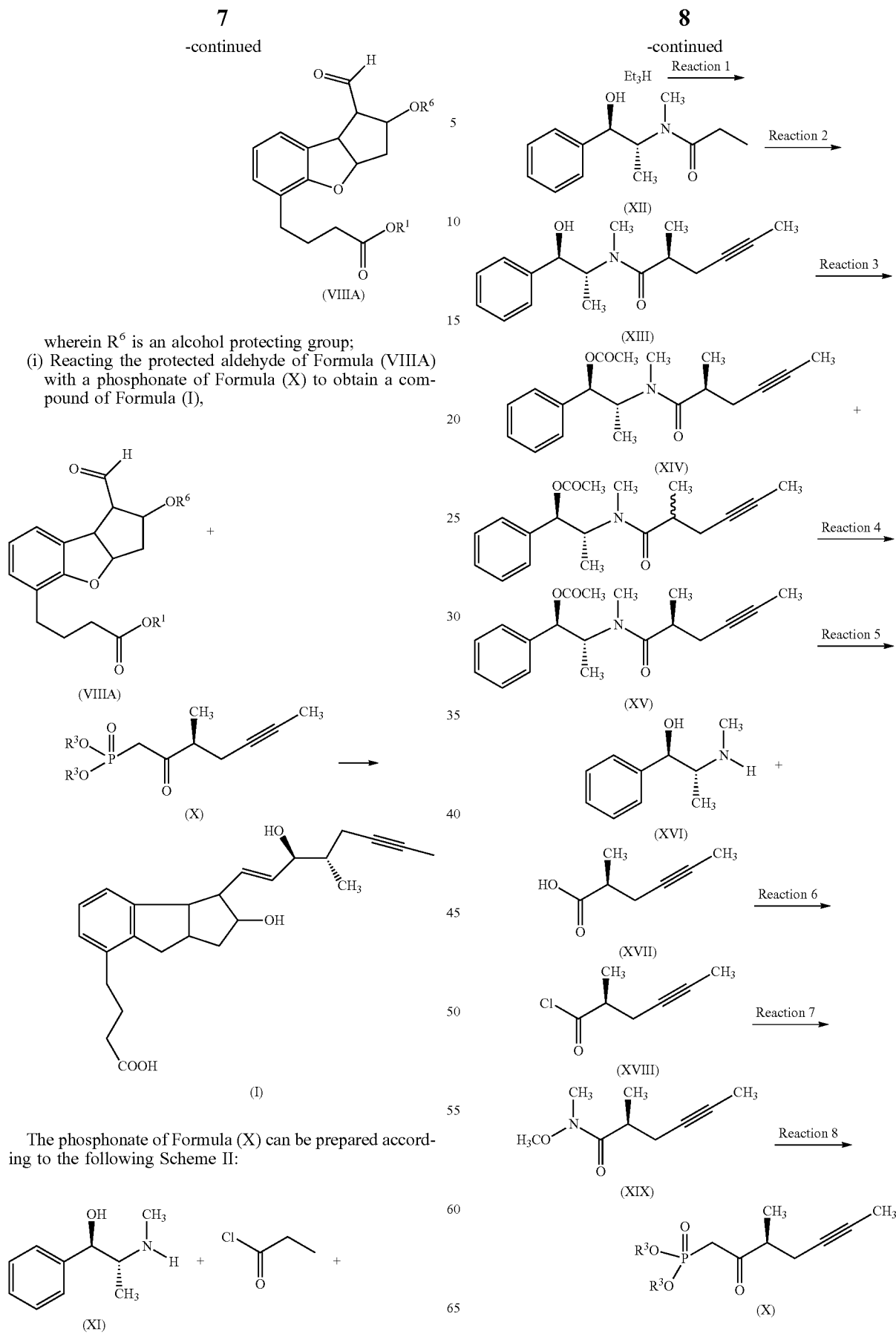
wherein $R^6$ is an alcohol protecting group;
(i) Reacting the protected aldehyde of Formula (VIIIA) with a phosphonate of Formula (X) to obtain a compound of Formula (I),
The phosphonate of Formula (X) can be prepared according to the following Scheme II:
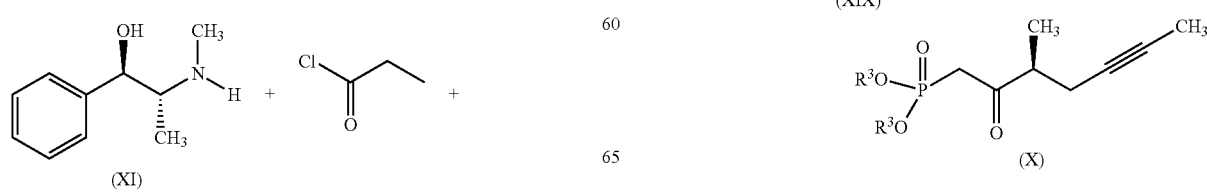

One embodiment of the invention relates to novel synthetic intermediates of Beraprost represented by the following structural Formula (XV) and methods of preparing them.

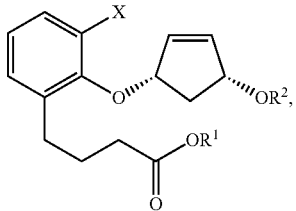

(XV)

wherein:
X is a halogen, preferably F, Cl or Br;
$R^1$ is alkyl, cycloalkyl or TBDMS; and
$R^2$ is independently H or an alcohol protecting group.

Another embodiment of the invention relates to novel synthetic intermediates of Beraprost represented by the following structural Formula (XVI) and methods of preparing them.

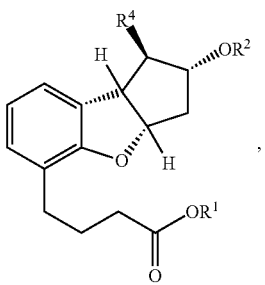

(XVI)

wherein:
$R^1$ is methyl or ethyl;
$R^2$ is independently H or an alcohol protecting group; and
$R^4$ is $CH(OH)CH_2OH$ or $CH=CH_2$.

Yet another embodiment of the invention relates to novel synthetic intermediates of Beraprost represented by the following structural Formula (XVII) and methods of preparing them.

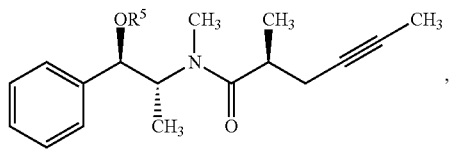

(XVII)

wherein $R^5$ is H or an acetyl group.

DETAILED DESCRIPTION OF THE EMBODIMENTS

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The expression "comprising" means "including, but not limited to." Thus, other non-mentioned substances, additives, carriers, or steps may be present. Unless otherwise specified, "a" or "an" means one or more.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_{m-n}$, such as $C_{1-12}$, $C_{1-8}$, or $C_{1-6}$ when used before a group refers to that group containing m to n carbon atoms.

The term "alkoxy" refers to —O-alkyl.

As used herein, "halo" or "halogen" or even "halide" can refer to fluoro, chloro, bromo, and iodo.

The term "alkyl" refers to monovalent saturated aliphatic hydrocarbyl groups having from 1 to 12 carbon atoms (i.e., $C_1$-$C_{12}$ alkyl) or 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—). An alkyl group is optionally substituted with halogen (e.g., —F, —Cl, —Br or —I), an alkoxy, a cycloalkyl (e.g., cyclopentyl or cyclohexyl), an aryl (e.g., phenyl), or heteroaryl group.

A phenyl group or a phenoxy group is optionally substituted with one or more (e.g., two, three, four or five) substituents independently selected from the group consisting of —$NO_2$, —CN, halogen (e.g., —F, —Cl, —Br or —I), (C1-C3)alkyl, halo(C1-C3)alkyl, (C1-C3)alkoxy and halo(C1-C3)alkoxy.

"Cycloalkyl" means a saturated aliphatic cyclic hydrocarbon radical optionally containing one or more double bonds. It can be monocyclic, bicyclic, polycyclic (e.g., tricyclic), fused, bridged, or spiro. For example, monocyclic ($C_3$-$C_6$) cycloalkyl means a radical having from 3-6 carbon atoms arranged in a monocyclic ring. A ($C_3$-$C_6$)cycloalkyl includes, but is not limited to, cyclopropyl, cyclobutyl, cyclopentyl and cyclohexyl. The cycloalkyl is optionally substituted with one or more (e.g., one, two, three, four or five) substituents independently selected from halogen (e.g., —F, —Cl, —Br or —I), an alkyl, an alkoxy, an aryl (e.g., phenyl), or a heteroaryl group.

"Alkoxy" means an alkyl radical attached through an oxygen linking atom, represented by —O-alkyl. For example, "(C1-C3) alkoxy" includes methoxy, ethoxy and propoxy.

"Haloalkyl" means an alkyl group substituted with one or more (e.g., two, three, four, five or six) halogen (—F, —Cl, —Br or —I).

"Heteroaryl" refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom.

Combinations of substituents and variables are only those that result in the formation of stable compounds. The term "stable," as used herein, refers to compounds which possess stability sufficient to allow manufacture and which maintains the integrity of the compound for a sufficient period of time to be useful for the purposes detailed herein.

As used herein, the term "prodrug" means a derivative of a compound that can hydrolyze, oxidize, or otherwise react under biological conditions (in vitro or in vivo) to provide an active compound. Examples of prodrugs include, but are not limited to, derivatives of a compound that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate).

As used herein, "hydrate" is a form of a compound wherein water molecules are combined in a certain ratio as an integral part of the structure complex of the compound.

As used herein, "solvate" is a form of a compound where solvent molecules are combined in a certain ratio as an integral part of the structure complex of the compound.

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" or "salts thereof" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included are pharmaceutically acceptable salts or compounds of any of the Formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

As used herein, "protecting group" or "protective group" is used as known in the art and as demonstrated in Greene, *Protective Groups in Organic Synthesis.*

As used herein, "hydroxyl protective group" or "hydroxyl protecting group" or "hydroxyl blocking group" refers to the generally understood definition of an alcohol or hydroxyl protecting group as defined in T. W. Greene, *Protective Groups in Organic Synthesis,* John Wiley and Sons, 1991 (hereinafter "Greene, *Protective Groups in Organic Synthesis*").

As used herein, "acid protective group" or "acid protecting group" or "carboxylic acid blocking group" refers to the generally understood definition of protection for the carboxylic acid group as defined in T. W. Greene, *Protective Groups in Organic Synthesis,* John Wiley and Sons, 1991 (hereinafter "Greene, *Protective Groups in Organic Synthesis*").

As used herein, "amine protective group" or "amine protecting group" refers to the generally understood definition of protection for the amino group as defined in T. W. Greene, *Protective Groups in Organic Synthesis,* John Wiley and Sons, 1991 (hereinafter "Greene, *Protective Groups in Organic Synthesis*").

As used herein, "an alcohol protecting group" or "alcohol protective group" is a functional group that protects the alcohol group from participating in reactions that are occurring in other parts of the molecule. Suitable alcohol protecting groups are well known to those of ordinary skill in the art and include those found in T.W. Greene, *Protecting Groups in Organic Synthesis*, John Wiley & Sons, Inc. 1981, the entire teachings of which are incorporated herein by reference. Exemplary alcohol protecting groups include, but are not limited to, actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS) ether), tetrahydropyranyl (THP), methyl ether and ethoxyethyl ether (EE). In some embodiments, the terms "hydroxyl protecting group" and "alcohol protecting group" are used interchangeably.

As used herein, substantially pure compound or isomer refers to one isomer being 90% of the resulting isomeric mixture, or preferably 95% of the resulting isomeric mixture, or more preferably 98% of the resulting isomeric mixture, or even more preferably 99% of the resulting isomeric mixture, and most preferably above 99% of the resulting isomeric mixture.

In one aspect, processes are providing for preparing prostacyclin derivatives. Such derivatives may in some embodiments, include derivatives of Treprostinil and Beraprost. The processes also include the preparation of a number of intermediate compounds useful in the preparation of prostacyclin derivatives. In one aspect, a process is provided to produce a pharmaceutical compound represented by the general Formula (I), Formula (II), Formula (III), and Formula (IV) in a substantially isomerically pure form. The process is completed in fewer steps than the known synthetic methods, and may be conducted to prepare commercially useful quantities. In another aspect, synthetic methods are provided for producing analogues of prostacyclin derivatives such as Beraprost, which are stereoselective, efficient, scalable and economical. In another aspect, substantially isomerically pure compounds and intermediates are produced by the above processes. Beraprost and its salts, such as the sodium salt are effectively used for the treatment of various conditions such as pulmonary hypertension, chronic peripheral vascular disease and arterial thrombosis. Therefore, in one aspect the present invention includes methods of treating these conditions comprising administering the compounds to a subject in need thereof.

In one embodiment, the present technology relates to a new process for the preparation of Beraprost using new intermediates. The process is a much more efficient, commercially viable process to manufacture the target compounds. In other embodiments, novel synthetic intermediate compounds useful for the synthesis of Beraprost and other prostacyclin derivatives are provided.

One embodiment provides a process for the preparation of a compound of Formula I,

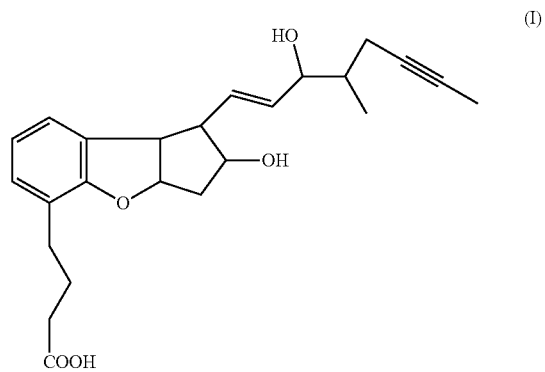 [SMILES: CC#CCC(C)C(O)/C=C/C1C(O)CC2Oc3c(CCCC(=O)O)cccc3C21]

or a hydrate, solvate, prodrug, or pharmaceutically acceptable salt thereof, which comprises:
(a) reacting a substituted halophenol of Formula (II) with 6-oxabicyclo[3.1.0]hex-2-ene to form an ether compound represented by structural Formula (III):

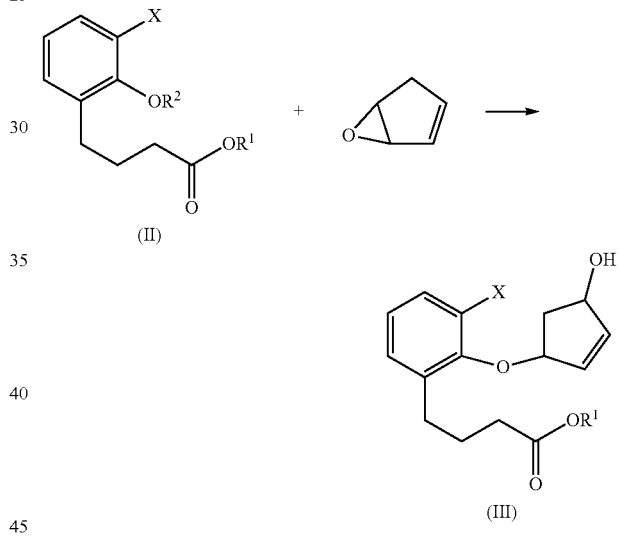

wherein, X is F, Cl, Br or I; $R^1$ is an alkyl, cycloalkyl or TBDMS; and $R^2$ is independently H or an alcohol protecting group.

The reaction is conducted in the presence of a suitable catalyst and solvent. Suitable catalysts include, but are not limited to, metal catalysts, e.g., a palladium catalyst such as $PdCl_2(PPh_3)_2$, $Pd(Ph_3)_4$, and $PdCl_2(dppf)_2$, $Pd(OAc)_2$, $Pd_2(dba)_3$. In one embodiment, the palladium catalyst is $PdCl_2(PPh_3)_2$.

Suitable solvents include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane (DCM), ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran (THF), dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof. In one embodiment, the solvent is THF.

The 6-oxabicyclo[3.1.0]hex-2-ene used in the above reaction can be obtained starting from dicylcopentadiene as shown in the scheme below.

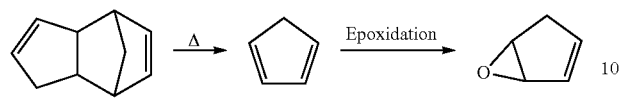

The dicyclopentadiene dimer is warmed to a suitable temperature and distilled to obtain the pentadiene monomer, which is then subjected to peracetic acid epoxidation to obtain 6-oxabicyclo[3.1.0]hex-2-ene.

(b) Acetylating the ether compound of Formula (III) to form a compound of Formula (IV)

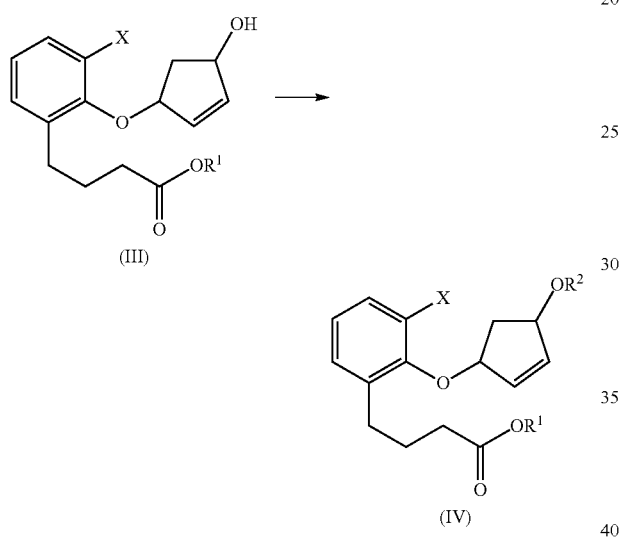

wherein X, $R^1$ are as defined above; and $R^2$ is an acetyl group.

Suitable acetylation methods are known in the art. For example, the compound of Formula (III) can be treated with a suitable acetylating agent, for example carboxylic acids or carboxylic anhydrides, such as propionic anhydride or acetic anhydride, optionally in the presence of a suitable catalyst. The catalysts suitable for this reaction include, but are not limited to, 4-dimethylaminopyridine (DMAP), 4-pyrollidinopyridine trifluoroacetic acid, alkyl sulfonic acids, aryl sulfonic acid, fluorinated alkylsulfonic acid, acetic acid, citric acid, ascorbic acid, tetrabutyl ammonium hydrogen sulfate, 4-(dimethylamino) pyridine, sodium carbonate, pyridine, potassium carbonate, sodium bicarbonate, tetrabutyl ammonium hydroxide, choline hydroxide, sodium acetate, potassium acetate, zinc acetate and ammonium acetate.

The ether compound (III) may be dissolved in a suitable solvent prior to acetylation. Suitable solvents include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane (DCM), ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran (THF), dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof. In one embodiment, the solvent is DCM.

(c) Allylating the compound of Formula (IV) with allyltributylstannane in presence of AIBN to form the allylation product (V)

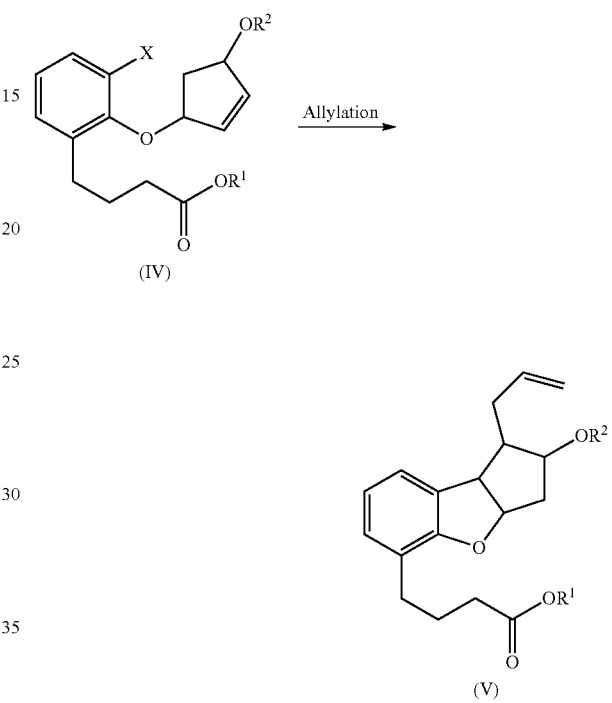

wherein X, $R^1$ and $R^2$ are as defined above.

The allylation reaction can be conducted using suitable allylating reagents known in the art such as for example allyltributyltin (allyl-Bu$_3$Sn), allylmagnesium bromide (allyl-MgBr); allyl halide such as allyl chloride, allyl bromide, or allyl iodide; allyltrihalosilane such as allyltrichlorosilane allyltribromosilane; allyl carboxylate; allyl carbonate; diallyl carboxylate; diallyl sulfate or metalallyl reagent and the like or combinations thereof. In one embodiment, the allylating agent is allyltributyltin. In one embodiment, the halo compound of Formula (IV) is subjected to Keck radical allylation using allyltributyltin and a radical initiator. Suitable radical initiators are known in the art and include, but are not limited to, azobis-iso-butyronitrile (AIBN), or peroxides like di-tert-butyl, dilauroyl, or dibenzoyl peroxide. Suitable solvents such as those listed herein may be employed for the allylation reaction. In one embodiment, hydrocarbon solvents such as toluene, benzene, xylene, hexane, cylcohexane, ethylbenzene, or halogenated hydrocarbon solvents, such as halobenzene, dichloromethane, chloroform and the like are used for the allylation reaction.

(d) Subjecting the terminal alkene compound of Formula (V) to intermolecular allylic acetoxylation to form a compound of Formula (VI)

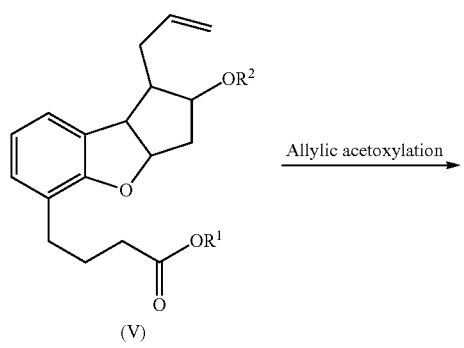

(V)

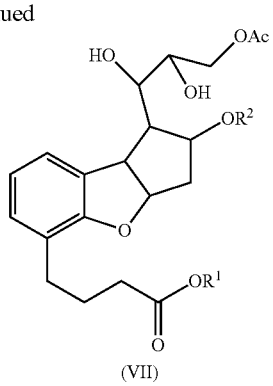

(VII)

Allylic acetoxylation

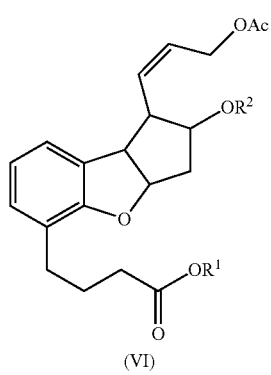

(VI)

wherein R¹ and R² are as defined above.

The intermolecular allylic acetoxylation reaction can be conducted using a carboxylic acid such as acetic acid in presence of a metal catalyst such as a Pd (II) catalyst. Suitable metal catalysts are known in the art and include, $PdCl_2$, $Pd(OAc)_2$, $Pd(OOCCF_3)_2$, $Pd(dba)_2$, $PdBr_2$, Pd(OTf)$_2$, and the like or combinations thereof. Suitable solvents such as those listed herein may be employed for the allylation reaction. In one embodiment, the solvent is dimethylacetamide (DMA).

(e) Subjecting the compound of Formula (VI) to dihydroxylation to form a compound of Formula (VII)

wherein R¹ and R² are as defined above.

The butenyl acetate side-chain of compound (VI) is subjected to catalytic dihydroxylation using an oxidant. The catalyst used in the process is an osmium catalyst. Suitable oxidants or sources of oxygen known in the art can be used in the dihydroxylation process. Suitable oxidants include, but are not limited to, N-methylmorpholine N-oxide (NMO), amine oxides (e.g., trimethyl amine oxides), tert-butyl hydroperoxide, hydrogen peroxide, and oxygen plus metal catalysts (e.g., copper ($Cu^+$—$Cu^{++}/O_2$), platinum ($Pt/O_2$), palladium ($Pd/O_2$) and the like or combinations thereof. In one embodiment, N-methylmorpholine N-oxide (NMO) is used as the oxidant. Osmium will generally be provided in the form of osmium tetroxide ($OsO_4$), although other sources (e.g., osmium trichloride anhydrous, osmium trichloride hydrate) can be used. $OsO_4$ can be added as a solid or in solution. In one embodiment, compound (VI) is subjected to catalytic dihydroxylation using N-methylmorpholine N-oxide (NMO) oxidant and a catalytic amount of $OsO_4$. Suitable solvents such as those listed herein may be employed for the dihydroxylation reaction. In one embodiment, the solvent is a combination of alcohol, water and an inert solvent. In one embodiment, the solvent includes a mixture of butanol, water and THF.

(f) Subjecting the dihydroxy compound (VII) to oxidation to form an aldehyde compound of Formula (VIII)

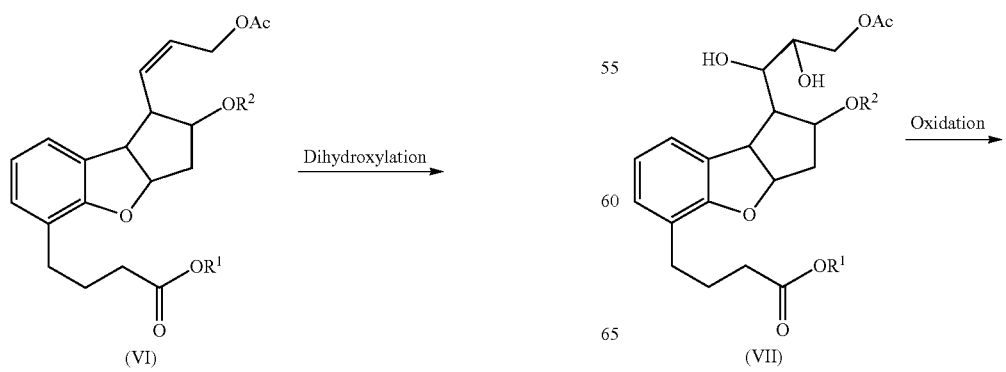

(VI) Dihydroxylation (VII) Oxidation

-continued

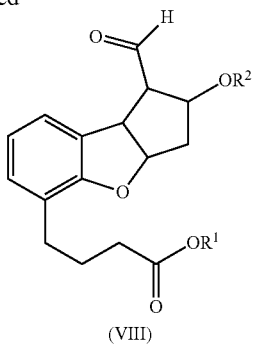

(VIII)

wherein R¹ and R² are as defined above.

The dihydroxy compound (VII) is subjected to oxidation to form an aldehyde compound of Formula (VIII). Suitable oxidation conditions and reagents known in the art can be employed for this oxidation reaction. In one embodiment, the dihydroxy compound is subjected to periodate oxidation. Suitable periodates used for the oxidation reaction include, but are not limited to, sodium metaperiodate, trisodium periodate, potassium periodate, trisodium paraperiodate, and the like and combinations thereof. In one embodiment, the dihydroxy compound is oxidized using sodium metaperiodate. Suitable solvents such as those listed herein may be employed for the oxidation reaction. In one embodiment, the solvent is a combination of water and an organic solvent. In one embodiment, the solvent includes a mixture of water and dichloroethane.

(g) Reducing the aldehyde compound of Formula (VIII) and removing the acetyl group to provide a diol of Formula (IX)

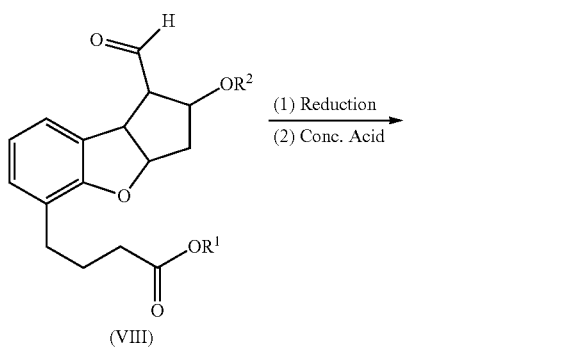

wherein R¹ is as defined above.

Any alkali metal borohydride, such as sodium borohydride, potassium borohydride or lithium borohydride may be used in the reduction of the aldehyde compound (VIII) to an alcohol of Formula (IX). Suitable solvents such as those listed herein may be employed for the oxidation reaction. In one embodiment, the solvent includes an alcoholic solvent such as methanol, ethanol, isopropanol and the like or combinations thereof. In one embodiment, the solvent is methanol.

The acetyl group is removed under acidic or basic conditions. In one embodiment, the compound of Formula (IX) is deacetylated under acidic conditions. Any acid may be used for this purpose. Exemplary acids include but are not limited to, hydrochloric acid, hydrobromic acid, sulfuric acid, acetic acid, nitric acid and perchloric acid. In one embodiment the acid is sulfuric acid. The resulting esterdiol compound (IX) is an important intermediate which can be used to prepare Beraprost.

(h) Converting the diol of Formula (IX) to a protected aldehyde of Formula (VIIIA); and

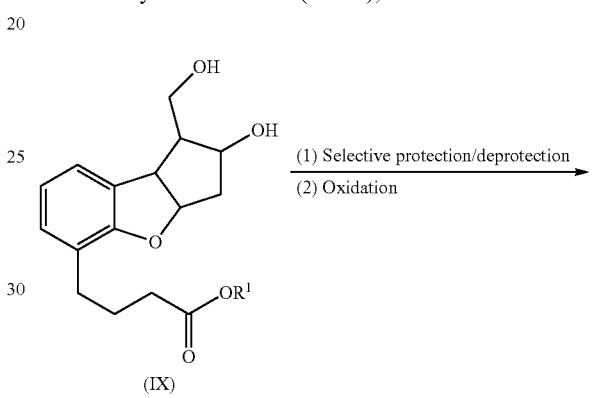

(IX)

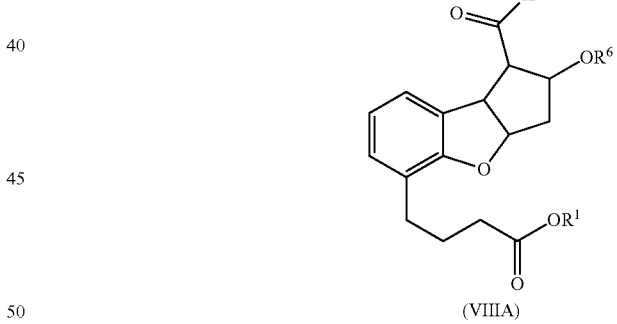

(VIIIA)

wherein R⁶ is an alcohol protecting group;

The diol can be selectively protected at the primary alcohol with suitable protecting groups, e.g., trityl ether, followed by protecting the secondary alcohol group with suitable alcohol protecting groups defined herein. In one embodiment, the secondary alcohol protecting group is TBDMS. The dual alcohol protected compound is then subjected to selective deprotection of trityl group with a suitable deprotecting agent such as Et₂AlCl to afford the alcohol intermediate which is further subjected to Swern oxidation to obtain the protected aldehyde intermediate of Formula (VIIIA).

(i) Reacting the protected aldehyde of Formula (VIIIA) with a phosphonate of Formula (X) to obtain a compound of Formula (I),

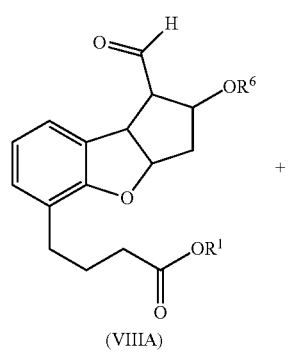

(VIIIA)

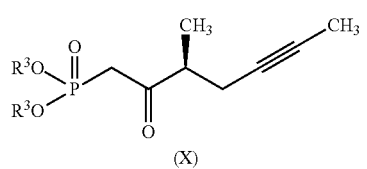

(X)

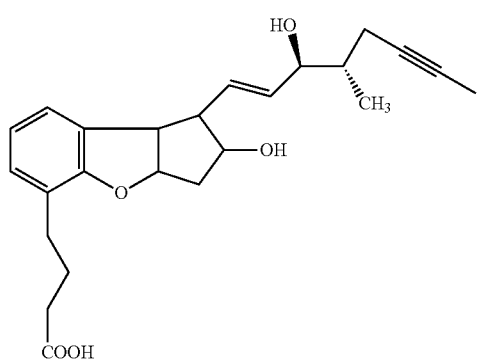

(I)

wherein, $R^3$ is a straight or branched alkyl group having 1-4 carbon atoms; $R^6$ is an alcohol protecting group and $R^1$ is as defined above.

The aldehyde compound of Formula (VIIIA) and the phosphonate of Formula (X) are reacted in a Wittig-Horner-Emmons reaction as described in Chem. Rev., volume 74, page 87 (1974) to obtain Beraprost. The process for coupling the keto-phosphonate side chain (X) to the core Beraprost aldehyde analogue (VIIIA) is described in WO2012/174407, assigned to the assignee of the present invention, the entire contents of which are incorporated herein by reference.

In one embodiment, the process for preparing Beraprost is as depicted in the following Scheme I.

Scheme I:

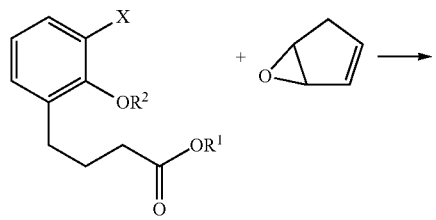

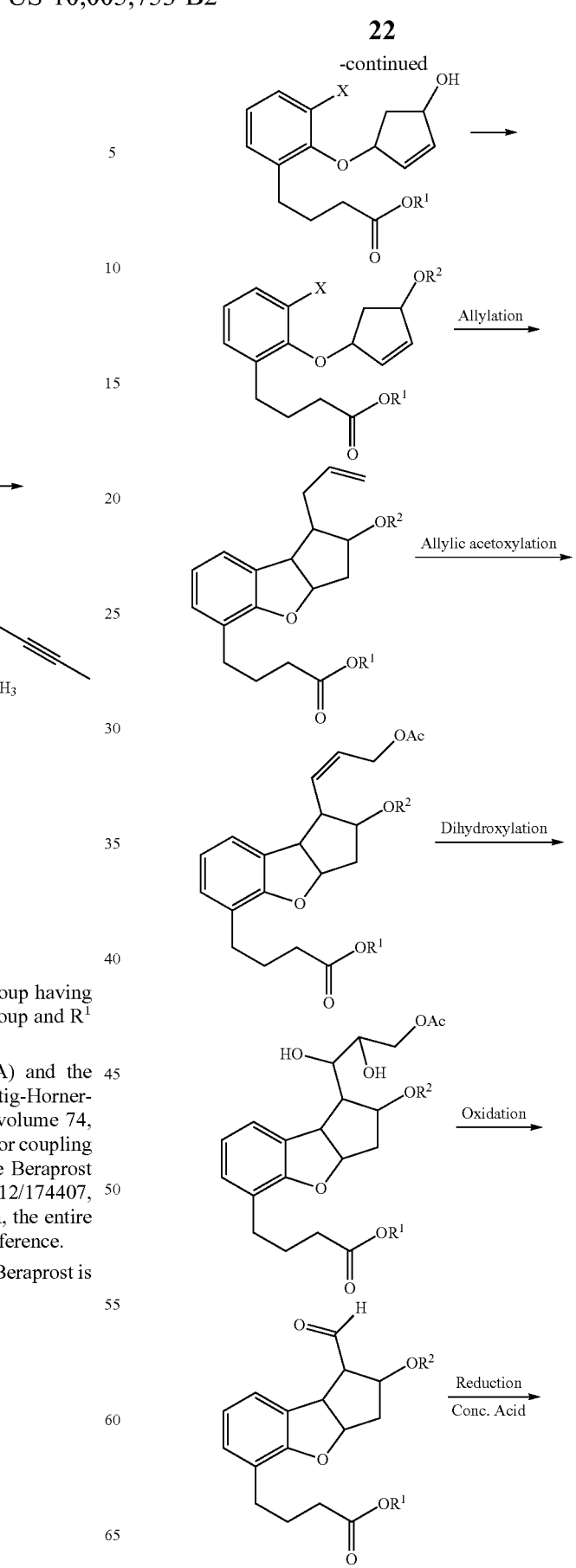

23

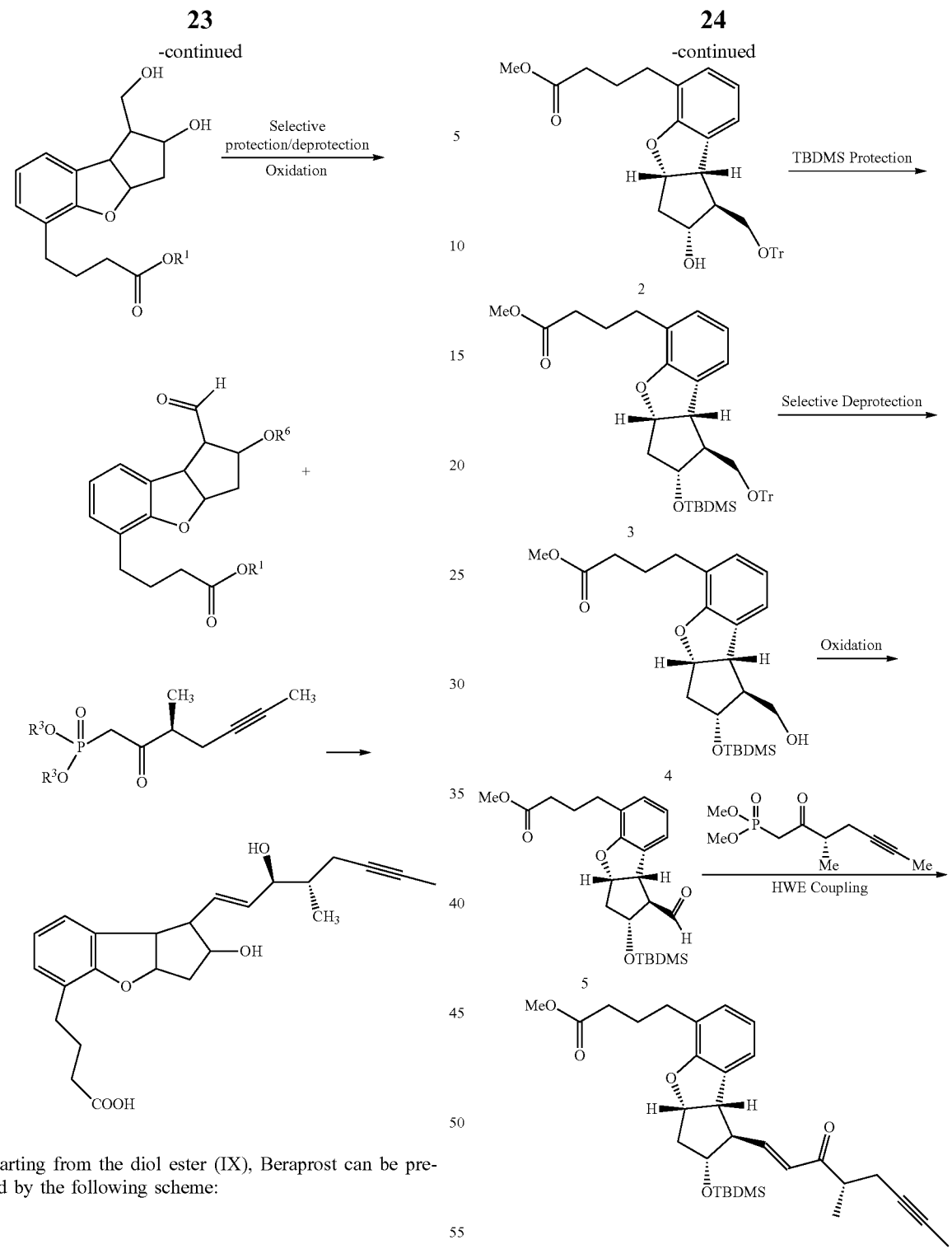

Starting from the diol ester (IX), Beraprost can be prepared by the following scheme:

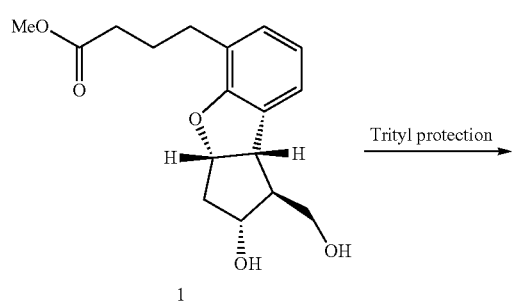

As shown in the above scheme, the diol (1) is regioselectively protected at the primary alcohol with trityl ether (2) followed by protection with TBDMS ether at the secondary alcohol (3). The chemoselective deprotection of trityl ether (3) is achieved with Et$_2$AlCl to obtain alcohol intermediate (4). The alcohol intermediate (4) is subjected to Swern oxidation to obtain an aldehyde intermediate (5) which upon Homer-Wordsworth-Emmons (HWE) coupling with pure phosphonate side-chain in the presence of mild base LiOH.H$_2$O provided the enone intermediate (6).

The enone intermediate (6) can then be converted to Beraprost using the following scheme:

using Corey's reagent i.e. CBS reduction. Finally, ester (9) is hydrolyzed using base followed by potassium salt formation to obtain Beraprost as single-isomer in the form of the potassium salt.

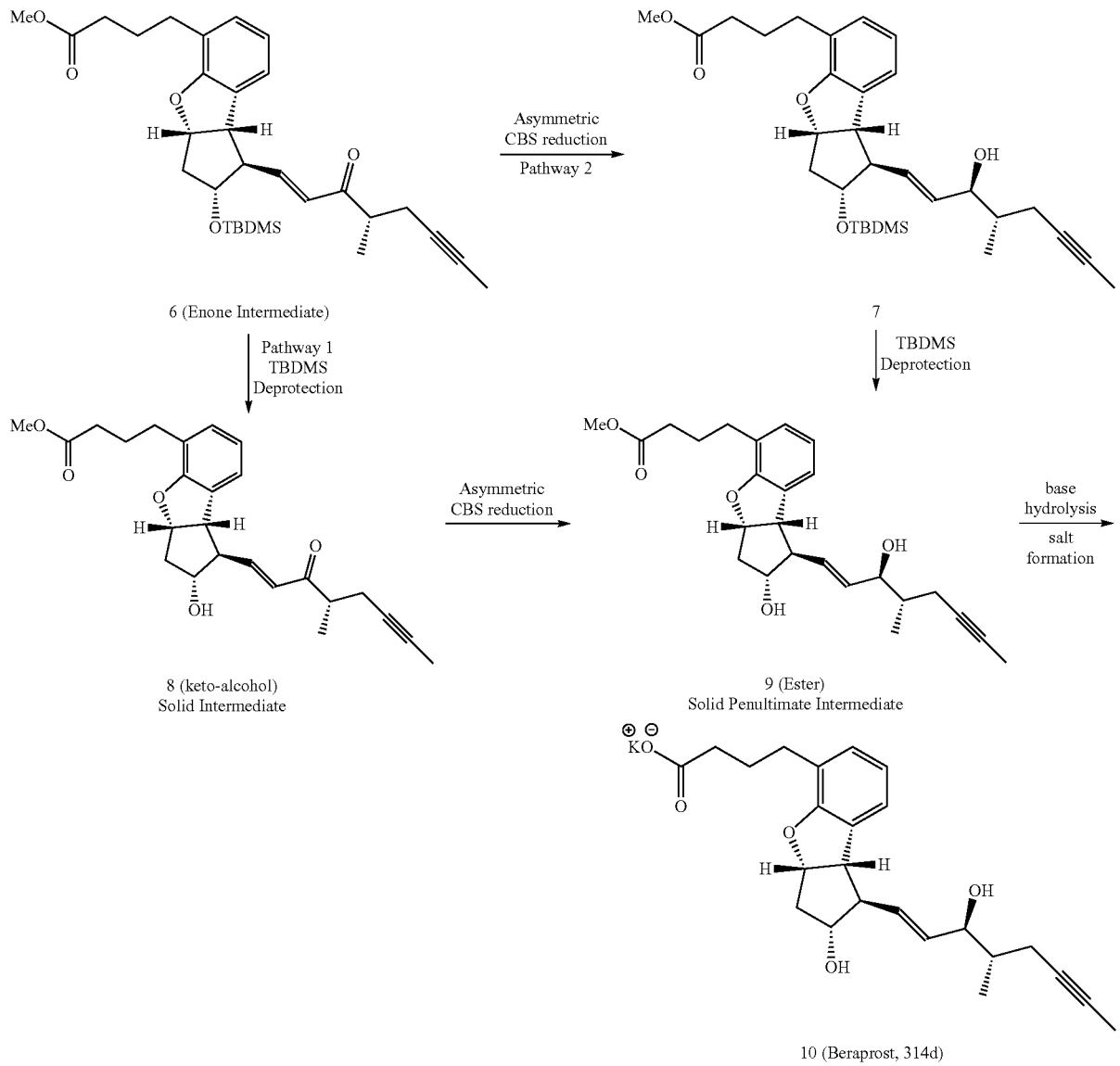

Beraprost can be prepared from the enone intermediate (6) via two possible pathways as depicted in the above scheme. One pathway includes cleaving the TBDMS group of enone (6) to obtain keto-alcohol which can be crystallized to obtain the diastereomerically pure keto-alcohol (8). This is subjected to asymmetric CBS reduction (step 8→9) to obtain the penultimate intermediate of Beraprost as an ester (9). In another embodiment, the reduction step on the enone intermediate (6) is carried out first (step 6→7) to provide intermediate (7) which is subjected to subsequent cleavage of TBDMS group to obtain penultimate intermediate of Beraprost as an ester (9) which is purified by crystallization. The ketones (6 and 8) are subjected to asymmetric reduction The phosphonate compound of Formula (X) can be prepared starting from (1S,2S)-pseudoephedrine or from (1R, 2R)-pseudoephedrine as shown in the following Scheme II. In Scheme II, R$^3$ is a straight or branched alkyl group having 1-4 carbon atoms.

Scheme II:

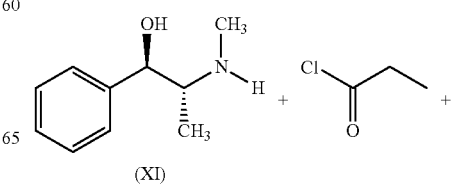

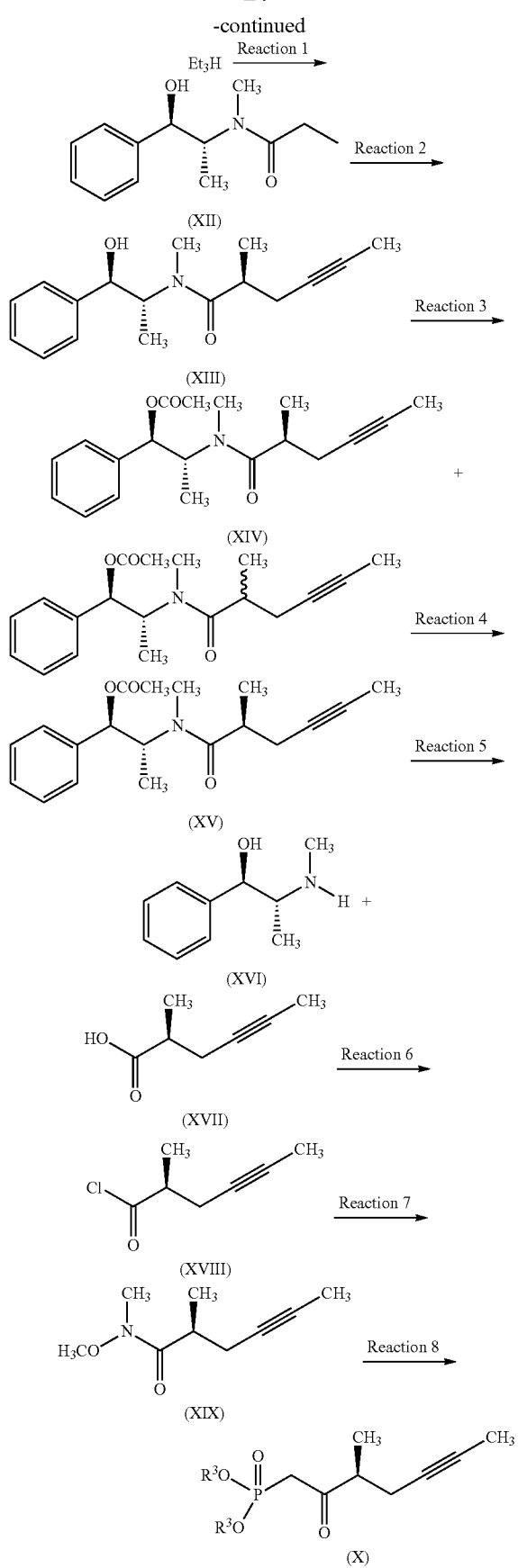

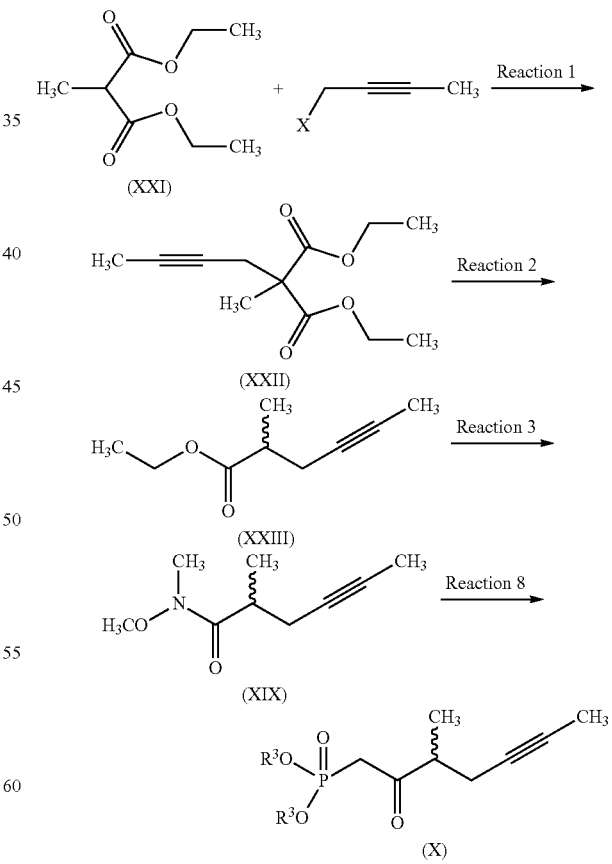

As depicted in Scheme II, (1R, 2R)-pseudoephedrine (XI) is treated with propionyl chloride in presence of a base such as triethylamine to form the N-methyl propionamide compound (XII), which is then treated with a halobutyne, e.g., 1-chloro-2-butyne, 1-bromo-2-butyne, 1-iodo-2-butyne, in presence of an alkali metal amide base such as $LiN(SiMe_3)_2$, $NaN(SiMe_3)_2$, $KN(SiMe_3)_2$, and the like or combinations thereof, to provide coupled product (XIII). The diastereomeric coupled product (XIII) is treated with acetic anhydride, in the presence of a catalyst such as 4-dimethylaminopyridine (DMAP), to provide the acetylated product (XIV). The acetylated product (XVI) is treated with an acid such as sulfuric acid to yield the amine product (XVI) and the acid product (XVII), which is then converted to the acid chloride (XVIII) using the oxalyl chloride mechanism. The acid chloride is treated with N,O-dimethylhydroxylamine hydrochloride to provide the corresponding N-methoxy-N-methylamine compound (XIV), which is further treated with dimethyl methylphosphonate lithium salt, which can be generated by reacting dimethyl methylphosphonate with alkyl lithium, such as n-butyllithium or methyllithium leading to the generation of the phosphonate compound (X).

Alternatively, the phosphonate compound of Formula (X) can be generally prepared as shown in the following Scheme III. In Scheme III, $R^3$ is a straight or branched alkyl group having 1-4 carbon atoms.

Scheme III:

As depicted in Scheme III, diethylmethyl malonate (XXI) is treated with a halobutyne, e.g., 1-chloro-2-butyne, 1-bromo-2-butyne, 1-iodo-2-butyne, in presence of an alkali metal amide base such as LiN(SiMe$_3$)$_2$, NaN(SiMe$_3$)$_2$, KN(SiMe$_3$)$_2$, and the like or combinations thereof, to provide coupled product (XXII). The coupled product (XXII) is treated with lithium chloride to provide ethyl 2-methylhex-4-ynoate (XXIII). Compound (XXIII) is reacted with N,O-dimethylhydroxylamine hydrochloride to provide the corresponding N-methoxy-N-methylamine compound (XIX), which is further treated with dimethyl methylphosphonate lithium salt, which can be generated by reacting dimethyl methylphosphonate with alkyl lithium, such as n-butyl-lithium or methyllithium leading to the generation of the phosphonate compound (X).

In one embodiment, Phosphonate compound (X), e.g., (S)-Dimethyl-(3-methyl-2-oxohept-5-yn-1-yl)phosphonate (8) can be prepared starting from (1R,2R)-pseudoephedrine according to the following Scheme IV.

lation of amide (3) with in situ generated 1-iodo-2-butyne from 1-bromo-2-butyne and sodium iodide in the presence of lithium diisopropylamide (LDA) and anhydrous lithium chloride as additive in tetrahydrofuran at −78° C. afforded (1R,2R)-pseudoephedrinemethylhexynamide (4) in 92% yield and 97.6% (de). The crystallization of methylhexynamide (4) with various solvents to enrich the chiral purity was not successful. In order to get the crystalline methylhexynamide, the 4 is derivatized to the corresponding acetate (5) using acetic anhydride and 4-(dimethylamino)pyridine in dichloromethane at room temperature in high yield. The acetate (5) is crystallized from heptanes as white square crystals. The diastereomeric purity of crystalline acetate (5) is 99.4% (de). The acetate (5) is hydrolyzed with 9N sulfuric acid in 1,4-dioxane to afford chiral carboxylic acid (6) and pseudoephedrine (7) as regenerated chiral auxiliary which

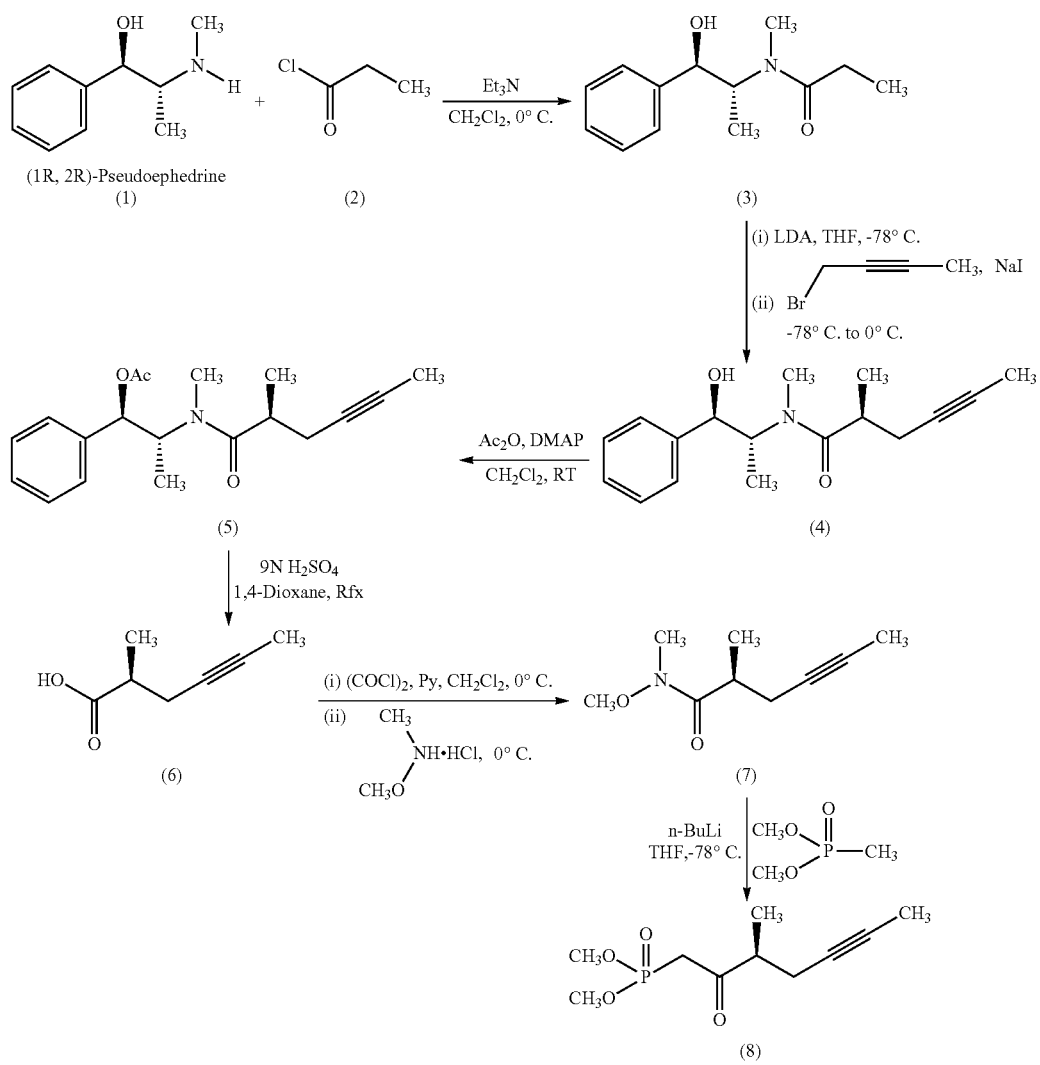

As depicted in Scheme (IV), the propionylation of (1R, 2R)-pseudoephedrine (1) with propionyl chloride (2) in the presence of triethylamine in dichloromethane at 0° C. afforded (1R,2R)-pseudoephedrinepropionamide (3) in high yield. The amide (3) is also available commercially, however only in small quantities. The diastereoselective alkycan be recovered by simple extractive isolation procedure. The acid (6) is converted to Weinreb amide (7) using oxalyl chloride and N,O-dimethylhydroxylamine hydrochloride in the presence of pyridine in dichloromethane at 0° C. The chiral purity of amide (7) is 99.9% as determined by chiral HPLC. The amide (7) is treated with lithium salt of dimethyl methylphosphonate in tetrahydrofuran at −78° C. to afford chiral ketophosphonate (8) with chiral purity of 99.8%. (Ref: D Lucet, T. L. Gall, C. Mioskowski, 0. Ploux, and A. Marquet, *Tetrahedron Asymmetry*, 1996, 7, 985-988).

Alternatively, the phosphonate compound (X), e.g., (S)-Dimethyl-(3-methyl-2-oxohept-5-yn-1-yl)phosphonate (8) can be prepared starting from (1S,2S)-pseudoephedrine according to the following Scheme V.

and anhydrous lithium chloride in tetrahydrofuran would give (1S,2S) pseudoephedrinemethylhexynamide (12). Acetylation of amide (12) with acetic anhydride in the presence of 4-(dimethylamino)pyridine followed by acid hydrolysis would give the same carboxylic acid, (S)-2-methyl-hex-4-ynoic acid (6). By the proper choice of the N-acyl group, alkyl halide, and the configuration of pseudoephedrine auxiliary (1R,2R or 1S,2S), (S)-2-methyl-hex-

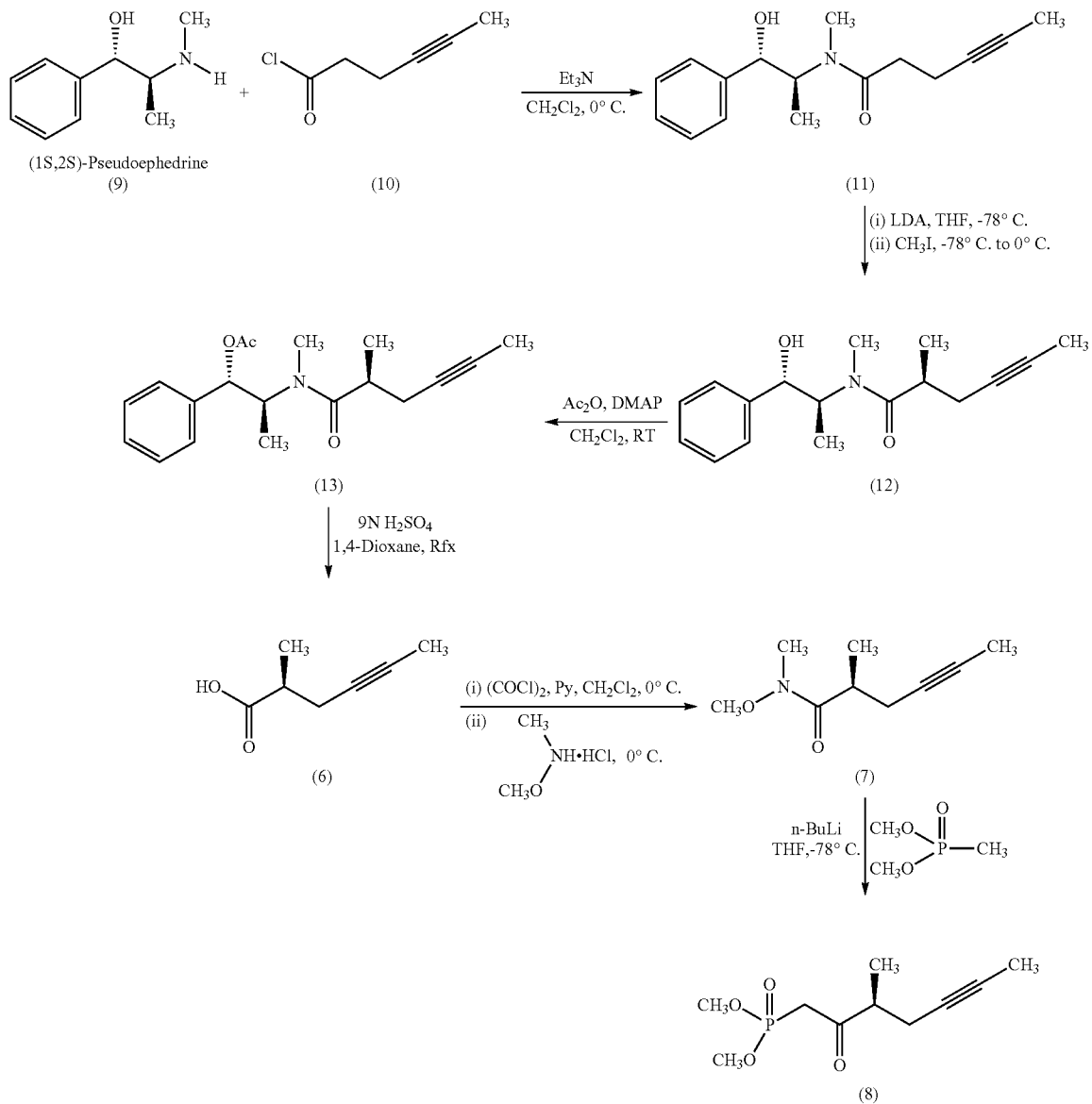

Scheme V:

The (S)-3-methyl-2-oxohepta-5-ynylphosphonic acid dimethyl ester (8) could be synthesized by using (1S,2S)-pseudoephedrine (9), an enantiomer of (1R,2R)-pseudoephedrine (1) as shown in (Ref: A. G. Myers, B. H. Yang, H. Chen, L. McKinstry, D. J. Kopecky, and J. L. Gleason, *J. Am. Chem. Soc.* 1997, 119, 6496-6511). The acylation of (1S,2S)-pseudoephedrine (9) with 4-hexynoyl chloride (10) in the presence of triethylamine would give carboxamide (11). The diastereoselectivemethylation of carboximide (11) methyl iodide in the presence of diisopropylamide (LDA)

4-ynoic acid (6) could be synthesized. The chirally enriched acid (6) is converted to the desired ketophosphonate side chain for the synthesis of single isomer of Beraprost (314d).

In order to determine the chiral purity of (S)-dimethyl-(3-methyl-2-oxohept-5-yn-1-yl)-phosphonate (8), the corresponding racemic ketophosphonate i.e., racemic dimethyl-(3-methyl-2-oxohept-5-yn-1-yl)phosphonate (20) is synthesized as shown in the following Scheme VI.

Scheme VI:

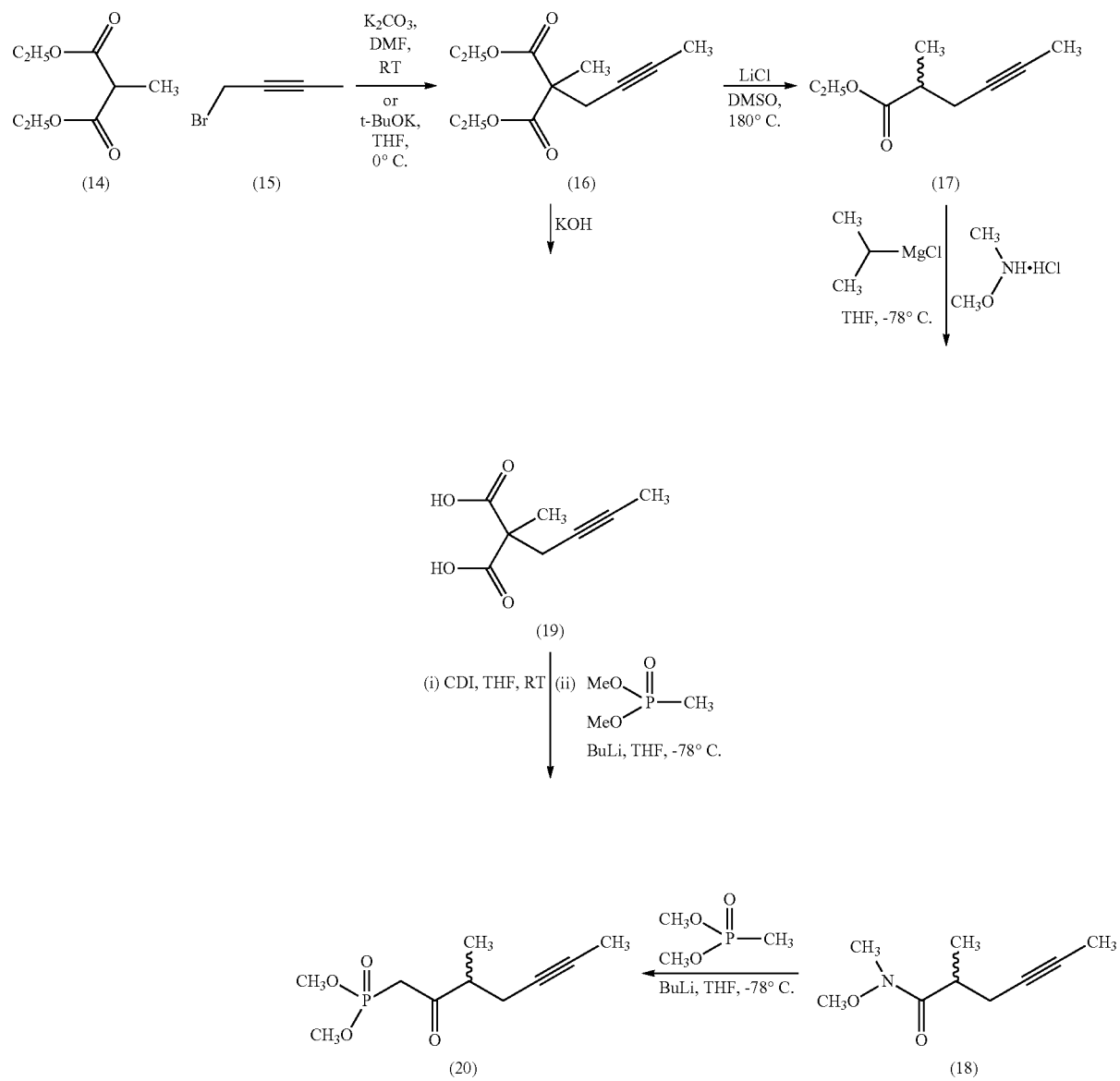

The alkylation of diethyl methylmalonate (14) with 1-bromo-2-butyne (15) in the presence of potassium carbonate in N,N-dimethylformamide at room temperature or potassium tert-butoxide in tetrahydrofuran at room temperature afforded diethyl methyl-(2-butynyl)malonate (16) in quantitative yield. The decarboethoxylation of malonate (16) with lithium chloride in dimethylsulfoxide at 180° C. gave racemic ethyl 2-methyl-hex-4-ynoate (17) in good yield. The racemic ester (17) is converted to Weinreb amide (18) using isopropylmagnesium chloride and N, O-dimethylhydroxylamine hydrochloride in tetrahydrofuran at −78° C. The racemic amide (18) is treated with lithium derivative of dimethyl methylphosphonate in tetrahydrofuran at −78° C. to give racemic dimethyl-(3-methyl-2-oxohept-5-yn-1-yl)-phosphonate(20). The ketophosphonate (20) is also obtained from diethyl methyl-(2-butynyl)malonate (18) via the corresponding malonic acid (19) and 1,1'-carbonyldiimidazole (CDI) and lithium salt of dimethyl methylphosphonate in tetrahydrofuran.

To determine the diastereomeric purity of (1R,2R)-pseudoephedrine methylhexynamide acetate (5), the corresponding racemic acetate (23) is synthesized as shown in the following Scheme VII.

Scheme VII:

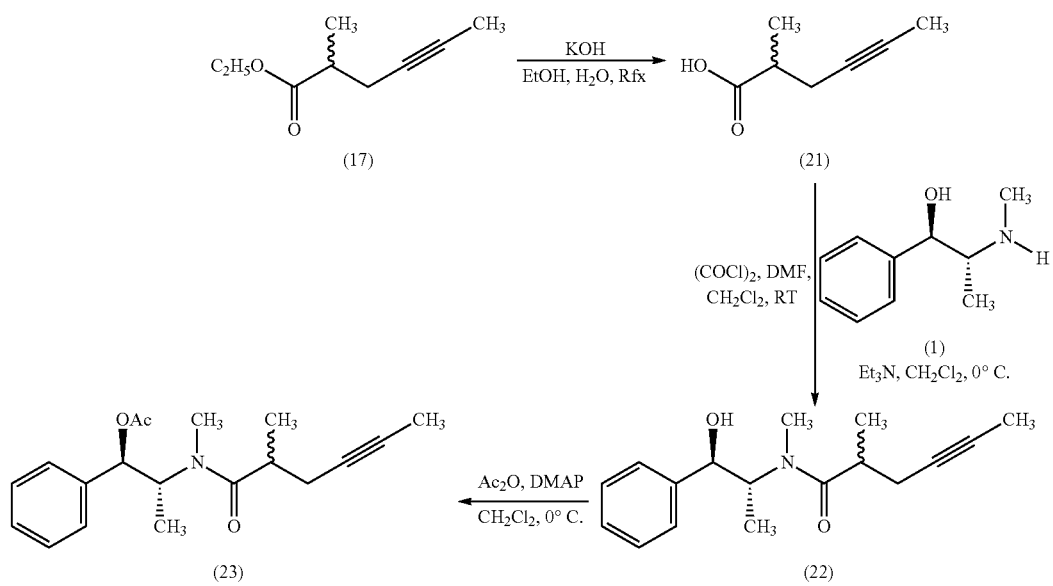

The racemic ethyl 2-methyl-hex-4-ynoate (17) is hydrolyzed with potassium hydroxide in aqueous ethanol to give racemic 2-methylhex-4-ynoic acid (21). The carboxylic acid (21) is converted to acid chloride using oxalyl chloride followed by acylation of (1R,2R)-pseudoephedrine (1) to afford diastereomeric mixture of pseudoephedrine methylhexynamide (22) in good yield. The acetylation of amide (22) with acetic anhydride in the presence of 4-(dimethylamino)pyridine gave diastereomeric mixture of pseudoephedrine methylhexynamide acetate (23) in very good yield.

For the reactions described herein, suitable solvents include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane (DCM), ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran (THF), dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof. In one embodiment, the solvent is THF.

For the reactions described herein, suitable temperatures for the reaction are less than about 500° C., less than about 300° C., less than about 200° C., less than about 100° C., less than about 80° C., less than about 60° C., less than about 40° C., less than about 20° C., less than about 0° C., less than about −10° C., or any other suitable temperatures. In some embodiments, the reaction temperature is the room temperature. Suitable reaction times depend on the temperature and other conditions, and may be less than about 30 hours, less than about 20 hours, less than about 10 hours, less than about 5 hours, less than about 2 hours, less than about 1 hour, or any other suitable times. Longer times may also be suitable.

One embodiment of the invention relates to novel synthetic intermediates of Beraprost represented by the following structural Formula (XV) and methods of preparing them.

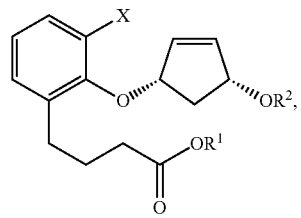

(XV)

wherein:

X is F, I, Cl or Br;

$R^1$ is an alkyl, cycloalkyl or TBDMS; and $R^2$ is independently H or an alcohol protecting group.

In some embodiments, X is Br, Cl or I. In some embodiments, $R^1$ is methyl or ethyl. In some embodiments, $R^2$ is H, THP or TBDMS.

In some embodiments, the compound of Formula (XV) has the Formula (XVA)

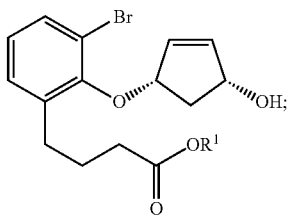

(XVA)

wherein $R^1$ is methyl or ethyl group.

Another embodiment of the invention relates to novel synthetic intermediates of Beraprost represented by the following structural Formula (XVI) and methods of preparing them.

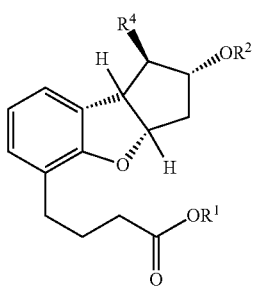

(XVI)

wherein:
$R^1$ is methyl or ethyl;
$R^2$ is independently H or an alcohol protecting group; and
$R^4$ is $CH(OH)CH_2OH$ or $CH=CH_2$.

Yet another embodiment of the invention relates to novel synthetic intermediates of Beraprost represented by the following structural Formula (XVII) and methods of preparing them.

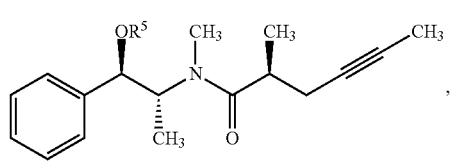

(XVII)

wherein $R^5$ is H or acetyl group.

Suitable methods for producing novel compounds of Formula (XV), (XVI) or (XVII) are as described herein.

In the compounds and methods described above, X represents a halogen. In some embodiments, X is F, Cl, Br or I. In some embodiments, X is F. In some embodiments, X is Cl. In some embodiments, X is Br. In some embodiments, X is I.

In some embodiments, $R^1$ is H. In some embodiments, $R^1$ is an alkyl group. In some embodiments, $R^1$ is a $C_{1-6}$ alkyl group. In other embodiments, $R^1$ is an acid protective group. Suitable carboxylic acid protective groups $R^1$ are known in the art and include the ester derivatives of a carboxylic acid group commonly employed to block or protect the carboxylic acid group while reactions are carried out on other functional groups on the compound. Exemplary groups for the protection of the carboxylate group include allyl, methyl, ethyl, nitrobenzyl, dinitrobenzyl, tetrahydropyranyl, methoxybenzyl, dimethoxybenzyl, trimethoxybenzyl, trimethylbenzyl, pentamethylbenzyl, methylenedioxybenzyl, benzhydryl, 4,4' dimethoxybenzhydryl, 2,2'4,4'-tetramethoxybenzhydryl, t-butyl, t-amyl, trityl, 4 methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, b-(tri-methylsilyl)ethyl, b (di(n-butyl)methylsilyl)ethyl, p-toluenesulfonylethyl, 4-nitrobenzylsulfonylethyl, cinnamyl, 1-(trimethylsilylmethyl)prop-1-en-3-yl, and like moieties. In some embodiments, $R^1$ is a benzyl, tertiary-butyl, dimethoxy benzyl, nitrobenzyl or a dinitrobenzyl group.

In some embodiments, $R^2$ is a H. In some embodiments, $R^2$ is an acetyl group. In other embodiments, $R^2$ is an alcohol protective group. Suitable groups for the protection of the hydroxyl groups are known in the art and include, but are not limited to, methyl, t-butyl, tetrahydropyranyl, benzyl, methoxybenzyl, nitrobenzyl, tertiary butyl dimethyl silyl (TBDMS), trimethylsilyl (TMS), tertiary methyl dimethyl silyl group, methoxymethyl, methoxyethoxymethyl, allyl, trityl, ethoxyethyl, 1-methyl-1-methoxyethyl, tetrahydropyranyl, or tetrahydrothiopyranyl group. In one embodiment, the alcohol protective group is tetrahydropyranyl (THP). In one embodiment, the alcohol protective group is tertiary butyl dimethyl silyl (TBDMS).

In some embodiments, $R^3$ is a H. In some embodiments, $R^3$ is a straight or branched alkyl group having 1-4 carbon atoms. In some embodiments, $R^3$ is methyl, ethyl or isopropyl group. In some embodiments, $R^3$ is a methyl group.

In some embodiments, $R^4$ is $CH(OH)CH_2OH$ or $CH=CH_2$. In some embodiments, $R^4$ is $CH(OH)CH_2OH$. In other embodiments, $R^4$ is $CH=CH_2$.

In some embodiments, $R^5$ is a H. In some embodiments, $R^5$ is an acetyl group. In other embodiments, $R^5$ is a hydroxyl protective group.

Another embodiment provides an alternate process for the preparation of racemic Beraprost ester diol of Formula IX,

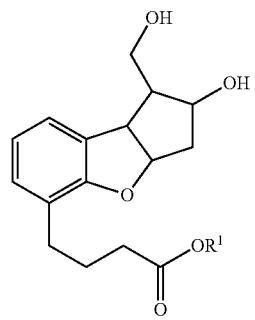

(IX)

which comprises:
(i) reacting a substituted halophenol of Formula (II) with 6-oxabicyclo[3.1.0]hex-2-ene to form an ether compound represented by structural Formula (III):

wherein, X is F, Cl, Br or I; $R^1$ is an alkyl, cycloalkyl or TBDMS; and $R^2$ is independently H or an alcohol protecting group.

The reaction is conducted in the presence of a suitable catalyst and solvent. Suitable catalysts include, but are not limited to, metal catalysts, e.g., a palladium catalyst such as PdCl$_2$(PPh$_3$)$_2$, Pd(Ph$_3$)$_4$, and PdCl$_2$(dppf)$_2$, Pd(OAc)$_2$, Pd$_2$(dba)$_3$. In one embodiment, the palladium catalyst is PdCl$_2$(PPh$_3$)$_2$.

Suitable solvents include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane (DCM), ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran (THF), dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof. In one embodiment, the solvent is THF.

(ii) Allylating the compound of Formula (III) with allyltributylstannane in presence of AIBN to form the allylation product (VA)

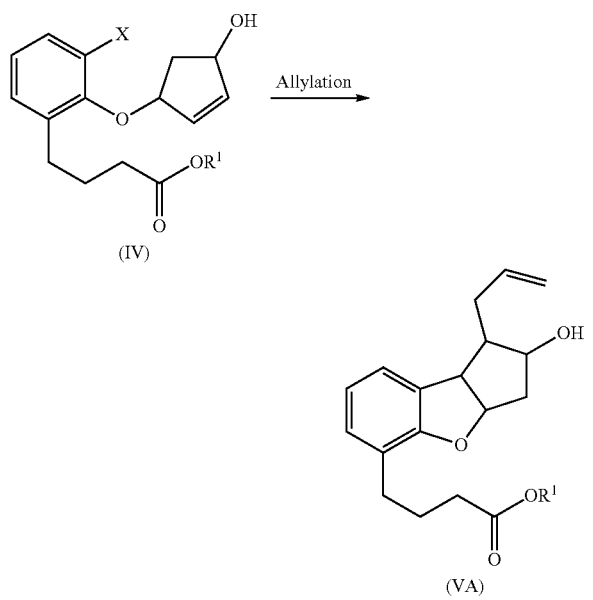

wherein X, R$^1$ and R$^2$ are as defined above.

The allylation reaction can be conducted using suitable allylating reagents known in the art such as for example allyltributyltin (allyl-Bu$_3$Sn), allylmagnesium bromide (allyl-MgBr); allyl halide such as allyl chloride, allyl bromide, or allyl iodide; allyltrihalosilane such as allyltrichlorosilane allyltribromosilane; allyl carboxylate; allyl carbonate; diallyl carboxylate; diallyl sulfate or metalallyl reagent and the like or combinations thereof. In one embodiment, the allylating agent is allyltributyltin. In one embodiment, the halo compound of Formula (IV) is subjected to Keck radical allylation using allyltributyltin and a radical initiator. Suitable radical initiators are known in the art and include, but are not limited to, azobis-iso-butyronitrile (AIBN), or peroxides like di-tert-butyl, dilauroyl, or dibenzoyl peroxide. Suitable solvents such as those listed herein may be employed for the allylation reaction. In one embodiment, hydrocarbon solvents such as toluene, benzene, xylene, hexane, cylcohexane, ethylbenzene, or halogenated hydrocarbon solvents, such as halobenzene, dichloromethane, chloroform and the like are used for the allylation reaction. In one embodiment, the solvent is toluene.

(iii) Subjecting the terminal alkene compound of Formula (VA) to terminal olefin isomerization to form a compound of Formula (VIA)

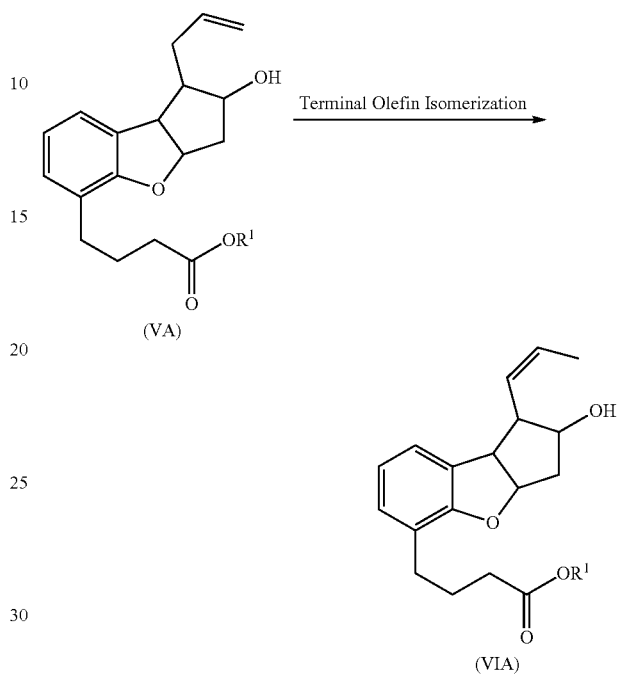

wherein R$^1$ and R$^2$ are as defined above.

The terminal olefin isomerization reaction can be conducted under milder conditions using transition metal catalysts such as for example, hydride and carbonyl hydride complexes of ruthenium, iridium, cobalt, rhodium, osmium, platinum, nickel, iron, and the like or combinations thereof. In one embodiment the catalyst is a ruthenium hydride complex. In one embodiment, the transition metal catalyst is carbonylchlorohydridotris(triphenylphosphine) ruthenium (II). Suitable solvents such as those listed herein may be employed for the isomerization reaction. In one embodiment, hydrocarbon solvents such as toluene, benzene, xylene, hexane, cylcohexane, ethylbenzene, or halogenated hydrocarbon solvents, such as halobenzene, dichloromethane, chloroform and the like are used for the allylation reaction. In one embodiment, the solvent is toluene.

(iv) Ozonolyzing and reducing the compound of Formula (VIA) to provide a diol of Formula (IX)

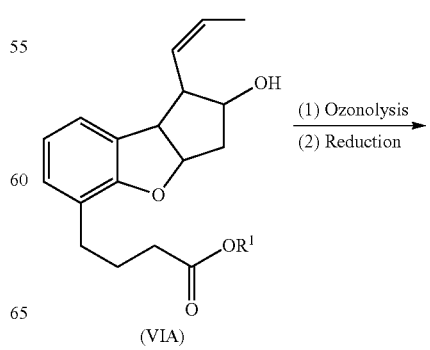

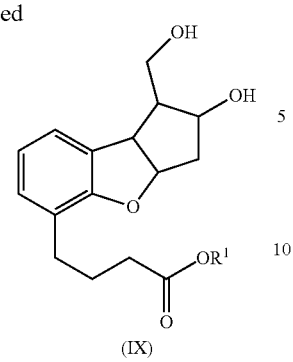

(IX)

wherein R¹ is as defined above.

The alkenyl hydroxy compound (VIA) is ozonolyzed to form an aldehyde intermediate which is further reduced in-situ to obtain the diol compound (IX). Suitable ozonolysis conditions and reagents known in the art can be employed for the reaction. In one embodiment, ozone gas is bubbled through a solution containing the alkenyl hydroxy compound. Suitable solvents such as those listed herein may be employed for the ozonolysis reaction. In one embodiment, the solvent is a combination of one or more organic solvents. In one embodiment, the solvent includes a mixture of anhydrous methanol and dichloromethane. In some embodiments, the solution is cooled prior to an appropriate temperature bubbling ozone gas. In one embodiment, the solution is cooled to −78° C. prior to an appropriate temperature bubbling ozone gas.

Suitable reduction reaction conditions and reagents known in the art can be employed for in-situ reduction of the ozonide intermediate to the diol compound (IX). Any alkali metal borohydride, such as sodium borohydride, potassium borohydride or lithium borohydride may be used for the reduction reaction. Suitable solvents such as those listed herein may be employed for the reduction reaction.

The resulting diol (IX) can be converted in to Beraprost of Formula I using the process described herein.

In one embodiment, the alternate process for the synthesis of racemic Beraprost ester diol by radical cyclization is as depicted in the following Scheme IX.

Scheme IX:

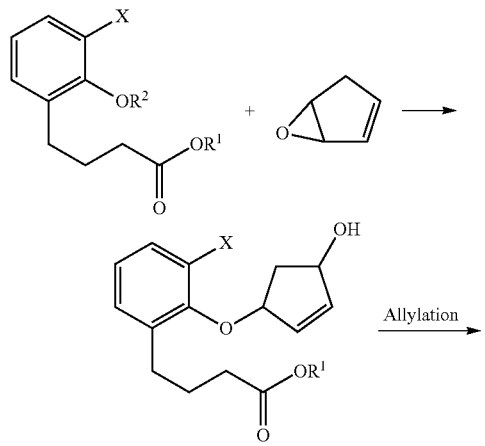

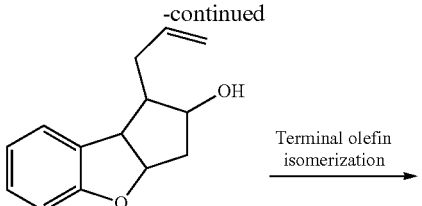

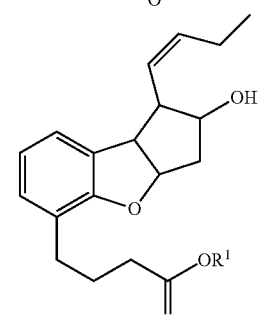

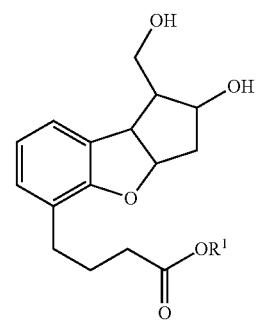

As explained in in Scheme I and Scheme IX, Beraprost can be synthesized by coupling 2-halophenol-6-carboalkoxy-propane with cyclopentadiene monoepoxide or 4-hydroxycyclopentenone to provide a core tricyclic compound of Beraprost. Thus, one embodiment provides a process for the preparation of compound of Formula II,

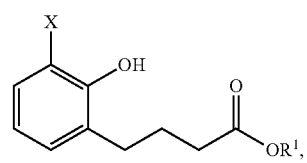

(II)

which comprises:
(i) Oxidizing α-tetralone of Formula (XXV) to form benzolactone represented by structural Formula (XXVI):

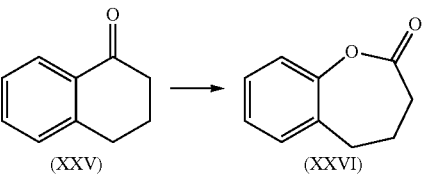

(XXV)  (XXVI)

Suitable oxidation reaction conditions and reagents known in the art can be employed for oxidizing the α-tetralone compound to the benzolactone (XXVI). In one embodiment, the oxidation includes Baeyer-Villiger oxidation of the α-tetralone compound with a suitable peracid. In one embodiment, the peracid is 3-haloperbenzoic acid. Suitable solvents such as those listed herein may be employed for the oxidation reaction.

(ii) Hydrolyzing the benzolactone Formula (XXVI) to provide the compound represented by structural Formula (XXVII):

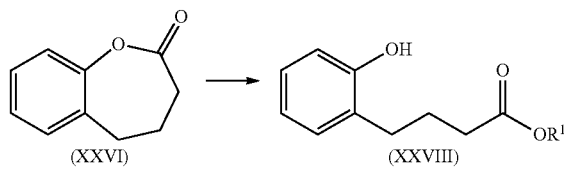

The benzolactone can be hydrolyzed using suitable reagents in the presence of catalyst known in the art such as for example a base catalyst such as sodium or potassium hydroxide or sodium or potassium alkoxide. In one embodiment, the base is sodium methoxide. Suitable solvents such as those listed herein may be employed for the oxidation reaction. In one embodiment, the solvent includes an alcoholic solvent such as methanol, ethanol, isopropanol and the like or combinations thereof. In one embodiment, the solvent is methanol.

(iii) Halogenating the compound Formula (XXVII) to provide compound of Formula (II):

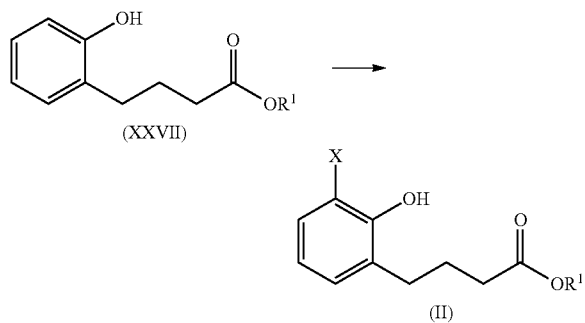

wherein X and $R^1$ are as defined above.

The regioselective o-halogenation of compound (XXVII) can be conducted using suitable halogenating reagents and conditions. In one embodiment, the ortho halogenation can be conducted using a N-halosuccinimide, such as N-chlorosuccinimide or N-bromosuccinimide in the presence of a secondary amine. Suitable secondary amines include, for example, dialkylamines. In some embodiments, the secondary amine is selected from dimethyl amine, diethylamine, diisopropylamine, dibutylamine, morpholine and piperidine, and the like or a combination of two or more thereof. Suitable solvents such as those listed herein may be employed for the halogenation reaction.

The halo compound, e.g., bromophenol-6-carbomethoxypropane may be synthesized from a-tetralone in three steps as shown in the following Scheme X.

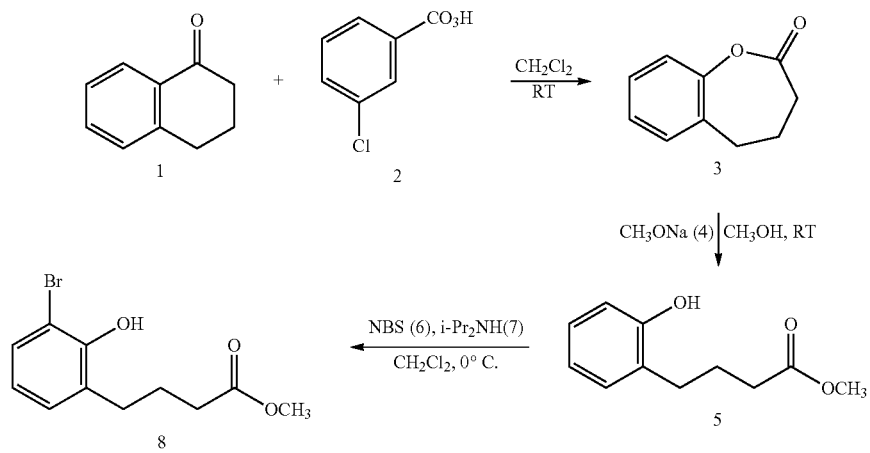

The Baeyer-Villiger oxidation of α-tetralone (1) with 3-chloroperbenzoic acid in dichloromethane at room temperature can produce benzolactone (3) in good yield. The opening of benzolactone (3) with sodium methoxide (4) in methanol at room temperature can afford methyl 4-((2-hydroxyphenyl)butanoate (5) in quantitative yield.

The regioselective ortho-bromination of methyl 4-(2-hydroxyphenyl)butanoate (5) with N-bromosuccinimide (NBS) in the presence of diisopropylamine (Reference for ortho-bromination: M. Dindarouglu, A. Falk and H. G. Schmalz, Synthesis, 2013, 45, 527-535) produced the desired 2-bromophenol-6-carbomethoxypropane (8) (90-93%) along with inseparable 2,4-dibromophenol-6-carbomethoxypropane (11) (7-10%) (Scheme IX). In order to improve the purity of the 2-bromo compound, the regioselective bromination of 4-(2-hydroxyphenyl)butanoate (5) with N-bromosuccinimide (NBS) and bromine in various solvents (THF, DMF, $CCl_4$, toluene, $CH_2Cl_2$ and DME) and temperatures (−78° C. to room temperature) was studied according to the following Scheme XI.

Scheme XI:

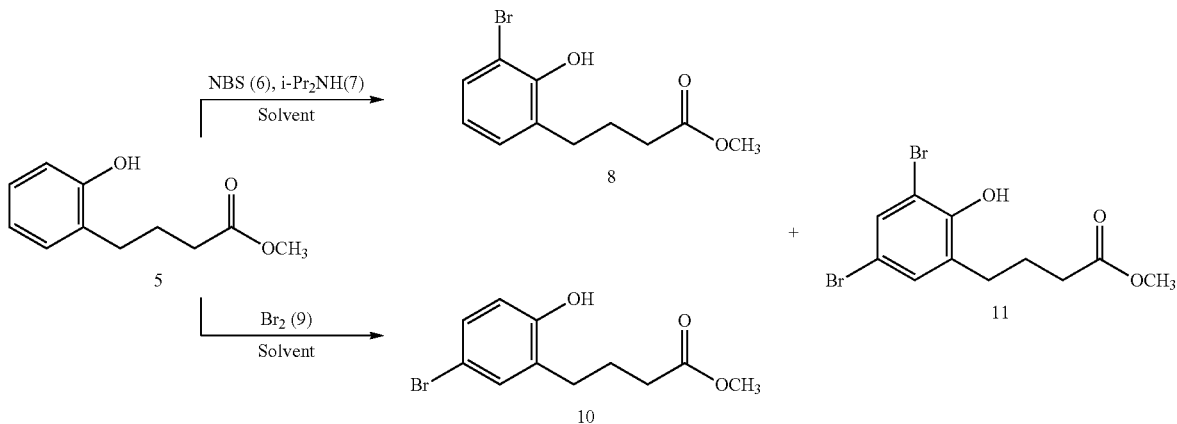

The bromination of 4-(2-hydroxyphenyl)butanoate (5) with NBS in THF gives a mixture of 2-bromo, 2,4-dibromo substituted products and unknown impurities (by $^1$H NMR) and in DMF does not produce any desired product, only starting material (by tlc). The NBS reaction of compound. (5) in 1,2-dimethoxyethane (DME) gives a mixture of 2-bromo, 4-bromo, 2,4-dibromo substitute side products and starting material. When the reaction is carried in CCl$_4$, toluene at 0° C. to RT, 2-bromo compound (8) is the major product (85-89%) and 4-bromo (10) (5-7%) and 2,4-dibromo (11) (5-7%) are the minor by products. In dichloromethane at 0° C., a mixture of 2-bromo (72.1%), 4-bromo (6.8%) and 2,4-dibromo compounds (21.1%) is formed and when the reaction is carried out at room temperature, more of 4-bromo and 2,4-dibromo compounds is observed (Entry 6, Table 1). But, when the bromination is carried out in the presence of diisopropylamine (DIPA) in toluene, CCl$_4$ and CH$_2$Cl$_2$ at 0° C., the yield of 2-bromo is improved to 92-97%. Bromination of compound (5) in CH$_2$Cl$_2$ and CCl$_4$) at lower temperature (−78° C. and −18° C. to 0° C.) did not improve the yield of desired 2-bromo compound (84-85%) and higher amounts of 2,4-dibromo compound (14-15%) was formed (Table 1). The bromination reactions on phenolic compound (5) are conducted with a few drops of cyclohexene (Entry 18) and 1.0 mL of cyclohexene (Entry 19) to avoid the formation of 2,4-dibromo compound. The results are reproduced in the following Table 1.

| Entry | Lot No. | Compd (5) (g) (eq) | DIPA (g) (eq) | NBS (g) (eq) | Solvent | Temp ° C. | Time hr | 2-Br (8) (%) | 4-Br (10) (%) | 2,4-DiBr (11) (%) |
|---|---|---|---|---|---|---|---|---|---|---|
| 1. | D-1135-040 | 0.103 (1.0) | No | 0.094 (1.0) | THF | RT | 0.5-19 | minor | No | major (by NMR) |
| 2. | D-1135-042 | 0.114 (1.0) | No | 0.105 (1.0) | DMF | RT | 0.5-19 | No | No | No SM only (by tlc) |
| 3. | D-1135-050 | 0.097 (1.0) | No | 0.08 (0.9) | CCl$_4$ | 0-RT | 0.5-2.5 | 89.1 | 5.2 | 5.7 |
| 4. | D-1135-052 | 0.093 (1.0) | No | 0.08 (0.9) | Toluene | 0-RT | 0.5-2.5 | 85.4 | 7.3 | 7.3 |
| 5. | D-1135-087 | 0.192 (1.0) | No | 0.170 (1.0) | DCM | 0 | 1.0 | 72.1 | 6.8 | 21.1 |
| 6. | D 1135-089 | 0.231 (1.0) | No | 0.210 (1.0) | DCM | RT | 1.0 | 66.0 | 8.7 | 25.3 |
| 7. | D-1135-044 | 0.187 (1.0) | 0.10 (1.0) | 0.154 (0.9) | DCM | 0 | 0.5 | 93.8 | 0.1 | 6.1 |
| 8. | D-1135-046 | 0.134 (1.0) | 0.16 (2.3) | 011 (0.9) | DCM | 0 | 0.5 | 97.1 | 0.1 | 2.8 |
| 9. | D-1135-048 | 0.154 (1.0) | 0.18 (2.2) | 0.126 (0.9) | CCl$_4$ | 0 | 0.5 | 96.8 | 0.1 | 3.1 |
| 10. | D-1135-054 | 0136 (1.0) | 0.251 (3.5) | 0.124 (1.0) | Toluene | 0 | 0.5 | 92.2 | 0.1 | 7.7 |
| 11. | D-1135-056 | 0.105 (1.0) | 0.251 (4.6) | 0.192 (2.0) | Toluene | 0 | 0.5 | 22.6 | 0.05 | 77.4 |
| 12. | D-1135-059 D-1135-059-A | 0.571 (1.0) | 0.297 (1.0) | 0.523 (1.0) | CCl$_4$ | 0 | 2.0 | 91.8 (c) 99.9 (p) | No | 8.2 (c) 0.1 (p) |
| 13. | D-1135-061 D-1124-040 | 0.574 (1.0) | 0.298 (1.0) | 0.525 (1.0) | Toluene | 0 | 2.0 | 91.6 (c) 95.9 (r) | 0.1 | 8.3 (c) 4.1 (r) |
| 14. | D-1135-063 | 0.375 (1.0) | 0.195 (1.0) | 0.344 (1.0) | DCM | 0 | 3.0 | 94.6 | 0.1 | 5.2 |
| 15. | D-1135-065 | 0.421 (1.0) | 0.219 (1.0) | 0.386 (1.0) | DCM | −78-0 | 3.0 | 84.0 | 0.2 | 15.8 |
| 16. | D-1135-067 | 0.416 (1.0) | 0.217 (1.0) | 0.381 (1.0) | CCl$_4$ | −18-0 | 3.0 | 85.3 | 0.6 | 14.1 |

-continued

| Entry | Lot No. | Compd (5) (g) (eq) | DIPA (g) (eq) | NBS (g) (eq) | Solvent | Temp °C. | Time hr | 2-Br (8) (%) | 4-Br (10) (%) | 2,4-DiBr (11) (%) |
|---|---|---|---|---|---|---|---|---|---|---|
| 17. | D-1135-069 | 0.494 (1.0) | 0.257 (1.0) | 0.452 (1.0) | Toluene | −78-0 | 3.0 | 82.9 | 0.4 | 16.7 |
| 18. | D-1135-081 | 0.169 (1.0) | 0.09 (1.0) | 0.15 (1.0) | DCM (a few drops of cyclohexene added) | 0 | 2 | 95.0 | 0.1 | 4.9 |
| 19. | D-1135-083 | 0.253 (1.0) | 0.33 (15) | 0.232 (1.0) | DCM (1.0 mL cyclohexene added) | 0 | 1 | 92.2 | 0.04 | 7.8 |
| 20. | D-1135-085 | 0.248 (1.0) | 0.33 (2.5) | 0.227 (1.0) | DCM (No cyclohexene added) | 0 | 1 | 91.4 | 0.06 | 8.5 |
| 21. | D-1135-121 | 0.435 (1.0) | 0.230 (1.0) | 0.399 (1.0) | DCM | 0 to 5 | 2 | 92.5 | No | 7.5 |
| 22. | D-1135-108 | 0.169 (1.0) | 0.155 (1.0) | 0.09 (1.0) | DME | 0 to RT | 7.5 | 58.5 | 1.6 | 39.8 |

The bromination of methyl 4-(2-hydroxypltenyl)butanoate (5) can also be conducted with bromine. The bromination of compound (5) with molecular bromine in various solvents (CCl$_4$ and CH$_2$Cl$_2$) at 0° C. exclusively produces the undesired 4-bromophenol-6-carbomethoxypropane (10) (91-97%) and very little 2-bromo compound (3-8%) (Entry 1 & 3, Table 2). With 2 equivalents of bromine a mixture of 4-bromo and 2,4-dibromo compounds (26.4 and 73.6% respectively) is observed (Entry 2). When the reaction is carried out in diethyl ether a mixture of 2-bromo, 4-bromo compounds and a major amount of unreacted starting material is obtained (Entry 4).

phenolic compound (5) (37.94 g) under the similar reaction condition only 67.0% of 2-bromo and 21.1% of 2,4-dibromo compounds are obtained (Entry 2). The crude bromo compound is recrystallized from cyclopentane/ethyl acetate (ratio: 100:1) at −40° C. to obtain the desired 2-bromo compound (8) in 95.1% pure and 22.5% yield (Entry 2). The pure phenolic compound (5) (30.0 g) is used for NBS-bromination under the similar reaction condition to afford 88.7% of 2-bromo and 6.9% of 2,4-dibromo compounds (Entry 3). The recrystallization of the crude bromo compound yields 2-bromo compound (8) in 94.75% purity. Further recrystal-

TABLE 2

Bromination of Methyl 4-(2-hydroxyphenyl)butanoate (5) with Bromine in Various Solvents

| Entry/ Lot No. | Compel (5) (g) (eq) | DIPA (g) (eq) | Br$_2$ (g) (eq) | Solvent | Temp °C. | Time hr | 2-Br (8) (%) | 4-Br (10) (%) | 2,4-DiBr (11) (%) |
|---|---|---|---|---|---|---|---|---|---|
| 1. D-1135-071 | 0.371 (1.0) | No | 0.30 (1.0) | DCM | 0 | 0.5-3.5 | 2.8 | 97.7 | 0.04 |
| 2. D-1135-073 | 0.715 (1.0) | No | 1.18 (2.0) | DCM | RT | 0.5-3.5 | No | 26.4 | 73.6 |
| 3. D-1135-075 | 0.050 (1.0) | No | 0.041 (1.0) | CCl$_4$ | 0 | 0.5 | 3.8 | 96.1 | 0.01 |
| 4. D-1135-077 | 0.071 (1.0) | No | 0 058 (1.0) | Et$_2$O | 0 | 0.5-2.5 | 8.5 | 91.5 | No |

Note:
The percentage ratio of 2-bromo, 4-bromo and 2,4-dibromo compounds were recalculated without unreacted starting material (5%, Entry 1 and 28%, Entry 4). With 2.0 eq of NBS, there was no starting material left (Entry 2).

It is observed that the bromination of 4-(2-hydroxyphenyl)butanoate (5) with NBS in the presence of diisopropylamine provides the desired 2-bromophenol-6-carbomethoxypropane (8) while with bromine it gives the undesired 4-bromophenol-6-carbomethoxypropane (10) only. Based on these results, the bromination of compound (5) was conducted in 7.1 g scale with NBS in the presence of diisopropylamine in dichloromethane at 0° C. to produce 86.8% of 2-bromo compound (8). The separation of 2-bromo and 2,4-dibromo compound by column chromatography can be difficult due to close R$_f$ on tlc of these compounds. The crystallization of the crude bromo compound with cyclopentane/ethyl acetate (ratio: 100: 1) improved the purity to 94% and yield 61.1% (Entry 1, Table 3). When the NBS-bromination is carried out on crude lization of compound gives pure 2-bromo compound (8) in 97.1% and 61.4% yield (Entry 3).

TABLE 3

HPLC of 2-Bromophenol-6-carbomethoxypropane

| Entry. | Lot No. | Starting Material (5) (%) | 2-Br (8) (%) | 4-Br (10) (%) | 2,4-DiBr (11) (%) |
|---|---|---|---|---|---|
| 1. | D-1135-091 (Compound 5 was purified) | 3.95 | 86.78 | 0.08 | 8.01 |
|  | D-1124-041 (recrystallization) | 1.11 | 94.03 | No | 4.30 |

TABLE 3-continued

HPLC of 2-Bromophenol-6-carbomethoxypropane

| Entry. | Lot No. | Starting Material (5) (%) | 2-Br (8) (%) | 4-Br (10) (%) | 2,4-DiBr (11) (%) |
|---|---|---|---|---|---|
| 2. | D-1135-110 (Compound 5 was not purified) | 4.54 | 67.01 | 0.15 | 21.08 |
|  | D-1124-043 (recrystallization) | 0.34 | 95.15 | No | 4.36 |
| 3. | D-1135-123 (Compound 5 was purified) | 3.71 | 88.69 | 0.07 | 6.91 |
|  | D-1135-127 (1st recrystallization) | 1.04 | 94.75 | No | 3.73 |
|  | D-1135-127-P (2nd recrystallization) | 0.46 | 97.12 | No | 1.99 |

Following the above procedure, 2-bromophenol-6-carbomethoxypropane (8) is synthesized from α-tetralone (1) in three steps with a purity of 96-97% and having less than 2% of 2,4-dibromo-6-carbomethoxypropane (11).

The 2,4-dibromophenol-6-carbomethoxypropane (11) can be synthesized as a reference impurity marker for the radical cyclization synthesis of Beraprost according to the following Scheme XII.

Scheme XII: Synthesis of 2,4-Dibromophenol-6-carbomethoxypropane (11)

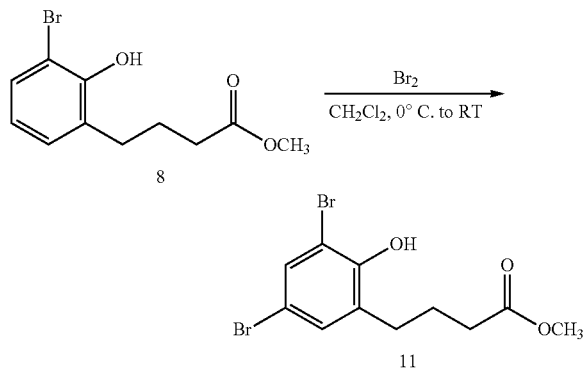

The 2-bromophenol-6-carbomethoxypropane (8) (90% pure) is brominated with bromine in dichloromethane at 0° C. at room temperature to provide 2,4-dibromophenol-6-carbomethoxypropane (11). The crude dibromo compound is recrystallized from hexane and ethyl acetate to afford pure 2,4-dibromo compound in 47.1% yield with purity of 93.7% by HPLC.

Beraprost prepared by the methods described herein can be converted in to its pharmaceutically acceptable salts using the methods known in the art. The salts can be produced before or after the isolation of Beraprost. Thus in one embodiment, the salts of compound of Formula (I) can be prepared by reacting it with various bases. For example, the sodium salt of Beraprost can be prepared by reacting it with sodium hydroxide. As used herein, a "pharmaceutically acceptable salt" refers to a salt that is useful in preparing a pharmaceutical composition and is generally safe, non-toxic and neither biologically nor otherwise undesirable pharmaceutical use.

Compounds with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts), alkaline earth metal salts (such as magnesium and calcium salts) and salts formed with amine containing compounds such as triethylamine, diethanolamine, triethanolamine, choline, glucosamine, ethylenediamine, L-lysine and L-arginine.

In one embodiment, Beraprost prepared according to the methods described herein has at least 70%, 80%, 90%, 95%, 97%, 98%, 99%, 99.5%, 99.9% or 100% chiral purity.

Beraprost prepared by the methods described herein may be used, in a pharmaceutical formulation for treating a number of conditions by administering to a subject, such as a human being in need thereof. For example, Beraprost may be used for treating a condition, for which Beraprost is known to be effective. Conditions, for which Beraprost is known to be effective, include but not limited to pulmonary hypertension (including primary and secondary pulmonary hypertension and pulmonary arterial hypertension), peripheral vascular disease, severe intermittent claudication, critical limb ischemia, ischemic lesions, asthma, pulmonary fibrosis, diabetic neuropathic foot ulcers, interstitial lung disease.

The invention also includes pharmaceutical formulations comprising Beraprost prepared by the methods described herein. A pharmaceutical formulation may comprise Beraprost, and a pharmaceutically acceptable carrier or excipient. The term "pharmaceutical" when used herein as an adjective means substantially non-deleterious to the recipient mammal. By "pharmaceutical formulation" it is meant the carrier, diluent, excipients and active ingredient(s) must be compatible with the other ingredients of the formulation, and not deleterious to the recipient thereof Beraprost prepared by the methods described herein can be Formulated prior to administration. The selection of the formulation should be decided by the attending physician taking into consideration the same factors involved with determining the effective amount.

Liquid dosage forms for oral administration of a Beraprost, include solutions, emulsions, suspensions, syrups and elixirs, which may be Formulated prior to administration.

The total active ingredients in such formulations comprises from 0.1% to 99.9% by weight of the formulation. Beraprost, can be Formulated with one or more additional active ingredients or as the sole active ingredient.

Pharmaceutical formulations of the present invention are prepared by procedures known in the art using well known and readily available ingredients. For example, Beraprost, either alone, or in combination with other active ingredient(s) are Formulated with common excipients, diluents, or carriers, and formed into tablets, capsules, suspensions, solutions, injectables, aerosols, powders, and the like.

Pharmaceutical formulations of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral formulations may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, Beraprost, is mixed with at least one inert, pharmaceutical carrier such as sodium citrate, or dicalcium phosphate, and/or (a) fillers or extenders such as starches, sugars including lactose and glucose, mannitol, and silicic acid, (b) binding agents such as carboxymethyl-cellulose and other cellulose derivatives, alginates, gelatin, poly(vinylpyrrolidine), sucrose and acacia, (c) humectants such as glycerol, (d) disintegrating agents such as agar-agar, calcium carbonate, sodium bicarbonate, potato or tapioca starch, alginic acid, silicates and sodium carbonate, (e) moisturizing agents such as glycerol; (f) solution retarding agents such as paraffin, (g) absorption accelerating agents such as quaternary ammonium compounds, (h) wetting agents such as cetyl alcohol and glycerin monostearate, (i) absorbents such as kaolin and bentonite clay, and (j) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid formulations of a similar type may also comprise the fill in soft or hard gelatin capsules using excipients such as lactose as well as high molecular weight poly(ethylene glycols) and the like. Solid dosage forms such as tablets, dragees, capsules, pills and granules can also be prepared with coatings or shells such as enteric coatings or other coatings well known in the pharmaceutical Formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract. The active ingredient(s) may also be microencapsulated in a sustained-release coating, with the microcapsules being made part of a pill of capsule formulation.

Liquid dosage forms for oral administration of Beraprost include solutions, emulsions, suspensions, syrups and elixirs, which may be Formulated from the particular polymorphic form prior to administration. In addition to the active components, liquid formulations may include inert diluents commonly used in the art such as water or other pharmaceutical solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof. Besides inert diluents, the liquid oral formulations may also include adjuvants such as wetting agents, emulsifying and suspending agents, and sweetening, flavoring, and perfuming agents. Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

All patents, patent applications, publications and references cited herein are incorporated by reference in their entirety to the extent as if they were individually incorporated by reference. The invention is further illustrated by, though in no way limited to, the following examples.

EXAMPLES

Example 1

Preparation of Phosphonate Compound (X)

The ketophosphonate intermediate (X), i.e., (S)-Dimethyl-(3-methyl-2-oxohept-5-yn-1-yl)phosphonate(8) can be synthesized as follows.

(A) Synthesis of N-((1R,2R)-1-hydroxy-1-phenyl-propan-2-yl)-N-methylpropionamide (3)

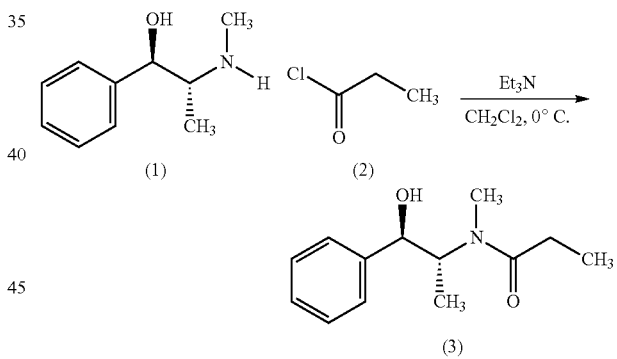

| Name | Amount | mmol | Eq. |
|---|---|---|---|
| (1R,2R)-Pseudoephedrine (1) | 10.19 g | 61.67 | 1.00 |
| Propionyl chloride | 6.85 g | 74.03 | 1.20 |
| Triethylamine | 8.74 g | 86.37 | 1.40 |
| Dichloromethane (anhydrous) | 90 mL | NA | NA |

To a solution of (1R,2R)-2-(methylamino)-1-phenylpropan-1-ol [(1R,2R)-pseudoephedrine] (10.19 g, 61.67 mmol) in anhydrous dichloromethane (70 mL) was added triethylamine (8.74 g, 86.37 mmol) at room temperature. The clear solution was cooled to 0° C. and then added a solution of propionyl chloride (6.85 g, 74.03 mmol) in anhydrous dichloromethane (20 mL) under argon over a period of 10 min. The reaction mixture was stirred at 0° C. for 2 h. The reaction mixture was quenched with water and then removed dichloromethane in vacuo. The aqueous residue was extracted with tent-butyl methyl ether (MTBE). The combined organic extracts were washed with water, 10% hydrochloric acid, water, saturated sodium bicarbonate, brine, dried (Na$_2$SO$_4$), filtered and concentrated in vacuo to give propionamide (3) as white solid (13.52 g, 99%). The (1R, 2R)-pseudoephedrine propionamide or N-((1R,2R)-1-hydroxy-1-phenylpropan-2-yl)-N-methylpropionamide (3) is also available commercially in small quantities.

(B) Synthesis of (S)—N-(1R,2R)-1-hydroxy-1-phenylpropan-2-yl)-N,2-dimethylhex-4-ynamide (4).

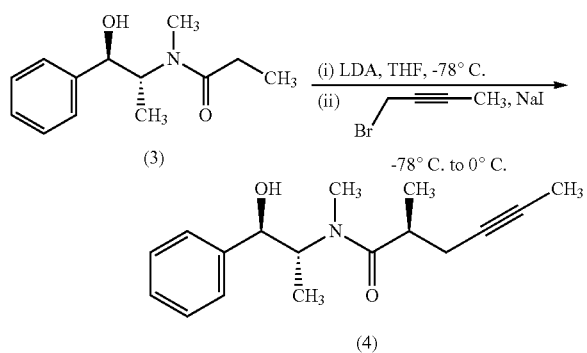

(3)

(4)

| Name | Amount | mmol | Eq. |
|---|---|---|---|
| (1R,2R)-Pseudoephedrine-propionamide (3) | 18.1 g | 81.79 | 1.00 |
| Lithium chloride (anhydrous) | 20.80 g | 490.68 | 6.00 |
| Diisopropylamine | 18.62 g | 184.01 | 2.25 |
| n-Butyllithium (1.6M in hexane) | 107.4 mL | 171.84 | 2.01 |
| 1-Bromo-2-butyne | 21.75 g | 163.55 | 2.00 |
| Sodium iodide | 24.52 g | 163.59 | 2.00 |
| Tetrahydrofuran (anhydrous) | 230 mL | NA | NA |

To a suspension of anhydrous lithium chloride (18.09 g, 426.75 mmol) and diisopropylamine (16.18 g, 159.90 mmol) in anhydrous tetrahydrofuan (50 mL) at −78° C. under argon was added n-butyllithium in hexane (1.6 M) (93.3 mL, 149.26 mmol). The resulting suspension was stirred at −78° C. for 15 min, at 0° C. for 5 min and then cooled back to −78° C. Then, an ice-cold solution of propionamide (3) (15.73 g, 71.08 mmol) in anhydrous tetrahydrofuran (100 mL) was added to the suspension over a period of 15 minutes. After complete addition, the reaction mixture was stirred at −78° C. for 2 h, at 0° C. for 15 min, at ambient temperature for 5 min and finely cooled to 0° C. In a separate flask, 1-iodo-2-butyne in tetrahydrofuran was prepared in situ by stirring a mixture of 1-bromo-2-butyne (18.90 g, 142.11 mmol) and sodium iodide (21.31 g, 142.17 mmol) in anhydrous tetrahydrofuran (50 mL) ambient temperature under argon for 2 h. The mixture was filtered and the filtrate was added slowly to the reaction mixture at 0° C. over a period of 15 min. After complete addition, the reaction mixture was stirred at 0° C. for 1 h. The reaction mixture was quenched at 0° C. with saturated ammonium chloride. The organic layer was separated and the aqueous layer was extracted with ethyl acetate. The combined organic extracts were washed with brine, dried (Na$_2$SO$_4$), filtered and concentrated in vacuo to give viscous liquid. The chromatography of crude product using a mixture of ethyl acetate in hexanes (10-50%) gave pure methyl hexynamide (4) as pale yellow viscous liquid (12.36 g, 63.6% and chiral purity, 97.6%). FT-IR (ATR) v, 3436 (w), 1636 (s), 1063 (s) cm$^{-1}$; $^1$H NMR, (3:2 rotamer ratio, (acetone-d$_6$, 300 MHz): δ 7.38 (m, 5H), 4.91, 4.57, 4.58 (br d, J=8.5 Hz, 1H), 4.13, 3.98 (two m, 1H), 3.70, 3.66 (two m, 1H), 2.93, 2.86 (two s, 3H), 1.02, 1.00 (two d, J=7.4 Hz, 3H), 0.96, 0.86 (two d, J=6.9 Hz, 3H); $^{13}$C NMR (acetone-d$_6$, 75 MHz): δ 173.06, 172.79, 139.54, 139.24, 128.63, 128.42, 128.37, 128.12, 127.98, 82.12, 81.85, 80.78, 80.69, 75.20, 74.92, 56.30, 55.61, 55.53, 26.67, 26.03, 15.14, 13.80, 9.15, 8.84, 2.44; MS (ESI, 75 eV) m/z: 296.27 (M+Na)$^+$; Anal. Calcd for C$_{17}$H$_{23}$N$_2$: C, 74.69; H, 8.56, N, 5.12; Found: C, 74.38; H, 8.56; N, 5.09.

(C) Synthesis of (1R,2R)-2-((S)—N,2-dimethylhex-4-ynamido)-1-phenylpropyl acetate (5).

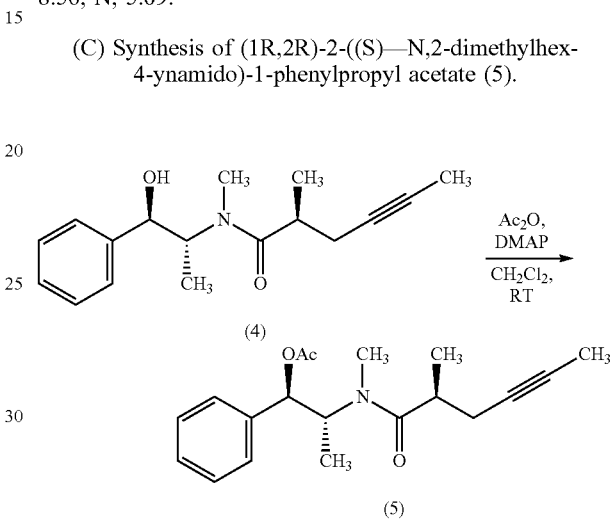

(4)

(5)

| Name | Amount | mmol | Eq. |
|---|---|---|---|
| (1R,2R)-Pseudoephedrine methyl-hexynamide (4) | 21.80 g | 79.75 | 1.00 |
| 4-(Dimethylamino)pyridine | 19.49 g | 159.53 | 2.00 |
| Acetic anhydride | 16.28 g | 159.31 | 2.00 |
| Dichloromethane (anhydrous) | 300 mL | NA | NA |

To a solution of methyl hexynamide (4) (21.8 g, 79.75 mmol) in anhydrous dichloromethane (300 mL) was added 4-(dimethylamino)pyridine (DMAP) (19.49 g, 159.53 mmol) followed by acetic anhydride (16.28 g, 159.31 mmol) under argon at ambient temperature. The reaction mixture was stirred at ambient temperature overnight. The mixture was evaporated in vacuo to remove dichloromethane and the residue was treated with water and ethyl acetate. The organic layer was separated and the aqueous layer was extracted with ethyl acetate. The combined organic extracts were washed with water, saturated sodium bicarbonate, water, 0.1 N hydrochloric acid, water, brine, dried (Na$_2$SO$_4$), filtered and concentrated in vacuo to give light yellow viscous liquid. The crude product was crystallized twice with heptanes to give pure methyl hexynamide acetate (5) as white crystals (18.14 g, 72.1%, chiral purity, 99.7%) (mp 78-79° C.; HPLC, chiral purity, 99.71% (99.13% de); FT-IR (ATR) v, 1734 (s), 1627 (s), 1244 (s), 1023 (s) cm$^{-1}$; $^1$H NMR, (2:1 rotamer ratio, (acetone-d$_6$, 300 MHz): δ 7.37 (m, 5H), 5.82 (two merged d, 1H), 5.17, 4.38 (two m, 1H), 2.99, 2.77 (two s, 3H), 2.88 (m, 1H), 2.37-2.09 (m, 2H), 2.01, 2.97 (two s,3H), 1.74, 1.70 (two t, J=2.5 Hz, 3H), 1.11, 1.03 (two d, J=3.3 Hz, J=6.9 Hz, 3H), 1.08, 0.92 (two d, J=3.0 Hz, J=7.1

Hz, 3H); $^{13}$C NMR (acetone-$d_6$, 75 MHz): δ 174.98, 174.91, 169.25, 169.03, 138.83, 138.38, 128.66, 128.47, 128.22, 127.55, 127.42, 77.72, 77.34, 75.84, 55.29, 51.37, 35.97, 35.79, 26.74, 23.12, 22.92, 20.22, 20.09, 17.21, 16.76, 14.92, 13.73, 2.62, 2.40; MS (ESI, 75 eV) m/z: 338.0 (M+Na)$^+$; Anal. Calcd for $C_{19}H_{25}N_2O_3$: C, 72.35; H, 7.99, N, 4.44; Found: C, 72.51; H, 7.88; N, 4.55.

(D) Synthesis of (S)-2-methylhex-4-ynoic acid (6).

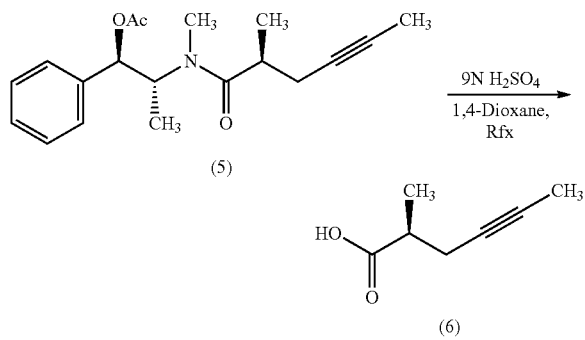

| Name | Amount | mmol | Eq. |
|---|---|---|---|
| (1R,2R)-Pseudoephedrine methyl-hexynamide acetate (5) | 18.0 g | 57.07 | 1.00 |
| Sulfuric acid (9N) | 8.0 mL | NA | NA |
| 1,4-Dioxane | 5.0 mL | NA | NA |

To a solution of (1R,2R)-pseudoephedrine methyl hexynamide acetate (5) (18.0 g, 57.07 mmol) in 1,4-dioxane (80 mL) was added 9 N sulfuric acid (80 mL) at ambient temperature. The reaction mixture was gently heated to reflux for 2 h. The reaction mixture was cooled to room temperature and then added water. The mixture was extracted with tent-butyl methyl ether (MTBE). The MTBE extracts were washed with water, brine, dried ($Na_2SO_4$), filtered and concentrated in vacuo to give (S)-2-methylhex-4-ynoic acid (6) as clear colorless liquid (7.2 g, quantitative, chiral purity, 98.63%). FT-IR (ATR) ν, 1702 (s) cm$^{-1}$; $^1$H NMR, (CDCl$_3$, 300 MHz): δ 11.36 (br s, 1H), 2.62 (m, 1H), 2.52-2.26 (m, 2H), 1.76 (t, J=2.7 Hz, 3H), 1.26 (d, J=6.9 Hz, 3H); $^{13}$C NMR (CDCl$_3$, 75 MHz): δ 181.56, 76.75, 75.83, 39.05, 22.72, 16.16, 3.44.

(E) Synthesis of (S)—N-methoxy-N,2-dimethylhex-4-ynamide (7)

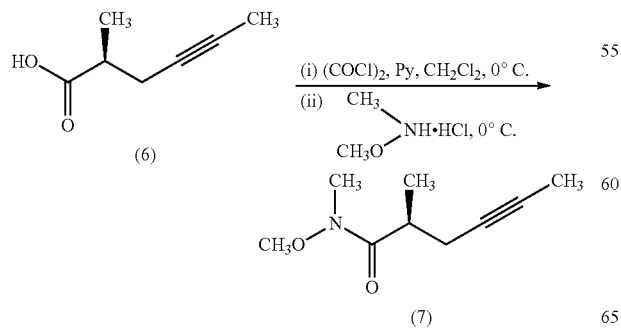

| Name | Amount | mmol | Eq. |
|---|---|---|---|
| (S)-2-Methyl-hex-4-ynoic acid (6) | 7.10 g | 56.38 | 1.00 |
| Oxalyl chloride (2.0M in dichloromethane) | 34.00 mL | 68.00 | 1.21 |
| N,N-Dimethyformamide (anhydrous) | 0.021 g | 0.29 | 0.005 |
| N,O-Dimethylhydroxylamine hydrochloride | 8.23 g | 84.38 | 1.50 |
| Pyridine | 13.35 g | 168.77 | 3.00 |
| Dichloromethane (anhydrous) | 130 mL | NA | NA |

To a solution of (S)-2-methyl hex-4-ynoic acid (6) (7.1 g, 56.28 mmol) in anhydrous dichloromethane (40 mL) was added oxalyl chloride in dichloromethane (2.0 M) (34.0 mL, 68.00 mmol) followed by anhydrous N,N-dimethylformamide (0.021 g, 0.29 mmol). The reaction mixture was stirred under argon at ambient temperature for 2 h and then cooled to 0° C. This cold solution was transferred via cannula into the clear solution of N,O-dimethylhydroxylamine hydrochloride (8.23 g, 84.38 mmol) and pyridine (13.35 g, 13.65 mmol) in anhydrous dichloromethane (90 mL) at 0° C. under argon. The reaction mixture was stirred at 0° C. for 1 h. The reaction mixture was quenched at 0° C. with saturated ammonium chloride and then removed dichloromethane in vacuo. The residue was stirred with water and tent-butyl methyl ether (MTBE). The organic layer was separated and the aqueous layer was extracted with MTBE. The combined MTBE extracts were washed with water, brine, dried ($Na_2SO_4$), filtered and concentrated in vacuo to give yellow liquid (9.35 g). The chromatography of crude product using a mixture of ethyl acetate in hexane (5-30%) gave pure (S)-N-methoxy-N,2-dimethylhex-4-ynamide(7) as pale yellow liquid (7.90 g, 82.9% and chiral purity, 99.7%). FT-IR (ATR) ν, 1659 (s) cm$^{-1}$; $^1$H NMR, CDCl$_3$, 300 MHz): δ 3.69, (s, 3H), 3.17 (s, 3H), 3.01 (m, 1H), 2.42, 2.18 (two m, 2H), 1.73 (t, J=2.5 Hz, 3H), 1.14 (d, J=6.9 Hz, 3H); $^{13}$C NMR (CDCl$_3$, 75 MHz): δ 176.52, 77.23, 76.72, 61.62, 35.61, 32.26, 23.06. 17.06, 3.57; MS (ESI, 75 eV) m/z: 170.15 (M+H)$^+$, 192.16 (M+Na)$^+$.

(F) Synthesis of (S)-dimethyl (3-methyl-2-oxohept-5-yn-1-yl) phosphonate (8)

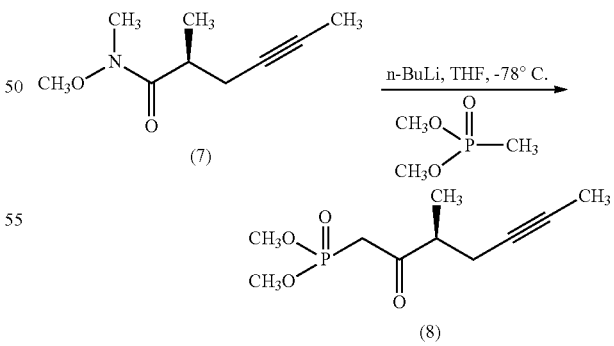

| Name | Amount | mmol | Eq. |
|---|---|---|---|
| (S)-N-Methoxy-N,2-dimethylhex-4-ynamide(7) | 7.80 g | 46.09 | 1.00 |

| Name | Amount | mmol | Eq. |
|---|---|---|---|
| n-Butyllithium (1.6 M in hexane) | 58.0 mL | 91.80 | 2.01 |
| Dimethyl methylphosphonate | 14.30 g | 115.25 | 2.50 |
| Tetrahydrofuran (anhydrous) | 170 mL | NA | NA |

To a solution of dimethyl methylphosphonate (14.30 g, 115.25 mmol) in anhydrous tetrahydrofuran (120 mL) at −78° C. under argon was added slowly a solution of n-butyllithium in hexane (1.6 M) (58 mL, 92.80 mmol) over a period of 20 min. The reaction mixture was stirred at −78° C. for 15 min and then a solution of (S)—N-methoxy-N,2-dimethylhex-4-ynamide(7) (7.80 g, 46.09 mmol) in anhydrous tetrahydrofuran (50 mL) was added over a period of 30 min. The reaction was stirred at −78° C. for 3 h. The reaction mixture was quenched at −78° C. with saturated ammonium chloride (120 mL) and then the mixture was allowed to warm to room temperature. The mixture was evaporated in vacuo to remove tetrahydrofuran. The residue was treated with water and then extracted with tert-butyl methyl ether (MTBE). The combined MTBE extracts were washed with water, brine, dried ($Na_2SO_4$), filtered and concentrated in vacuo to give a liquid (12.78 g). The chromatography of crude product using a mixture of ethyl acetate in hexane (20-90%) gave pure (S)-3-methyl-2-oxo-hept-5-ynylphosphonic acid dimethyl ester (8) as a pale yellow liquid (9.55 g, 89.2%, chiral purity, 99.14%). FT-IR (ATR) v, 1711 (m), 1252 (m), 1016 (s) $cm^{-1}$; $^1H$ NMR, $CDCl_3$, 300 MHz): δ 3.78, 3.75 (two s, 2×3H), 3.21, 3.13 (dd, J=7.1 Hz, J=22.3 Hz, 3H), 2.88 (m, 1H), 2.41-2.21 (m, 2H), 1.73 (t, J=2.5 Hz, 3H), 1.15 (d, 3H); $^{13}C$ NMR ($CDCl_3$, 75 MHz): δ 204.48, 204.39, 77.74, 76.07, 53.18, 53.13, 53.09, 53.05, 46.56, 40.97, 39.25, 22.30, 15.85, 3.53; MS (ESI, 75 eV) m/z: 232.9 $(M+H)^+$, 254.9 $(M+Na)^-$.

(G) Synthesis of diethyl methyl-(2-butynyl)malonate (16)

Method A:

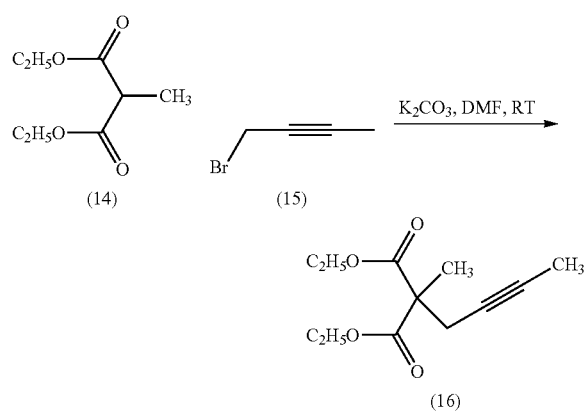

| Name | Amount | mmol | Eq. |
|---|---|---|---|
| Diethyl methylmalonate (14) | 10.15 g | 58.27 | 1.0 |
| Potassium carbonate (powder) | 16.11 g | 116.56 | 2.0 |
| 1-Bromo-2-butyne (15) | 10.85 g | 81.58 | 1.4 |
| N,N-Dimethylfomamide (DMF) | 75 mL | NA | NA |

To a solution of diethyl methylmalonate (14) (10.15 g, 58.27 mmol) in anhydrous N,N-dimethylformamide (60 mL) was added powdered potassium carbonate (12.08 g, 87.40 mmol) followed by 1-bromo-2-butyne (15) (8.52 g, 64.06 mmol) in N,N-dimethylformamide (15 mL). The reaction mixture was stirred under nitrogen at room temperature overnight. After 21h, the reaction mixture was checked by tlc (EtOAc/Hexane, 1:4). The reaction was not complete, an additional powdered potassium carbonate (4.03 g, 29.16 mmol) (total amount was 16.11 g, 116.56 mmol) and 1-bromo-2-butyne (15) (2.33 g, 17.52 mmol) (total amount was 10.85 g, 81.58 mmol) were added. The reaction mixture was stirred at room temperature for 3 h and checked by tlc (EtOAc/Hexane, 1:4) and there was some starting material left. The reaction was continued to stir at room temperature. After 68 h, the reaction was checked by tlc and found complete. The reaction mixture was poured into the ice-water (100 mL) and stirred for 15 minutes. The mixture was extracted with tent-butyl methyl ether (MTBE). The combined MTBE extracts were washed with saturated ammonium chloride, brine, dried ($Na_2SO_4$), filtered and the filtrate was concentrated in vacuo to give diethyl methyl-(2-butynyl)malonate (16) as a pale yellow liquid (13.66 g, 104%). The crude product was characterized by spectral data ($^1H$ NMR) and used in the next step without further purification.

Method B:

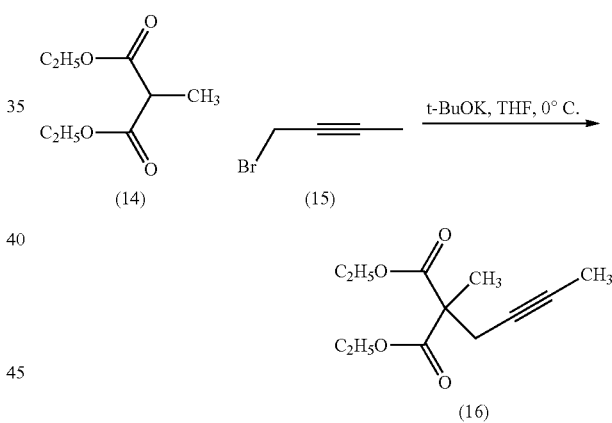

| Name | Amount | mmol | Eq. |
|---|---|---|---|
| Diethyl methylmalonate (14) | 1.04 g | 5.97 | 1.0 |
| Potassium tert-butoxide | 0.81 g | 7.22 | 1.21 |
| 1-Bromo-2-butyne (15) | 0.95 g | 7.14 | 1.19 |
| Tetrahydrofuran | 20 mL | NA | NA |

To a solution of diethyl methylmalonate (14) (1.04 g, 5.97 mmol) in anhydrous tetrahydrofuran (15 mL) at 0° C. (ice/water bath) under nitrogen was added powdered tert-butoxide (0.81 g, 7.22 mmol) followed by drop-wise addition of 1-bromo-2-butyne (15) (0.95 g, 7.14 mmol) in anhydrous tetrahydrofuran (5 mL). After complete addition, the reaction mixture was stirred at 0° C. for 30 minutes. The reaction mixture was checked by tlc (EtOAc/Hexane, 1:4)

and found complete. The mixture was quenched with brine (15 mL) and separated the layers. The aqueous layer was extracted with ethyl acetate. The combined organic layers were washed with brine (1×10 mL), filtered and the filtrate was concentrated in vacuo to give diethyl methyl-(2-butynyl)malonate (16) as a colorless liquid (1.36 g, 100%). The product was characterized by spectral data ($^1$H NMR) and used in the step without further purification.

In conclusion, the Method B was better than Method A. In Method B, the C-alkylation diethyl methylmalonate (14) with 1-bromo-2-butyne (15) was faster than in Method A, and the simple aqueous work up gave pure diethyl methyl-(2-butynyl)malonate (16).

(H) Synthesis of racemic ethyl 2-methylhex-4-ynoate (17)

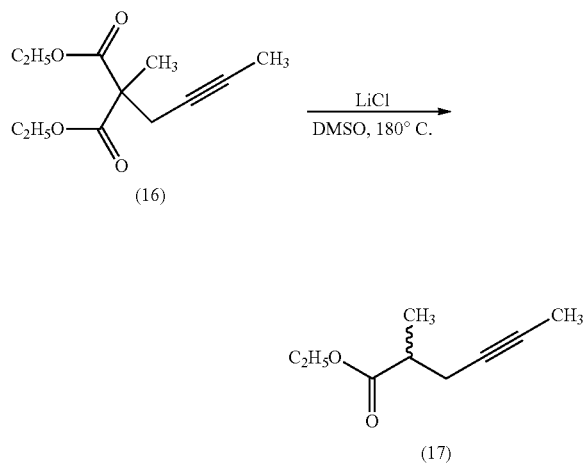

| Name | Amount | mmol | Eq. |
|---|---|---|---|
| Diethyl methyl-(2-butynyl) malonate (16) | 13.1 g | 57.90 | 1.0 |
| Lithium chloride | 2.94 g | 69.35 | 1.2 |
| Dimethyl sulfoxide | 30 mL | NA | NA |
| Water | 0.5 mL | NA | NA |

To a solution of diethyl methyl-(2-butynyl)malonate (16) (crude, 13.65 g, calculated as 13.1 g, 57.90 mmol) in anhydrous dimethyl sulfoxide (30 mL) was added lithium chloride (2.94 g, 69.35 mmol) and water (0.5 mL). The reaction mixture was heated to 180° C. under argon for 2.5 h. After 2.5 h, the reaction mixture was checked by tlc (EtOAc/Hexane, 1:4) and found complete. The mixture was poured into ice/water (150 mL) and then extracted with tent-butyl methyl ether (MTBE). The combined MTBE extracts were washed with water, brine, dried (Na$_2$SO$_4$), filtered and the filtrate was concentrated in vacuo to give dark yellow liquid (6.30 g). The chromatography of the crude product in silica gel (210 g) using ethyl acetate in hexanes (5-15%) gave pure racemic ethyl 2-methylhex-4-ynoate (17) as a pale yellow liquid (5.76 g, 64.5%). The pure product was characterized by spectral data ($^1$H NMR).

(I) Synthesis of racemic N-methoxy-N,2-dimethylhex-4-ynamide (18)

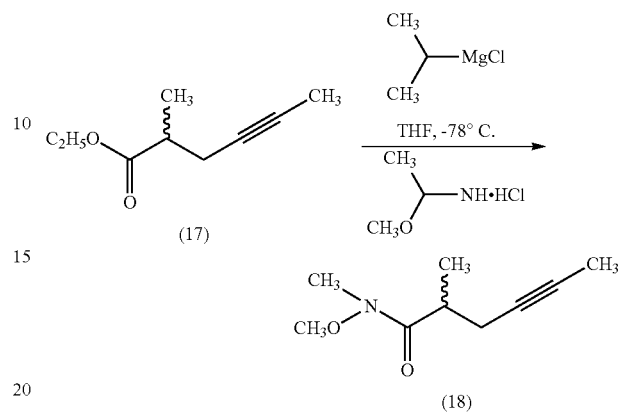

| Name | Amount | mmol | Eq. |
|---|---|---|---|
| Racemic Ethyl 2-methyl-hex-4-ynoate (17) | 1.09 g | 7.07 | 1.0 |
| N,O-Dimethylhydroxylamine hydrochloride | 1.07 g | 10.97 | 1.55 |
| Isopropylmagnesium chloride (2.0 M in THF) | 11.0 mL | 22.00 | 3.11 |
| Tetrahydrofuran (anhydrous) | 15 mL | NA | NA |

To a solution of racemic ethyl2-methyl-hex-4-ynoate (17) (1.09, 7.07 mmol) in anhydrous tetrahydrofuran (15 mL) was added N,O-dimethylhydroxylamine hydrochloride (1.07 g, 10.97 mmol) under argon. To this suspension of mixture was added isopropylmagnesium chloride in tetrahydrofuran (2.0 M, 11.0 mL, 22.0 mmol) at −20° C. under argon over a period of 30 min. After complete addition, the reaction mixture was stirred at −20° C. for 30 min and checked tlc (EtOAc/Hexane, 1:1). The reaction mixture was allowed to warm to room temperature and quenched with saturated ammonium chloride solution (10 mL). The mixture was diluted with ethyl acetate (15 mL) and water (10 mL). The organic layer was separated and the aqueous layer was extracted with ethyl acetate. The combined ethyl acetates were washed with brine, dried (Na$_2$SO$_4$), filtered and concentrated in vacuo to give pale yellow liquid (1.21 g). The crude product (18) was characterized by spectral data ($^1$H NMR) and used in the next step without further purification.

(J) Synthesis of racemic dimethyl-(3-methyl-2-oxo-hept-5-yn-1-yl)-phosphonate(20)

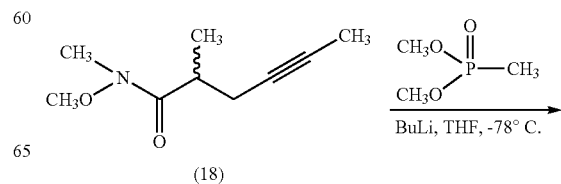

-continued

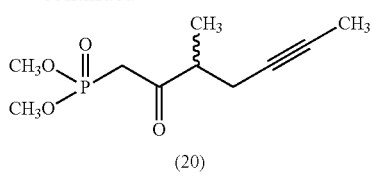

(20)

| Name | Amount | mmol | Eq. |
|---|---|---|---|
| Racemic N-Methoxy-N,2-dimethylhex-4-ynamide(18) | 1.20 g | 7.09 | 1.00 |
| n-Butyllithium (1.6 M in hexane) | 8.90 mL | 14.24 | 2.00 |
| Dimethyl methylphosphonate | 2.20 g | 17.73 | 2.50 |
| Tetrahydrofuran (anhydrous) | 20.0 mL | NA | NA |

To a solution of dimethyl methylphosphonate (2.20 g, 17.73mmol) in anhydrous tetrahydrofuran (20 mL) at −78° C. under argon was added slowly a solution of n-butyllithium in hexane (1.6M) (8.9 mL, 14.24 mmol) over a period of 20 min. The reaction mixture was stirred at -78° C. for 15 min and then a solution of racemic N-methoxy-N,2-dimethylhex-4-ynamide(18) (1.20 g, 7.09mmol) in anhydrous tetrahydrofuran (10 mL) was added over a period of 15 min. The reaction was stirred at −78° C. for 2 h and checked by tlc (EtOAc/Hexane, 7:3). The reaction mixture was quenched at −78° C. with saturated ammonium chloride (10 mL) and then the mixture was allowed to warm to room temperature. The mixture was separated and the aqueous layer was extracted with ethyl acetate. The combined ethyl acetate extracts were washed with water, brine, dried (Na₂SO₄), filtered and concentrated in vacuo to give a pale yellow liquid (2.16 g). The chromatography of crude product in silica gel (90.8 g) using a mixture of ethyl acetate in hexane (20-90%) gave pure racemic dimethyl-(3-methyl-2-oxohept-5-yn-1-yl)-phosphonate(20) as a pale yellow liquid (1.24 g, 75.1%). The pure product was characterized by spectral data ($^1$H NMR, $^{13}$C NMR) and purity by HPLC.

(K) Synthesis of methyl-(2-butynyl)malonic acid (19)

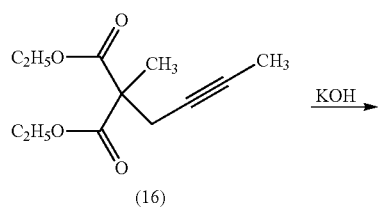

| Name | Amount | mmol | Eq. |
|---|---|---|---|
| Diethyl methyl-(2-butynyl)malonate (16) | 0.76 g | 3.36 | 1.00 |
| Potassium hydroxide | 0.48 g | 8.55 | 2.54 |
| Ethyl alcohol | 2.5 mL | NA | NA |
| Water | 0.5 mL | NA | NA |

To a solution of diethyl methyl-(2-butynyl)malonate (16) (0.76 g, 3.36mmol) in ethyl alcohol (2.5 mL) was added slowly a solution of potassium hydroxide (0.48 g, 8.55 mmol) in water (5 mL) at room temperature. The reaction mixture was gently heated to reflux for 2.5 h and then checked tlc (EtOAc/Hexane, 1:4 and EtOAc, 100%). The reaction was complete, and the mixture was cooled to room temperature. The ethyl alcohol was removed from the mixture in vacuo and the residue was treated with water (5 mL) and then acidified with dilute hydrochloric acid to pH 1-2. The mixture was saturated with sodium chloride and then extracted with tent-butyl methyl ether (MTBE). The combined MTBE extracts were washed with brine, dried (Na₂SO₄), filtered and concentrated in vacuo to give white solid (0.42 g, 79.2%). The product was characterized by spectral data ($^1$H NMR) and used in the next step without purification.

(L) Synthesis of racemic dimethyl-(3-methyl-2-oxohept-5-yn-1-yl)-phosphonate(20)

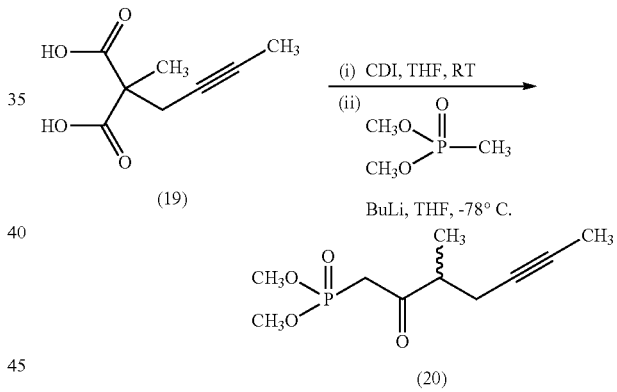

| Name | Amount | mmol | Eq. |
|---|---|---|---|
| Methyl-(2-butynyl)-malonic acid (19) | 0.41 g | 2.59 | 1.00 |
| 1,1'-Carbonyldiimidazole | 0.44 g | 2.71 | 1.05 |
| Dimethyl methylphosphonate | 0.80 g | 6.45 | 2.49 |
| n-Butyllithium in hexane (1.6 M) | 3.2 mL | 5.12 | 1.98 |
| Tetrahydrofuran (anhydrous) | 13 mL | NA | NA |

To a solution of methyl-(2-butynyl)malonic acid (19) (0.41 g, 2.59 mmol) in anhydrous tetrahydrofuran (5 mL) was added 1,1'-carbonyldiimidazole(0.44 g, 2.71 mmol) under argon at room temperature. The reaction mixture was stirred at room temperature for 30 min. In the meantime, lithium derivative of dimethyl methylphosphonate was prepared by adding a solution of n-butyllithium in hexane (1.6 M) (3.2 mL, 5.12 mmol) to the solution of dimethyl methylphosphonate (0.80 g, 6.45 mmol) in tetrahydrofuran (8 mL) at −78° C. over a period of 15 min and stirred the mixture at −78° C. for 15 min. To this solution was added to the above mixture at −78° C. over a period of 5 min. The reaction mixture was stirred at this temperature for 30 min and checked by tlc (EtOAc, 100%). The mixture was allowed to warm to room temperature overnight. The mixture was quenched with saturated ammonium chloride (15 mL) and extracted with ethyl acetate. The combined ethyl acetate extracts were washed with brine, dried (Na₂SO₄), filtered and concentrated in vacuo to give yellow liquid (0.56 g). The spectral data (¹H NMR) of the crude product indicated the desired racemic dimethyl-(3-methyl-2-oxo-hept-5-yn-1-yl)-phosphonate(20) along with some dimethyl methylphosphonate.

(M) Synthesis of racemic 2-Methylhex-4-ynoic acid (21)

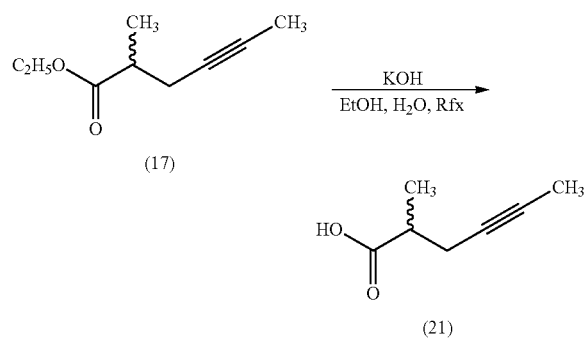

| Name | Amount | mmol | Eq. |
|---|---|---|---|
| Racemic Ethyl 2-methylhex-4-ynoate (17) | 5.62 g | 36.44 | 1.00 |
| Potassium hydroxide | 4.10 g | 73.07 | 2.00 |
| Ethanol | 50 mL | NA | NA |
| Water | 10 mL | NA | NA |

To a solution of racemic ethyl 2-methyl-hex-4-ynoate (17) (5.62 g, 36.44 mmol) in ethanol (50 mL) was added a solution of potassium hydroxide (4.10 g, 73.07 mmol) in water (10 mL). The reaction mixture was gently heated to reflux for 3 h and checked by tlc (EtOAc/Hexane, 1:9 and 3:7). The reaction mixture was cooled to room temperature over a period of 1 h. The mixture was evaporated in vacuo to remove ethanol. The aqueous residue was diluted with water (50 mL) and acidified with 2N hydrochloric acid to pH 1-2. The mixture was saturated with sodium chloride and then extracted with MTBE. The combined MTBE extracts were washed with brine, dried (Na₂SO₄), filtered and concentrated in vacuo to give racemic 2-methylhex-4-ynoic acid (21) as pale yellow liquid (4.44 g, 96.5%). The ¹H NMR spectrum was consistent with the structure and used in the next step without further purification.

(N) Synthesis of diastereomeric mixture of pseudoephedrine methyl-hexynamide(22)

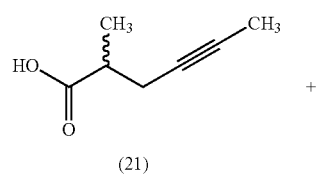

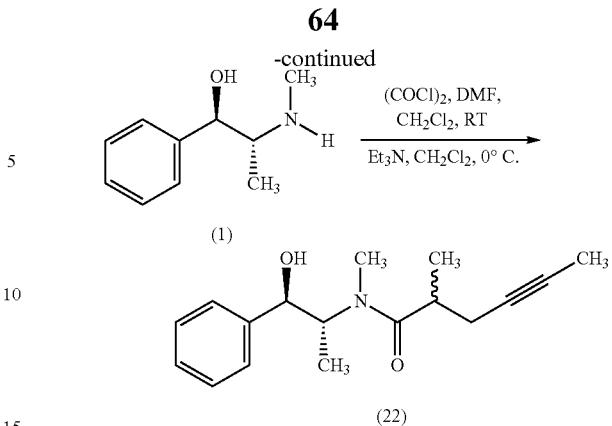

| Name | Amount | mmol | Eq. |
|---|---|---|---|
| (1R,2R)-Pseudoephedrine (1) | 0.33 g | 2.00 | 1.00 |
| Racemic 2-Methylhex-4-ynoic acid (21) | 0.30 g | 2.38 | 1.19 |
| Oxalyl chloride (2.0 M in dichloromethane) | 1.20 mL | 2.40 | 1.20 |
| N,N-Dimethylformamide | 1 drop | NA | NA |
| Triethylamine | 0.29 g | 2.86 | 1.43 |
| Dichloromethane (anhydrous) | 15 mL | NA | NA |

To a solution of (1R,2R)-pseudoephedrine (1) (0.33 g, 2.00 mmol) in anhydrous dichloromethane (10 mL) was added triethylamine (0.29 g, 2.86 mmol) at room temperature. The clear solution was cooled to 0° C. and then a solution of freshly prepared racemic 2-methylhex-4-ynoic acid chloride (from racemic 2-methylhex-4-ynoic acid (21) (0.30 g, 2.38 mmol) and oxalyl chloride dichloromethane (2.0M, 1.20 mL, 2.40 mmol) and N,N-dimethylformamide (1 drop) in dichloromethane (5 mL) at room temperature for 1 h) was added over a period of 5 min under argon. The reaction mixture was stirred at 0° C. for 30 min and checked by tlc (EtOAc/Hexane, 7:3). The reaction was complete and the mixture was quenched with water (5 mL) and dichloromethane was removed in vacuo. The aqueous residue was extracted with tent-butyl methyl ether (MTBE). The combined MTBE extracts were washed with water, 10% hydrochloric acid, water, saturated sodium bicarbonate, brine, dried (Na₂SO₄), filtered and concentrated in vacuo to give pale yellow viscous liquid (0.59 g). The crude product was characterized by spectral data (IR, ¹H NMR). Attempted crystallization of the crude product in various solvents was not successful. The chromatography of crude product in silica gel (22.9 g) using a mixture of ethyl acetate in hexane (10-40%) gave purediastereomeric mixture of pseudoephedrine methyl-hexynamide (22)as a colorless viscous liquid (0.34 g). The pure product was characterized by spectral data (¹H NMR) and diastereomeric purity by HPLC.

(O) Synthesis of diastereomeric mixture of Pseudoephedrine methyl-hexynamide acetate (23)

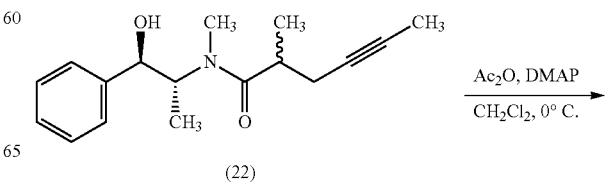

-continued

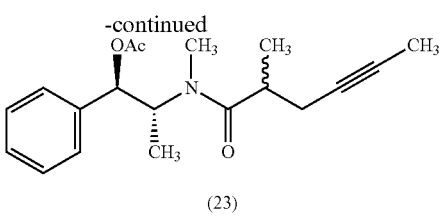

(23)

| Name | Amount | mmol | Eq. |
|---|---|---|---|
| Diastereomeric mixture of Pseudoephedrine methyl-hexynamide (22) | 0.09 g | 0.329 | 1.00 |
| 4-(Dimethylamino)pyridine | 0.06 g | 0.491 | 1.49 |
| Acetic anhydride | 0.05 g | 0.49 | 1.49 |
| Dichloromethane (anhydrous) | 3 mL | NA | NA |

To a solution of diastereomeric mixture of pseudoephedrine methyl-hexynamide (22) (0.09 g, 0.329 mmol) in anhydrous dichloromethane (3 mL) was added 4-(dimethylamino)pyridine (DMAP) (0.06 g, 0.491 mmol) followed by acetic anhydride (0.05 g, 0.49 mmol) under argon at ambient temperature. The reaction mixture was stirred at room temperature for 2 h. After 2 h, the reaction was complete (tic, EtOAc/Hexane, 1:1). The mixture was evaporated in vacuo to remove dichloromethane and the residue was treated with water (5 mL) and tent-butyl methyl ether (MTBE) (10 mL). The organic layer was separated and the aqueous layer was extracted with MTBE. The combined organic extracts were washed with water, saturated sodium bicarbonate, water, 0.1 N hydrochloric acid, water, brine, dried ($Na_2SO_4$), filtered and concentrated in vacuo to give diastereomeric mixture of pseudoephedrine methyl-hexynamide acetate (23) as a colorless viscous liquid (0.8 g, 77%). The product was characterized by spectral data ($^1H$ NMR) and diastereomeric purity by HPLC.

Example 2

Preparation of Beraprost (I)

Beraprost can be prepared starting from 1,3-Cyclopentadiene according to the following Scheme VIII.

Scheme VIII:

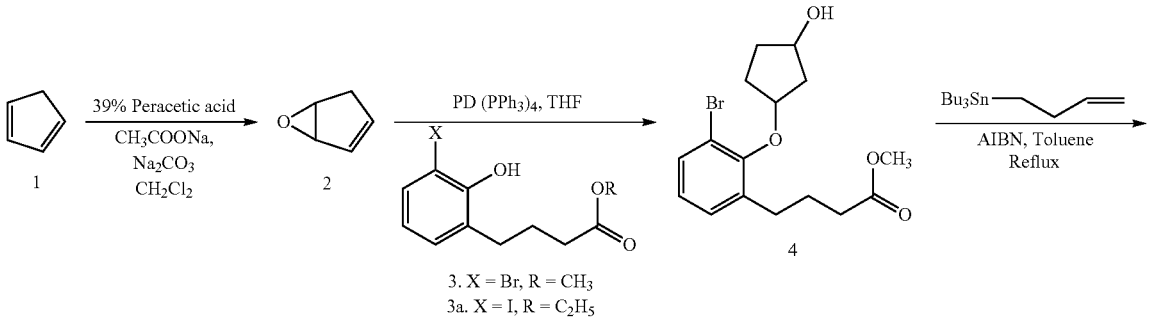

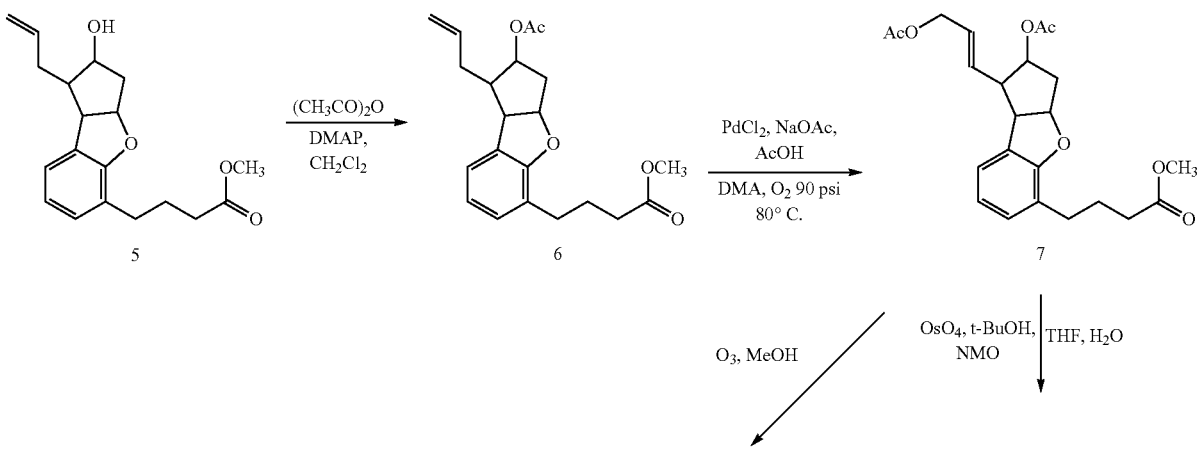

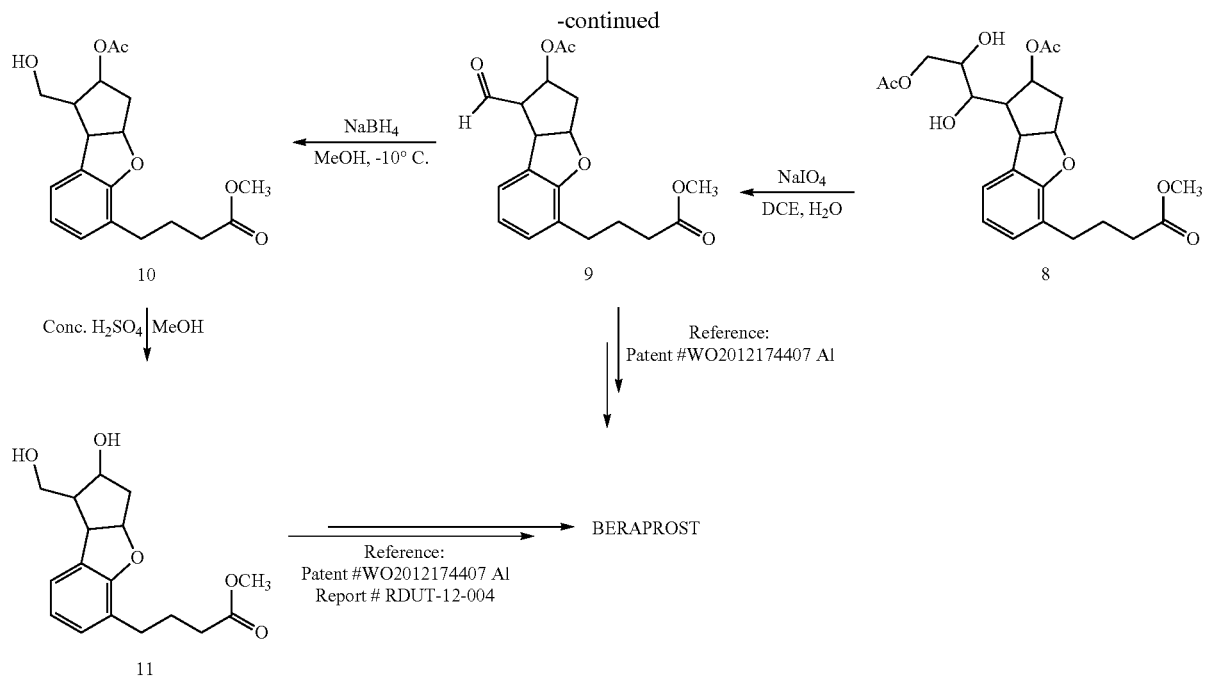

(A) Synthesis of Cyclopentadiene monoepoxide (2)

(B) Synthesis of Bromophenyl hydroxy cyclopentenyl ether (4)

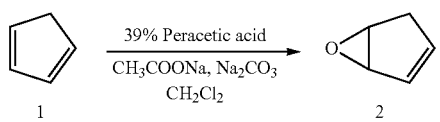 [SMILES: C1=CCC=C1 ; C1=CC2OC2C1]

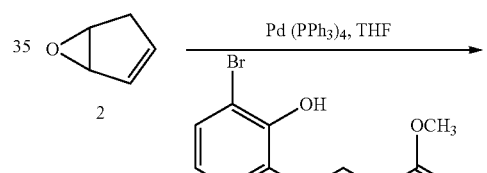

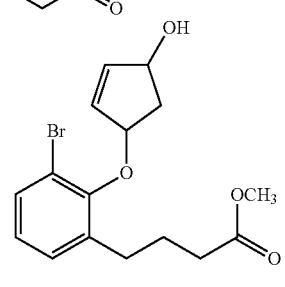

| Name | Amount | mmol | Eq. |
|---|---|---|---|
| 1,3-Cyclopentadiene (1) | 3.4 g | 51.4 | 1.0 |
| Peracetic acid (~39% in acetic acid) | 10 mL | NA | NA |
| Sodium acetate (anhydrous) | 0.25 g | 3.1 | 0.06 |
| Sodium carbonate | 8.19 g | 77.1 | 1.5 |
| Dichloromethane (anhydrous) | 45 mL | NA | NA |

To a suspension of dried sodium carbonate (8.19 g, 77.1 mmol) in dichloromethane (45 mL) was added 1,3-cyclopentadiene (3.4 g, 51.4 mmol) and stirred at −5° C. To this mixture, a solution of sodium acetate (0.25 g, 3.1 mmol) and peracetic acid (39% in acetic acid) (10 mL) was added slowly over a period of 0.5 h, and stirred at room temperature. After 1.5 h, reaction mixture was filtered through Celite and filtrate was evaporated on rotovap at 44° C. under 600 mm Hg pressure, to remove maximum amount of dichloromethane to yield cyclopentadiene monoepoxide (2) (2.95 g, 70% calculated based on NMR). The crude was carried over as such for next step.

| Name | Amount | mmol | Eq. |
|---|---|---|---|
| Cyclopentadiene monoepoxide (2) | 0.52 g | 5.49 | 3.0 |
| Methyl 4-(3-bromo-2-hydroxyphenyl)butanoate (3) | 0.50 g | 1.83 | 1.0 |
| Tetrakis(triphenylphosphine)palladium(0) | 0.06 g | 0.05 | 0.03 |
| Tetrahydrofuran (anhydrous) | 20 mL | NA | NA |

To a solution of methyl 4-(3-bromo-2-hydroxyphenyl) butanoate (3) (0.5 g, 1.83 mmol) in anhydrous tetrahydrofuran (15 mL) was added tetrakis(triphenylphosphine)palladium(0) (0.4 g, 0.05 mmol) and stirred at 0° C. under argon. To this mixture, cyclopentadiene monoepoxide (2)

(0.52 g, 5.49 mmol) was added slowly using syringe. After the addition, reaction mixture was allowed to attain ambient temperature. The reaction was stirred for 4 h and the progress of the reaction was monitored by TLC (ethyl acetate:hexanes, 1:1). Once the reaction was complete, it was treated with saturated ammonium chloride solution (30 mL) and extracted with ethyl acetate (2×30 mL). The combined ethyl acetate extracts were washed with saturated sodium chloride solution (1×30 mL), dried over anhydrous sodium sulfate, filtered, and concentrated in vacuo to give the crude product (4) (0.8 g) as a viscous liquid. The crude product was combined with another two similar batches (2×0.5 g) and purified by column chromatography using 230-400 mesh silica gel and eluted with gradient solvent of ethyl acetate in hexanes (0-50%). The fractions containing the desired compound (by TLC) were evaporated in vacuo to give pure bromophenyl hydroxy cyclopentenyl ether (4) (1.2 g, 61.5%). The compound was characterized by $^{13}$C NMR, $^{1}$H NMR and MS.

(C) Synthesis of Allyl hydroxy cyclopentabenzofuran (5)

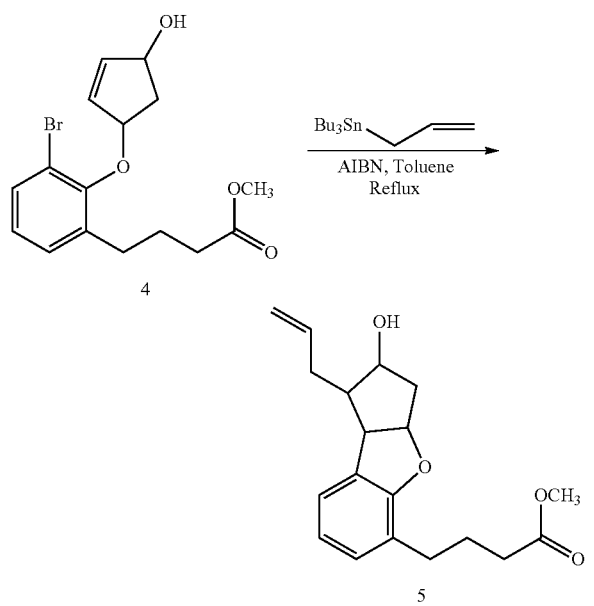

evaporated in vacuo to yield crude product (3.1 g) as a viscous liquid. The crude product was purified by column chromatography using 230-400 mesh silica gel and eluted with gradient solvent of ethyl acetate in hexanes (0-50%). The fractions containing the desired compound (by tlc were evaporated in vacuo to yield allyl hydroxy cyclopentabenzofuran (5) (0.24 g, 26.2%). The compound was characterized by $^{1}$H NMR.

(D) Synthesis of Allyl acetoxy cyclopentabenzofuran (6)

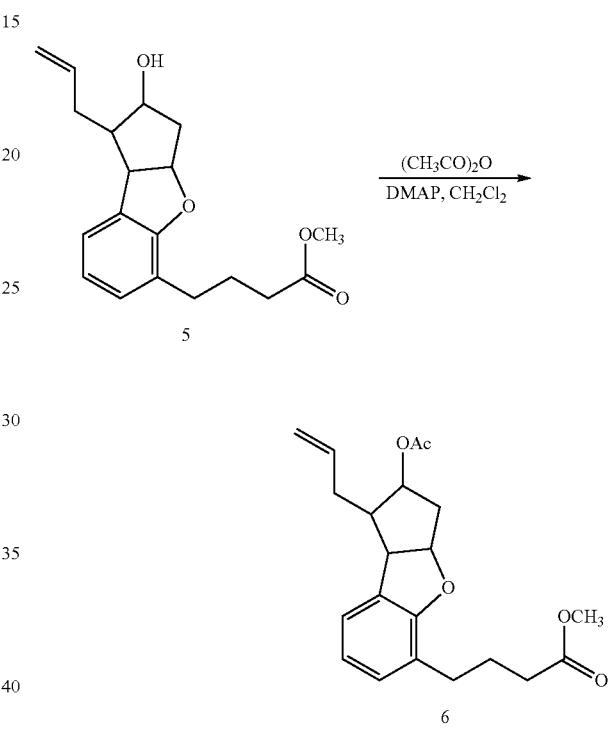

| Name | Amount | mmol | Eq. |
|---|---|---|---|
| Allyl hydroxy cyclopentabenzofuran (5) | 0.24 g | 0.77 | 1.0 |
| Acetic anhydride | 0.12 g | 1.15 | 1.5 |
| 4-(Dimethylamino)pyridine | 0.14 g | 1.15 | 1.5 |
| Dichloromethane (anhydrous) | 10 mL | NA | NA |

To a solution of allyl hydroxy cyclopentabenzofuran (5) (0.24 g, 0.77 mmol) in anhydrous dichloromethane (10 mL) was added 4-(dimethylamino)pyridine (0.14 g, 1.15 mmol) and acetic anhydride (0.12 g, 1.15 mmol) at 0° C. The progress of the reaction was monitored by TLC (ethyl acetate: hexanes, 1:4). After 1 h, the reaction was complete and the mixture was evaporated in vacuo to yield crude product (0.4 g) as a viscous liquid. The crude product was purified by column chromatography using 230-400 mesh silica gel and eluted with gradient solvent of ethyl acetate in hexanes (0-22%). The fractions containing the desired compound (by TLC) were evaporated in vacuo to yield allyl acetoxy cyclopentabenzofuran (6) (0.25 g, 92.6%). The compound was characterized by chiral HPLC and $^{1}$H NMR.

| Name | Amount | mmol | Eq. |
|---|---|---|---|
| Bromophenyl hydroxy cyclopentenyl ether (4) | 1.05 g | 2.95 | 1.0 |
| Allyltributylstannane | 1.89 g | 5.90 | 2.0 |
| Azobisisobutyronitrile | 0.35 g | 2.06 | 0.7 |
| Toluene (anhydrous) | 22 mL | NA | NA |

To a solution of bromophenyl hydroxycyclopentenyl ether (4) (1.05 g, 2.95 mmol) in anhydrous toluene (22 mL) was added allyltributylstannane (1.89 g, 5.90 mmol) and azobisisobutyronitrile (0.05 g, 0.29 mmol) at ambient temperature. This reaction mixture was heated to reflux for 3 h during which azobisisobutyronitrile (0.3 g, 1.76 mmol) was added in three portions. The progress of the reaction was monitored by TLC (ethyl acetate:hexanes, 1:1). At this stage the reaction was complete and the reaction mixture was

(E) Synthesis of Diacetoxy cyclopentabenzofuran alkene (7)

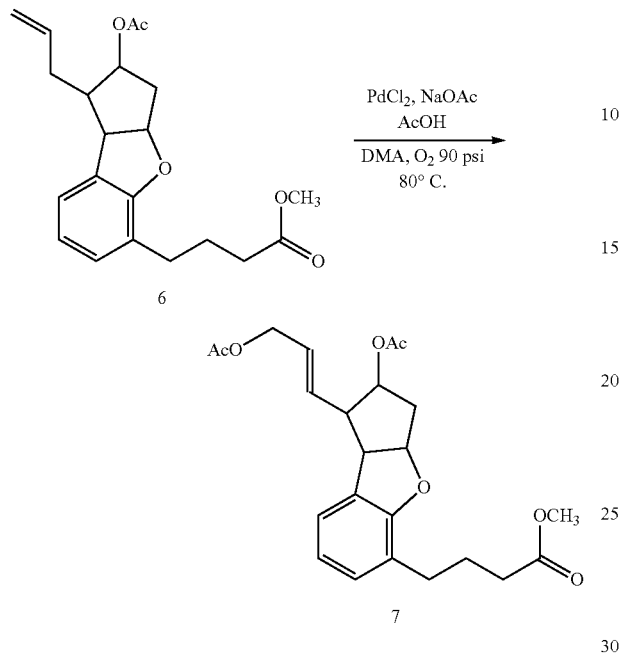

| Name | Amount | mmol | Eq. |
| --- | --- | --- | --- |
| Allyl acetoxy cyclopentabenzofuran (6) | 2.8 g | 7.81 | 1.0 |
| Palladium(II) chloride | 0.03 | 0.15 | 0.02 |
| Sodium acetate (anhydrous) | 0.13 | 1.56 | 0.2 |
| Acetic acid | 9 mL | NA | NA |
| N, N-Dimethylacetamide | 48 mL | NA | NA |
| Molecular sieve 3 A° | 1.8 g | NA | NA |

To a solution of allyl acetoxy cyclopentabenzofuran (6) (2.8 g, 7.81 mmol) in N,N-dimethylacetamide (48 mL) was added palladium(II) chloride (0.03 g, 0.15 mmol), anhydrous sodium acetate (0.13 g, 1.56 mmol), acetic acid (9 mL) and molecular sieve 3 A° (1.8 g) in a pressure reactor vessel. This mixture was degassed on vacuo and replaced with oxygen. This operation was performed five times to ensure complete removal of atmospheric air from the system, and then the temperature was increased to 80° C. while keeping oxygen pressure at 60 psi. After the reaction temperature reached 80° C., the oxygen pressure was increased to 90 psi. The progress of the reaction was monitored by TLC (ethyl acetate:hexanes, 2:3). After 48 h, some starting material was observed on TLC, major being product. The reaction mixture was treated with saturated sodium bicarbonate solution (70 mL) at 0° C. and extracted with tent-butyl methyl ether (2×50 mL). The combined tert-butyl methyl ether extracts were washed with saturated sodium chloride solution (1×50 mL), dried over anhydrous sodium sulfate, filtered, and concentrated in vacuo to give the crude product (4.1 g) as a viscous liquid. The crude product was purified by column chromatography using 230-400 mesh silica gel and eluted with gradient solvent of ethyl acetate in hexanes (0-30%). The fractions containing the desired compound (by TLC) were evaporated in vacuo to yield diacetoxy cyclopentabenzofuran alkene (7) (1.07 g, 33.0%). The compound was characterized by $^1$H NMR.

(F) Synthesis of Diacetoxy cyclopentabenzofuran diol (8)

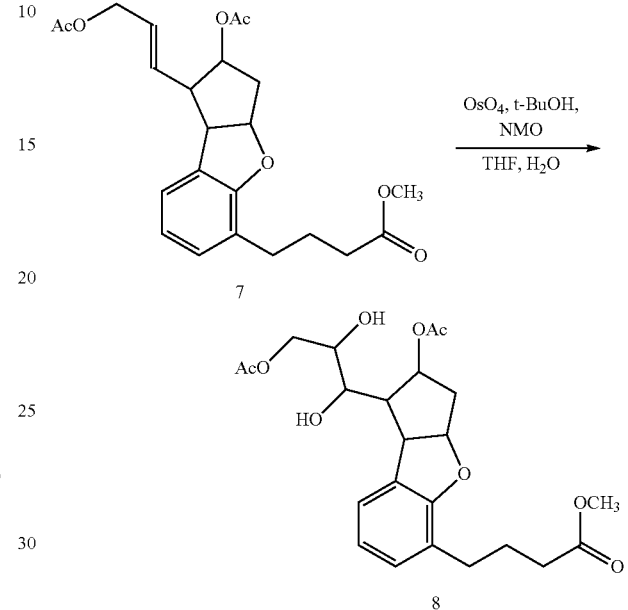

| Name | Amount | mmol | Eq. |
| --- | --- | --- | --- |
| Diacetoxy cyclopentabenzofuran alkene (7) | 0.25 g | 0.60 | 1.0 |
| Osmium tetroxide | 0.02 g | 0.12 | 0.2 |
| 4-Methylmorpholine N-oxide | 0.07 g | 0.61 | 1.02 |
| tert-Butanol | 10 mL | NA | NA |
| Tetrahydrofuran | 3 mL | NA | NA |
| Water | 1 mL | NA | NA |

To a solution of diacetoxy cyclopentabenzofuran alkene (7) (0.25 g, 0.60 mmol) in a mixture of tent-butanol (10 mL), tetrahydrofuran (3 mL) and water (1 mL) was added 4-methylmorpholine N-oxide (0.07 g, 0.61 mmol) and osmium tetroxide (0.01 g, 0.06 mmol) at room temperature under argon. The reaction flask was covered with aluminum foil to protect from light. This reaction mixture was stirred for 2.5 h and the progress of the reaction was monitored by TLC (ethyl acetate:hexanes, 1:1). After 2.5 h, another portion of osmium tetroxide (0.01 g, 0.06 mol) was added and stirred for additional 2 h, and the reaction was complete. At this stage, the reaction mixture was treated with 10% sodium thiosulfate (10 mL) and evaporated in vacuo to remove organic volatiles. The remaining residue was extracted with dichloromethane (2×20 mL). The combined dichloromethane extracts were washed with saturated sodium chloride solution (1×20 mL), dried over anhydrous sodium sulfate, filtered, and concentrated in vacuo to give the crude product (0.3 g) as a viscous liquid. The crude product was purified by column chromatography using 230-400 mesh silica gel and eluted with gradient solvent of ethyl acetate in hexanes (0-100%). The fractions containing the desired compound

(G) Synthesis of Acetoxy cyclopentabenzofuran aldehyde (9)

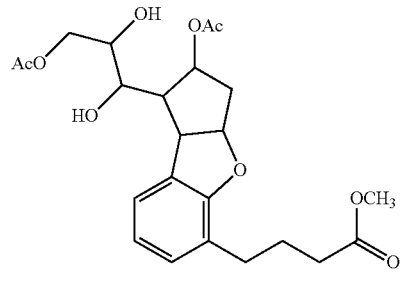

8

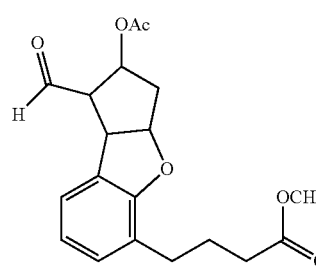

9

| Name | Amount | mmol | Eq. |
|---|---|---|---|
| Diacetoxy cyclopentabenzofuran diol (8) | 0.18 g | 0.42 | 1.0 |
| Sodium periodate | 0.17 g | 0.83 | 2.0 |
| 1,2-Dichloroethane | 5 mL | NA | NA |
| Water | 5 mL | NA | NA |

(by TLC) were evaporated in vacuo to yield diacetoxy cyclopentabenzofuran diol (8) (0.22 g, 81.4%). The compound was characterized by $^1$H NMR.

To a solution of diacetoxy cyclopentabenzofuran diol (8) (0.18 g, 0.42 mmol) in a mixture of 1,2-dichloroethane (5 mL) and water (5 mL) was added sodium periodate (0.17 g, 0.83 mmol) at ambient temperature under argon. The mixture was stirred overnight and the progress of the reaction was monitored by TLC (ethyl acetate:hexanes, 1:1). After 24 h, the reaction was complete. The reaction mixture was extracted with dichloromethane (2×20 mL). The combined dichloromethane extracts were washed with saturated sodium chloride solution (30 mL), dried over anhydrous sodium sulfate, filtered, and concentrated in vacuo to give the crude acetoxy cyclopentabenzofuran aldehyde (9) (0.15 g) as a viscous liquid. The crude product was characterized by $^1$H NMR and used as such in the next step without further purification.

Synthesis of Acetoxy cyclopentabenzofuran alcohol (10)

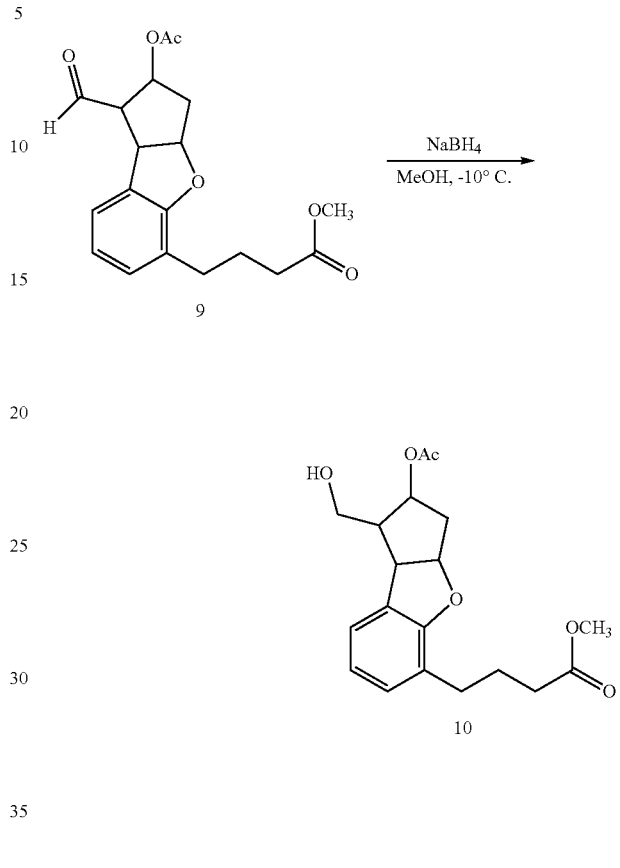

| Name | Amount | mmol | Eq. |
|---|---|---|---|
| Acetoxy cyclopentabenzofuran aldehyde (9) | 0.15 g | 0.43 | 1.0 |
| Sodium borohydride | 0.17 g | 0.43 | 1.0 |
| Methanol (anhydrous) | 10 mL | NA | NA |

To a solution of acetoxy cyclopentabenzofuran aldehyde (9) (0.15 g, 0.43 mmol) in anhydrous methanol (10 mL) was added sodium borohydride (0.02 g, 0.43 mmol) at −10° C. under argon. The reaction was stirred for 1.5 h and the progress of the reaction was monitored by TLC (ethyl acetate:hexanes, 7:3). After 1.5 h, the reaction was complete. The reaction mixture was treated with 10% HCl solution and organic volatiles were evaporated in vacuo, the residue was extracted with dichloromethane (2×20 mL). The combined dichloromethane extracts were washed with saturated sodium chloride solution (20 mL), dried over anhydrous sodium sulfate, filtered, and concentrated in vacuo to give the crude product (0.2 g) as a viscous liquid. The crude product (1.6 g) was purified by column chromatography using 230-400 mesh silica gel and eluted with gradient solvent of ethyl acetate in hexanes (0-80%). The fractions containing the desired compound (by TLC) were evaporated in vacuo to yield acetoxy cyclopentabenzofuran alcohol (10) (0.08 g, 53.2%) as a viscous liquid. The compound was characterized by $^1$H NMR.

(H) Synthesis of Beraprost methyl ester diol (11)

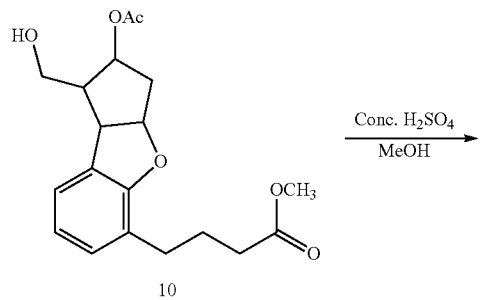

| Name | Amount | mmol | Eq |
|---|---|---|---|
| Acetoxy cyclopentabenzofuran alcohol (10) | 0.08 g | 0.23 | 1.0 |
| Conc. Sulfuric acid | 0.1 g | NA | NA |
| Methanol (anhydrous) | 10 mL | NA | NA |

To a solution of acetoxy cyclopentabenzofuran alcohol (10) (0.08 g, 0.23 mmol) in anhydrous methanol (5 mL) was added a solution of conc. sulfuric acid (0.1 mL) in anhydrous methanol (5 mL) under argon. The reaction mixture was stirred overnight and the progress of the reaction was monitored by TLC (dichloromethane: methanol 9:1). After 24 h, the reaction was complete. The reaction mixture was treated with saturated sodium bicarbonate solution and organic volatiles were evaporated in vacuo. The reside was extracted with dichloromethane (1×20 mL) and the organic extract was washed with saturated sodium chloride solution (50 mL), dried over anhydrous sodium sulfate, filtered, and concentrated in vacuo to give the crude racemic Beraprost diol (11) (0.6 g) as a white powder. The crude product was purified by column chromatography using 230-400 mesh silica gel and eluted with gradient solvent of ethyl acetate in hexanes (0-100%). The fractions containing the desired compound (by TLC) were evaporated in vacuo to yield Beraprost methyl ester diol (11) (0.05 g, 72.2%) as a white powder. The compound was characterized by $^1$H NMR, $^{13}$C NMR and chiral HPLC.

The diol (11) can be converted to Beraprost according to the following procedure:

(I) Synthesis of Trityl ether (2)

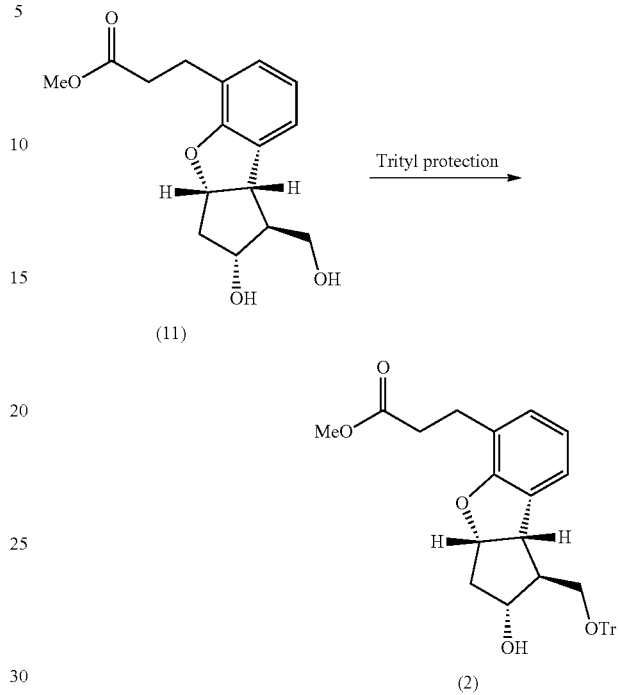

| Name | Amount | Eq |
|---|---|---|
| Diol (11) | 10.00 g | 1.0 |
| Trityl chloride | 27.30 g | 3.0 |
| Triethylamine | 13.21 g | 4.0 |
| DMAP | 4.00 g | 1.0 |
| Dichloromethane | 20.00 mL | NA |
| DMF | 200.00 mL | NA |

A 500 mL, two-necked, round-bottom flask equipped with a magnetic stir bar and an argon inlet outlet adapter was charged with a solution of ester diol (11) (10.00 g) in dichloromethane (200 mL). To this solution triethylamine (13.21 g), 4-(dimethylamino)pyridine (4.0 g), and DMF (20 mL) were added at ambient temperature under argon. To this mixture trityl chloride (27.30 g) was added. The mixture was stirred until a clear solution was obtained. The reaction was stirred for ~31 h at ambient temperature. After ~31 h, the progress of the reaction was monitored by TLC. The mixture was washed with saturated ammonium chloride (200 mL). The organic layer was separated, dried over anhydrous sodium sulfate, filtered, and concentrated in vacuo to give the crude product (2) as a viscous oil. The crude product from another 10-g batch was combined and purified by column chromatography using 230-400 mesh silica gel and eluted with a gradient solvent of ethyl acetate in hexanes (5-50%). The fractions containing the desired compound (by TLC) were evaporated in vacuo to yield trityl ether (2) (33.82 g, 94.6% from two 10-g batches). The compound was characterized by spectral data.

(J) Synthesis of TBDMS ether (3)

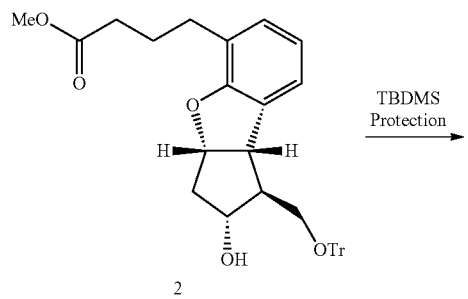

2

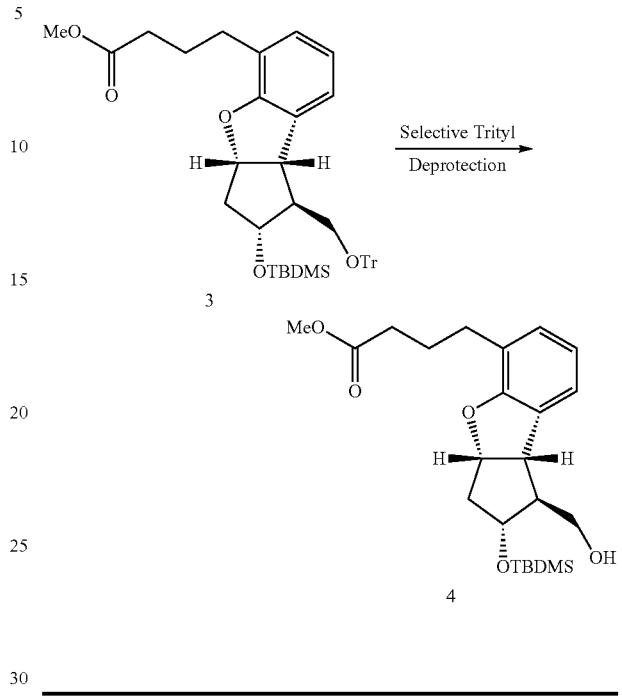

3

| Name | Amount | Eq |
| --- | --- | --- |
| Trityl ether (2) | 39.50 g | 1.0 |
| TBDMS triflate | 22.84 g | 1.2 |
| 2,6-Lutidine | 18.51 g | 2.4 |
| Dichloromethane | 600 mL | NA |

A 1000 mL, two-necked, round-bottom flask equipped with a magnetic stir bar and an argon inlet-outlet adapter was charged with a solution of trityl ether (2) (39.50 g) in anhydrous dichloromethane (600 mL). To this solution, 2,6-lutidine (18.51 g) was added at ambient temperature under argon. The mixture was stirred until a clear solution was obtained. The mixture was cooled to −15° C. and TBDMS triflate (22.84 g) was added in portions while maintaining the temperature below −10° C. The reaction was stirred for ~1 h and the progress of the reaction was monitored by TLC. At this stage the reaction was complete. To the reaction mixture hexanes were added (600 mL) and temperature was allowed to rise to ambient. This mixture was passed through a pad of 230-400 mesh silica gel (384 g) and eluted with a gradient solvent of ethyl acetate in hexanes (5-15%). The fractions containing the desired compound were evaporated in vacuo to yield silyl ether (3) (47.70 g, 99.6%). The compound was characterized by spectral data.

(K) Synthesis of Alcohol (4) via Selective Deprotection of Trityl Ether (3)

3

4

| Name | Amount | Eq |
| --- | --- | --- |
| Trityloxy-TBDMS ether (3) | 14.58 g | 1.0 |
| Diethylaluminum chloride in heptane (1.0 M) | 55.00 mL | 2.5 |
| Dichloromethane | 175 mL | NA |

A 500 mL, two-necked, round-bottom flask equipped with a magnetic stir bar and an argon inlet outlet adapter was charged with a solution of trityloxy-TBDMS ether (3) (14.58 g) in anhydrous dichloromethane (175 mL). To this solution, diethylaluminum chloride (22.00 mL, 1M in dichloromethane, 1.0 eq.) was added at ambient temperature under argon. The reaction was stirred for ~3 h and the progress of the reaction was monitored by TLC. At this stage reaction was not complete and an extra one equivalent of diethylaluminum chloride (22.00 mL, 1M in dichloromethane, 1.0 eq.) was added at ambient temperature, and the reaction mixture was stirred for another 3 h while the progress was monitored by TLC. After a total of 6 h the reaction mixture showed the presence of some starting material and another 0.5 equivalent of diethyl aluminum chloride (11.00 mL, 1M in heptane, 0.5 eq.) was added at ambient temperature and reaction mixture was stirred for another 1 h and progress of the reaction was monitored by TLC. At this stage reaction was complete, and the reaction mixture was cooled to 0° C. To the reaction mixture, saturated sodium bicarbonate solution (240 mL) was added. Once the temperature was raised to ambient, and the compound was extracted with dichloromethane. The combined extracts of dichloromethane were washed with brine, dried over sodium sulfate and evaporated in vacuo to obtain crude, viscous oil (14.01 g). This crude compound was passed through a pad of 230-400 mesh silica gel (197 g) and eluted with a gradient solvent mixture of ethyl acetate in hexanes (10-50%). The fractions containing the desired compound were evaporated in vacuo to yield hydroxy-silyl ether (4) (8.54 g, 92.3%). The compound was characterized by spectral data.

(L) Side Chain Coupling (Synthesis of Enone 6 via intermediacy of an Aldehyde (5)

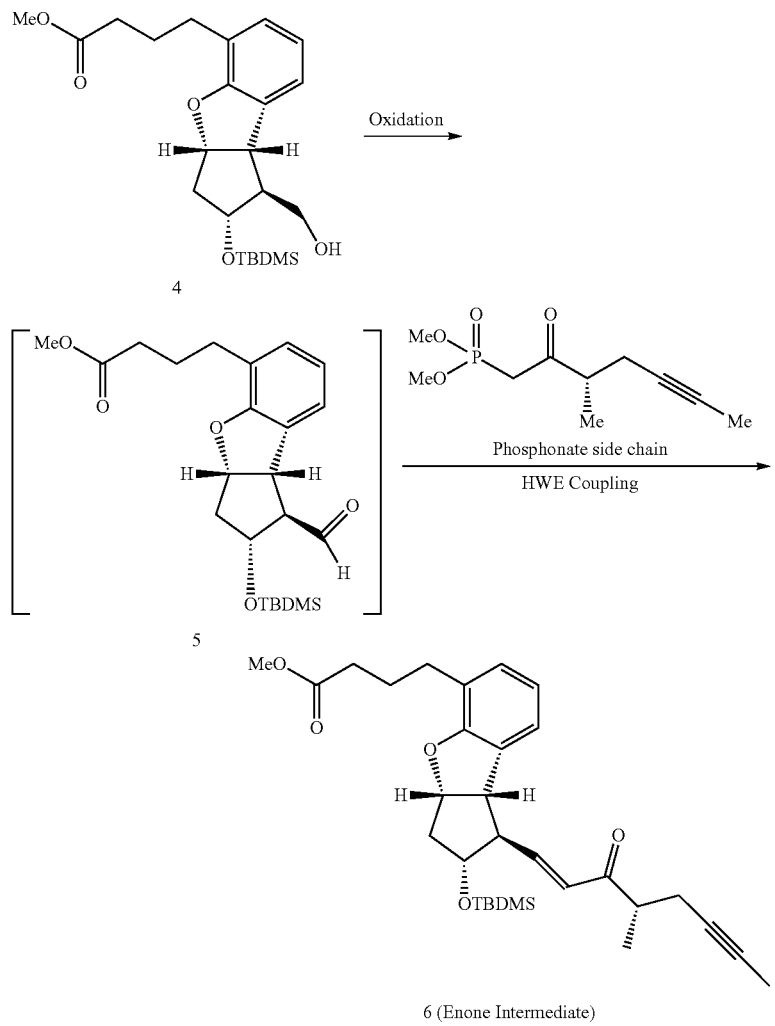

6 (Enone Intermediate)

| Name | Amount | | Eq |
|---|---|---|---|
| Alcohol (4) | 8.54 | g | 1.0 |
| Oxalyl Chloride in CH$_2$Cl$_2$ (2.0 M) | 23.00 | mL | 2.2 |
| Dimethyl sulfoxide | 4.33 | mL | 3.0 |
| Triethylamine | 14.15 | mL | 5.0 |
| Dichloromethane | 155.00 | mL | NA |
| Phosphonate side chain | 8.50 | g | 1.0 |
| LiOH•H$_2$O | 1.86 | g | 1.0 |
| MTBE | 350 | mL | NA |

To a cooled (−78° C.) and stirred solution of oxalyl chloride (23.00 mL) in dichloromethane (60 mL) was added slowly a solution of dimethyl sulfoxide (4.33 mL) in dichloromethane (35 mL)under argon. After stirring for 45 minutes at −78° C. to −70° C., a solution of alcohol (4) (8.54 g) in dichloromethane (60 mL) was added to this reaction mixture while maintaining the temperature below −65° C. After stirring for 60 minutes at −65° C., temperature of reaction mixture was raised to −45° C. to −40° C. and stirred for 60 minutes at this temperature. This reaction mixture was cooled to −65° C. and quenched by slow addition of triethylamine (14.15 mL). The reaction mixture was stirred for another 30 minutes at −65° C. and the completion of reaction was checked by the TLC. The temperature of reaction mixture was raised to ambient and water (60 mL) was added. The two-phase mixture was stirred for 5 minutes at room temperature after which the organic phase was separated and the aqueous phase was extracted with dichloromethane (2×75 mL) to ensure complete extraction of product into the organic layer. The combined organic extracts were washed with brine (100 mL), dried over sodium sulfate and evaporated in vacuo to obtain crude aldehyde (9.77 g). In a separate 500-mL, two-necked, round-bottom flask equipped with a magnetic stir bar and an argon inlet-outlet adapter, a solution of phosphonate side chain (8.50 g) in MTBE (175 mL) was charged. To this LiOH.H$_2$O (1.86 g) was added and the mixture was stirred for ~1 h. After ~1 h, a solution of crude aldehyde (5) in MTBE (175 mL) was added slowly over a period of 10 minutes and stirred until completion of reaction. Progress of reaction was monitored by TLC. After the reaction was complete, the reaction mixture was quenched by adding water (175 mL) and the mixture stirred for 15 minutes. The organic layer was separated and aqueous layer was extracted with ethyl acetate (3×70 mL). The combined organic extracts were washed with water (70 mL), brine (30 mL), dried over sodium sulfate and evaporated in vacuo to obtain a crude viscous liquid of enone intermediate (6) (11.22 g). This crude enone intermediate (6) was passed through a pad of 230-400 mesh silica gel (328 g) and eluted with a gradient solvent of ethyl acetate in hexanes (2-20%). The fractions containing the desired compound were evaporated in vacuo to yield enone (6) (19.42 g, 80%, from combined two batches). The pure compound was characterized by spectral data.

(M) Chiral Reduction of Enone (6)

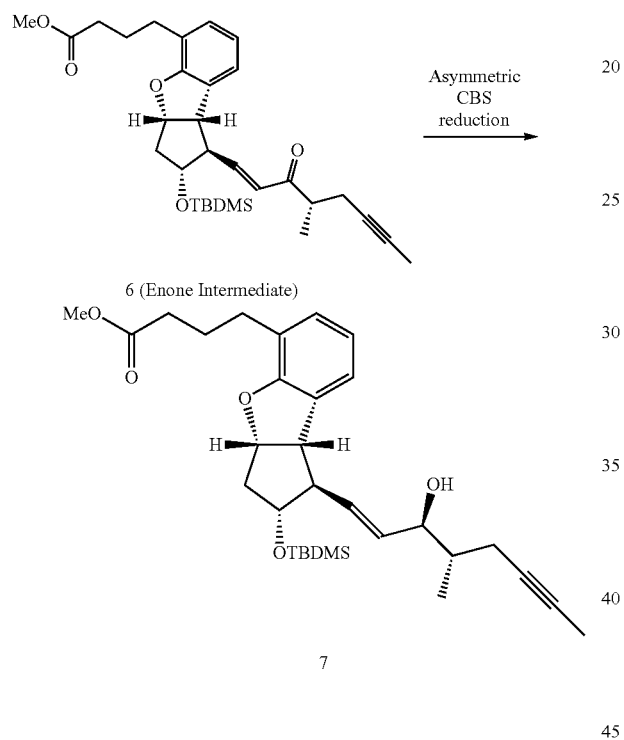

| Name | Amount | Eq |
| --- | --- | --- |
| Enone (6) | 0.11 g | 1.0 |
| (R)-(+)-2-Methyl-CBS-oxazaborolidine (1 M in Toluene) | 0.43 mL | 2.0 |
| Borane-methyl sulfide complex (2 M in Toluene) | 0.32 mL | 3.0 |
| Toluene | 5.0 mL | NA |

A 100 mL, three-necked, round-bottom flask equipped with a magnetic stir bar, a thermocouple, and an argon inlet-outlet adapter was charged with enone compound (6) (0.11 g) and anhydrous toluene (5.0 mL). A solution of (R)-(+)-2-methyl CBS oxazaborolidine (1.0 Min toluene) (0.43 mL) was added under argon at ambient temperature. The mixture was cooled to −40° C. (dry ice/acetone-bath), and borane-methyl sulfide complex (0.32 mL) was added slowly maintaining the temperature between −40° C. and −30° C. After complete addition, the reaction mixture was stirred for 1-2 h at −30° C. to −25° C. The progress of the reaction was monitored by TLC. The reaction mixture was carefully quenched by slow addition of methanol (2.0 mL) over a period of 2-3 minute maintaining the temperature between −15° C. and −10° C. . The reaction mixture was allowed to warm to room temperature and the stirring was continued for another 20-30 minutes. At this stage, saturated aqueous ammonium chloride solution (5.0 ml) was added with stirring, the organic layer was separated, and the aqueous layer was extracted with ethyl acetate (2×15 mL). The combined organic layers were washed with brine (10 mL), dried over anhydrous sodium sulfate, filtered and concentrated in vacuo to give crude alcohol (7) (0.27 g). This crude alcohol (7) was passed through a pad of 230-400 mesh silica gel (22.5 g) and eluted with a gradient solvent of ethyl acetate in hexanes (0-12%). The fractions containing the desired compound were evaporated in vacuo to yield pure alcohol (7) (0.096 g, 87.2%). The compound was characterized by spectral data.

(N) TBDMS deprotection of 7 to obtain Beraprost Ester diol (9)

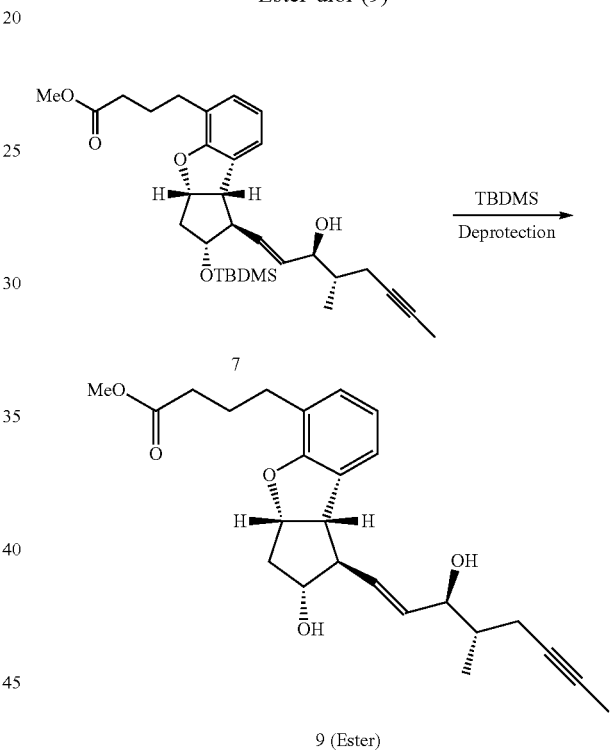

| Name | Amount | Eq |
| --- | --- | --- |
| TBDMS ether (7) | 2.67 g | 1.0 |
| 10% Aqueous HCl | 10.00 mL | 2.3 |
| Methanol | 50.00 mL | NA |

To a solution of TBDMS protected ether (7) (2.67 g) in methanol (50 mL) was added 10% aqueous HCl (10.00 mL) at room temperature. The reaction mixture was stirred at ambient temperature until completion of reaction. After ~1 h the reaction mixture was checked by TLC for its completion. At this stage, the reaction mixture was neutralized with saturated sodium bicarbonate (10 mL) to pH 7-8 and concentrated in vacuo to remove methanol. The reaction mixture was diluted with water (10 mL) and the mixture was then extracted with ethyl acetate (3×30 mL). The combined ethyl acetate extracts were washed with brine (15 mL), dried (Na$_2$SO$_4$), filtered and concentrated in vacuo to give Beraprost ester (9) as a crude, pale-yellow, viscous liquid (2.31 g). The crude product was purified by column chromatography using a gradient solvent of ethyl acetate in hexanes (0-90%). The fractions containing the desired compound were evaporated in vacuo to yield Beraprost ester (9) 0.26 g) which was crystallized using a ethyl acetate and cyclopentane mixture to obtain ester with a chiral purity of 96.24% (by HPLC); mp 82-83° C. (dec.); Required: C=72.79; H=7.82; Found C=72.86; H=7.41. The compound was characterized by spectral data (O) TBDMS deprotection of Enone 6 to obtain Keto-Alcohol (8)

| Name | Amount | Eq |
|---|---|---|
| Enone (6) | 0.450 g | 1.0 |
| 10% Aqueous HCl | 0.90 mL | NA |
| Methanol | 10.00 mL | NA |

To a solution of enone (6) (0.450 g) in methanol (10 mL) was added 10% aqueous HCl (0.90 mL) at ambient temperature. The reaction mixture was stirred at ambient temperature until completion of reaction. After ~3 h the reaction mixture was checked by TLC for its completion. At this stage, the reaction mixture was neutralized with saturated sodium bicarbonate to pH 7-8 and concentrated in vacuo to remove methanol. The reaction mass was diluted with water (10 mL) and the mixture was extracted with ethyl acetate (2×15 mL). The combined ethyl acetate extracts were washed with brine (10 mL), dried (Na$_2$SO$_4$), filtered and concentrated in vacuo to give the keto alcohol (8) as a crude, pale-yellow, viscous liquid (0.400 g). The crude product was crystallized using a ethyl acetate and hexanes mixture to obtain pure, crystalline keto-alcohol (8) (0.210 g, 60%); mp 75-76° C.; the compound was characterized by spectral data.

(P) Chiral Reduction of keto-alcohol (8) to Beraprost ester (9)

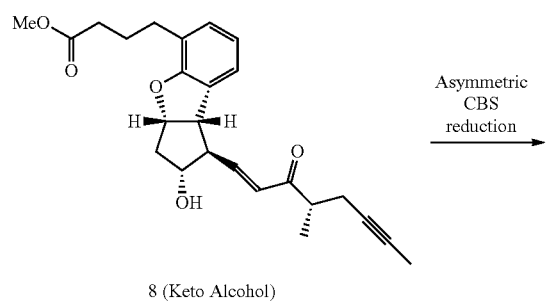

8 (Keto Alcohol)

Asymmetric CBS reduction
→

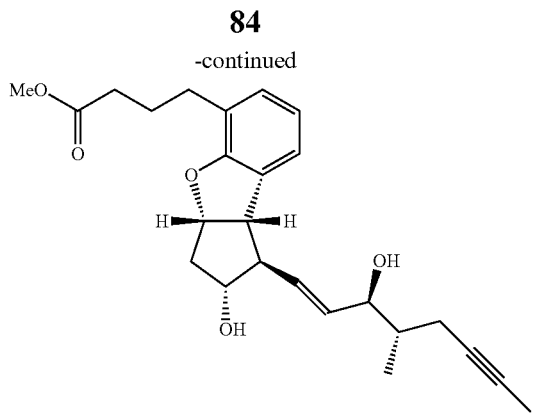

9 (Beraprost Ester)

| Name | Amount | Eq |
|---|---|---|
| Keto-alcohol (8) | 3.25 g | 1.0 |
| (R)-(+)-2-butyl-CBS-oxazaborolidine (I M in Toluene) | 23.8 mL | 3.0 |
| Catecholborane (2 M in Toluene) | 23.8 mL | 3.0 |
| Toluene | 100 mL | NA |

A 100 mL, three-necked, round-bottom flask equipped with a magnetic stir bar, a thermocouple, and an argon inlet-outlet adapter was charged with keto-alcohol (8) (3.25 g) and anhydrous toluene (100 mL). A solution of (R)-(+)-2-butyl CBS oxazaborolidine (1.0 M in toluene) (23.8 mL) was added under argon at room temperature. The mixture was cooled to −15° C. (dry ice/acetone-bath), and catecholborane (23.8 mL) was added slowly maintaining the temperature between −15° C. and −10° C. After complete addition, the reaction mixture was stirred for 1-2 h while slowly allowing the temperature to raise to ambient temperature. The progress of the reaction was monitored by TLC. The reaction mixture was carefully quenched by slow addition of methanol (50 mL) over a period of 10 minutes maintaining the temperature between −15° C. and −10° C. The reaction mixture was allowed to warm to room temperature and the stirring was continued for another 20-30 minutes. At this stage, saturated aqueous ammonium chloride solution (10 ml) was added with stirring. The organic layer was separated, and the aqueous layer was extracted with ethyl acetate (3×50 mL). The combined organic layers were washed with brine (15 mL), dried over anhydrous sodium sulfate, filtered and concentrated in vacuo to give crude Beraprost ester (9). The crude product was purified by column chromatography using a gradient solvent of ethyl acetate in hexanes (0-90%). The fractions containing the desired compound were evaporated in vacuo to yield Beraprost ester (9) (2.53 g, 77%). A small sample was crystallized using an ethyl acetate and hexanes mixture to obtain analytically pure Beraprost ester diol mp 75-76° C. The compound was characterized by spectral data.

(Q) Synthesis of Beraprost

(R) Synthesis of potassium salt of Beraprost (314d) (10)

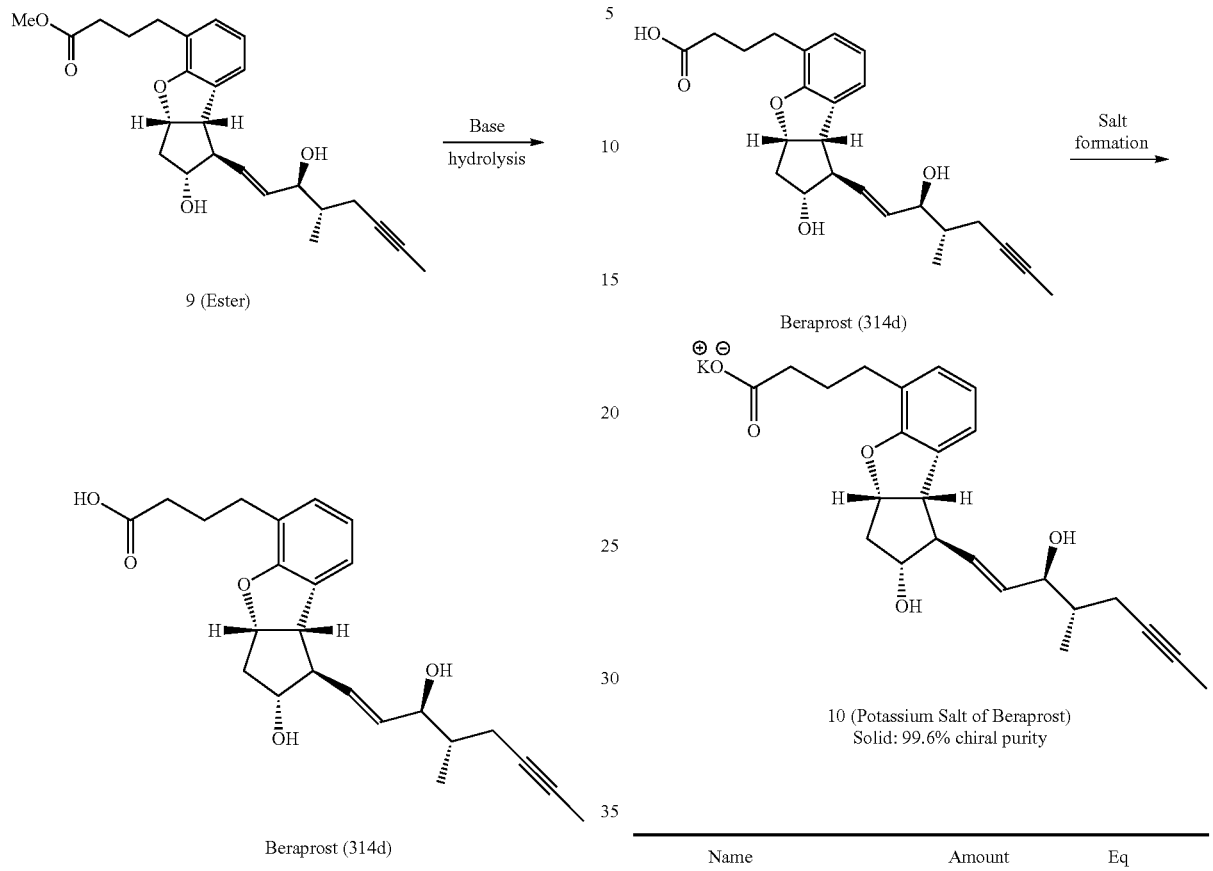

9 (Ester)

Beraprost (314d)

Beraprost (314d)

10 (Potassium Salt of Beraprost)
Solid: 99.6% chiral purity

| Name | Amount | Eq |
|---|---|---|
| Beraprost (314d) | 0.500 g | 1.0 |
| Potassium hydroxide | 0.066 g | 0.95 |
| Ethanol | 3.0 mL | NA |
| Ethyl Acetate | 15.0 mL | NA |

| Name | Amount | Eq |
|---|---|---|
| Beraprost ester (9) | 0.700 g | 1.0 |
| Sodium hydroxide | 0.815 g | 12.0 |
| $H_2O$ | 2.0 mL | NA |
| Methanol | 10.0 mL | NA |

To a solution of Beraprost ester (9) (0.700 g) in methanol (10 mL) was added a solution of sodium hydroxide (0.815 g in 2.0 mL water) at room temperature. The reaction mixture was stirred at room temperature for ~16 h and the progress of the reaction was monitored by TLC. The reaction mixture was concentrated in vacuo to remove methanol and diluted with water (10 mL). This mixture was acidified with 10% hydrochloric acid solution to pH 2-3. The mixture was extracted with ethyl acetate (2×10 mL). The combined ethyl acetate extracts were washed with brine (1×10 mL), dried ($Na_2SO_4$), filtered and concentrated in vacuo to give the desired stereoisomer of Beraprost (314d) as foamy solid (0.700 g). This acid was used out as such for potassium salt formation.

Procedure A:

A 100-mL, two-necked, round-bottom flask equipped with a magnetic stirrer and a thermometer was charged with Beraprost (314d) (0.500 g) and ethyl acetate (15 mL). This mixture was warmed to 75-80° C. to obtain a clear solution. To this clear solution, potassium hydroxide (0.066 g) in ethanol (3.0 mL) was added and stirred for few minutes at 75-80° C., then the mixture was allowed to cool to ambient temperature over a period of approximately 2 h. At ambient temperature, the precipitated product was isolated by filtration and washed with ethanol. The product was transferred from Buchner funnel to a glass dish for air-drying overnight in a fume hood to yield free flowing white-solid salt of Beraprost (0.420 g); the solid was crystallized from ethanol and water to obtain pure stereoisomer of Beraprost potassium salt, chiral purity 99.6% by Chiral HPLC; mp 270-272° C. (dee.); Required: C=66.03; H=6.70; Found C=65.82; H=6.67. The compound was characterized by spectral data.

Procedure B:

A 100-mL, two-necked, round-bottom flask equipped with a magnetic stirrer and a thermometer was charged with Beraprost (314d) (0.490 g) and ethyl alcohol (18 mL). To this clear solution, potassium hydroxide {0.064 g) in water (0.5 mL) was added and the mixture was warmed to 78-80° C. to obtain a clear solution. This was stirred for few minutes at 78-80° C., then the mixture was allowed to cool to ambient temperature over a period of approximately 2 h. At ambient temperature, the precipitated product was isolated by filtration and washed with ethanol. The product was transferred from Buchner funnel to a glass dish for air-drying overnight in a fume hood to yield free flowing white-solid salt of Beraprost (0.314 g).

Example 3

Synthesis of Racemic Beraprost Ester Diol (11) by Radical Cyclization (A) Synthesis of Allyl hydroxy cyclopentabenzofuran (5)

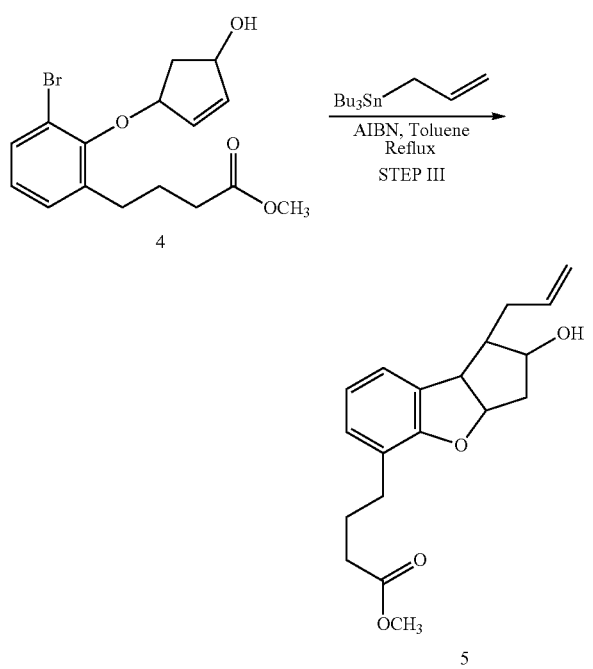

A 250 mL, three necked, round bottom flask fitted with a condenser, a dropping funnel and a rubber septum was charged with a solution of broinophenyl hydroxycyclopentenyl ether (4) (4.3 g, 12.10 mmol) in anhydrous toluene (7 mL). To this, allyltributylstannane (24.4 g, 72.63 mmol) was added and heated to 110° C. under argon. A solution of AIBN (1.0 g, 6.05 mmol) in toluene (14 mL) was added dropwise over a period of 20 minutes and heating was continued at reflux temperature. After complete addition of the AIBN solution, the reaction mixture was heated at reflux for 10 minutes. The progress of the reaction was monitored by TLC. At this stage, the reaction was complete and the reaction mixture cooled to ambient temperature. This reaction mixture was loaded directly onto the silica packed column for purification. The fractions containing the desired compound (checked by TLC) were combined and evaporated in vacuo to yield allyl hydroxy cyclopentabenzofuran (5) (2.27 g, 59.5%). The compound was characterized by $^1$H NMR.

(B) Synthesis of Alkenyl hydroxy cyclopentabenzofuran (6)

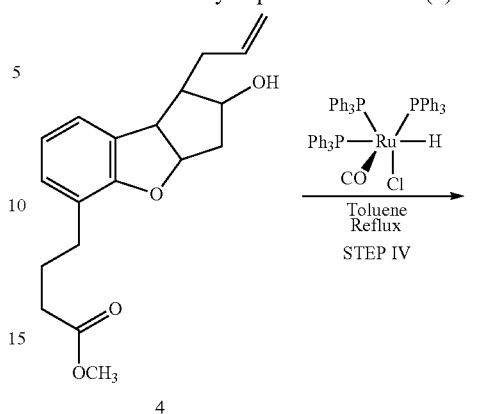

A 100 mL, single necked, round bottom flask fitted with a condenser was charged with a solution of allyl hydroxy cyclopentabenzofuran (5) (2.2 g, 6.95 mmol) in anhydrous toluene (30 mL). To this, carbonylchlorohydridotris(triphenylphosphine)ruthenium(II) (0.33 g, 0.34 mmol) was added and heated to reflux at 110° C. under argon. The progress of the reaction was monitored by $^1$HNMR. After 2.5 h, the reaction was complete, then the reaction mixture was cooled to ambient temperature and loaded directly onto the silica packed column for purification. The fractions containing the desired compound (checked by TLC, 45% ethylacetate: hexanes) were combined and evaporated in vacuo to yield alkenyl hydroxy cyclopentabenzofuran (6) (1.836 g, 83.5%). The compound was characterized by $^1$H NMR.

(C) Synthesis of Alkenyl hydroxy cyclopentabenzofuran (6)

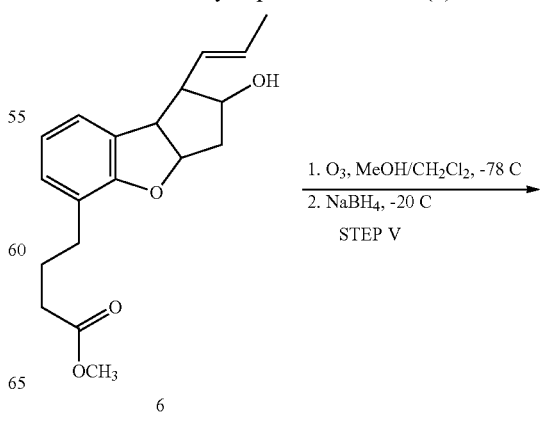

-continued

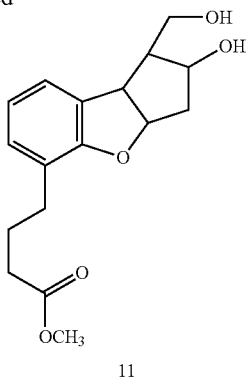
11

A 100 mL; single necked, round bottom flask fitted with an ozone bubbler was charged with a solution of alkenyl hydroxy cyclopentabenzofuran (6) (1.8 g, 5.69 mmol) in anhydrous methanol (30 mL) and anhydrous dichloromethane (10 mL), and this was cooled to −78° C. Then ozone gas was bubbled through the solution for 15 minutes using a Wedeco GSO 10 series ozone generator. The progress of the reaction was monitored by TLC, which indicated complete conversion of starting material. At this stage temperature of the reaction mixture was increased to −20° C. and flushed with argon gas for 5 minutes.

To the ozonide intermediate was added sodium borohydride (0.43g, 11.38 mmol) at −20° C. and stirred under argon for 2 h while allowing the reaction mixture to attain ambient temperature. The progress of the reaction was monitored by TLC. After completion of the reaction, it was quenched with glacial acetic acid (3 mL) and organic volatiles were evaporated in vacuo. The residue was partitioned between ethyl acetate (2×30 mL) and water (30 mL). The combined organic layers were washed with brine (30 mL), dried over sodium sulfate and evaporated in vacuo to obtain crude product. This was loaded on to the silica packed column for purification. The fractions containing the desired compound (checked by TLC) were combined and evaporated in vacuo to yield Beraprost ester diol (1.5 g, 86.2%). The compound was characterized by $^1$H NMR and chiral HPLC.

Example 4

Synthesis of
2-Bromophenol-6-carbomethoxypropane (8)

(A) Synthesis of Benzolactone (3)

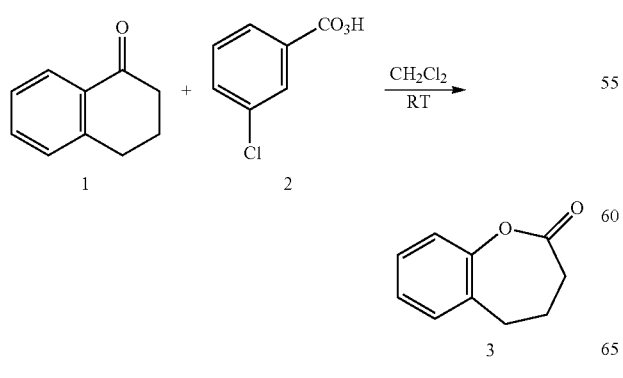

To a solution of α-tetralone (1) (30.69 g, 209.93 mmol) in dichloromethane (500 mL) was added 3-chloroperbenzoic acid (2) (~77%, 57.5 g, 252.15mmol) under argon at room temperature. The reaction mixture was stirred at room temperature. The reaction was monitored by tlc (EtOAc/Hexane, 1:4). After 93 h, the reaction mixture was filtered to remove 3-chlorobenzoic acid (solid) and the solid was washed with dichloromethane. The dichloromethane filtrate was washed with 10% aqueous solution of sodium bisulfite (1×100 mL), 10% aqueous solution of sodium carbonate (3×100 mL), brine (1×50 mL), dried (Na$_2$SO$_4$), filtered and concentrated in vacuo to give crude benzolactone (3) as a pale yellow liquid (3 3. 80 g). The crude compound contained some starting material (~10% by 1 H NMR and tlc) and was used in the next step without further purification.

(B) Synthesis of Methyl
4-(2-hydroxyphenyl)butanoate (5)

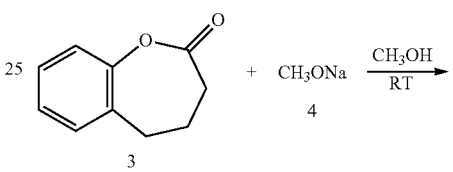

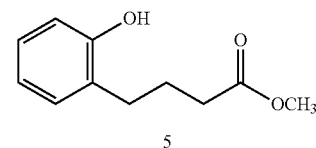

To a solution of crude benzolactone (3) (33.80 g, 208.41mmol) in methanol (350 mL) was added solid sodium methoxide (4) (13.51 g, 250.09mmo1) in small portions at room temperature under argon. The reaction mixture was stirred for 1 h and checked by tlc (EtOAc/Hexane, 1:4). The mixture was acidified with 3N hydrochloric acid (100 mL) to pH 1-2. The mixture was evaporated in vacuo to remove methanol and the aqueous residue was diluted with water (100 mL). The mixture was extracted with ethyl acetate (3×75 mL). The combined ethyl acetate extracts were washed with water (2×100 mL), saturated sodium bicarbonate solution (2×30 mL), brine (1×25 mL), dried (Na$_2$SO$_4$), filtered and concentrated in vacuo to give crude methyl 4-(2-hydroxyphenyl)butanoate (5) as a light-brown liquid (36.34 g). The crude product was chromatographed on silica gel (392.4 g) using ethyl acetate in hexanes (2-15%) to give pure compound as a light amber liquid (30.6 g, 75.1% in two steps and characterized by spectral data (IR, 1HNMR, 13C NMR, MS).

(C)Regioselective Bromination of 4-(2-:hydroxyphenyl)butanoate (5) with N-Bromosuccinimide (NBS) and Bromine in Various Solvents

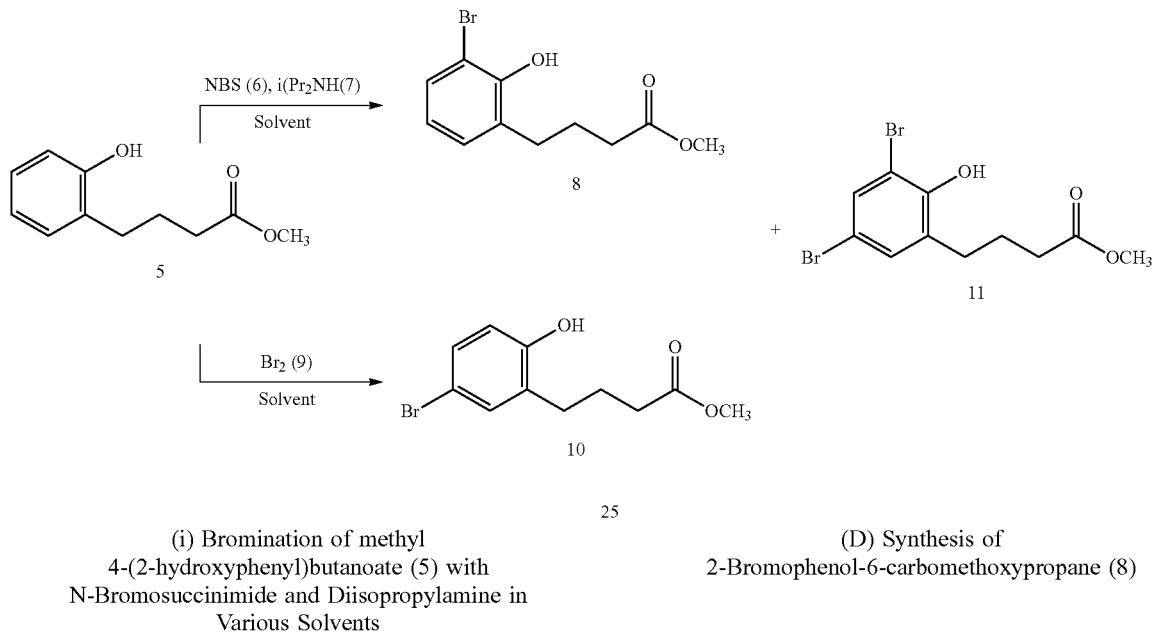

(i) Bromination of methyl 4-(2-hydroxyphenyl)butanoate (5) with N-Bromosuccinimide and Diisopropylamine in Various Solvents To a solution of methyl 4-(2-hydroxyphenyl)butanoate (5) (0.50-2.5 mmol, 1.0 eq) in solvent (3.0-10.0) mL) was added diisopropylamine (0.50-2.5 mmol, 1.0 eq or less, and some cases without diisopropylamine). To the clear solution was added N-bromosuccinimide (0.50-2.5 mmol, 0.90-1.0 eq) in one portion under argon at 0° C., room temperature or −78° C.). The reaction mixture was stirred at appropriated temperature for 30 min to 3 h and the reaction was monitored by tlc (EtOAc/Hexane, 1:4). The reaction mixture was evaporated directly without aqueous work up in vacuo to give crude product, or aqueous worked up to give crude product. The $^1$H NMR and HPLC of the crude were taken and results are tabulated (see Table 1).

(ii) Bromination 4-(2-hydroxyphenyl)butanoate (5) with Bromine in Various Solvents To a solution of methyl 4-(2-hydroxyphenyl)butanoate (5) (0.25-3.7 mmol, 1.0 eq) in solvent $CH_2Cl_2$, $CCl_4$ or $Et_2O$ (1.0-5.0) mL) was added a solution of bromine (0.25-7.4 mmol) in $CH_2Cl_2$, $CCl_4$ or $Et_2O$ at 0° C. to 5° C. (ice/water bath) under argon. The reaction mixture (reddish-brown to pale yellow color) mixture was stirred for 30 min and checked tlc (EtOAc/Hexane, 1:4). The reaction mixture, without aqueous worked-up, was evaporated invacuo to give crude bro mo compound as a pale yellow viscous liquid. The 1 H NMR and HPLC of the crude products were taken and results are tabulated (see Table 2).

(D) Synthesis of 2-Bromophenol-6-carbomethoxypropane (8)

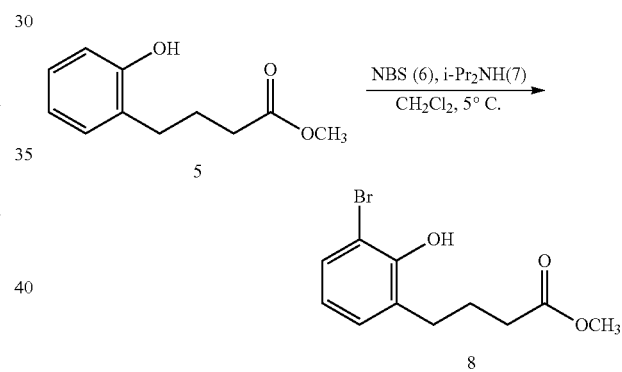

To a solution of methyl 4-(2-hydroxyphenyl)butanoate (5) (30.0 g, 154.46 mmol) in anhydrous dichloromethane (750 mL) was added diisopropylamine (7) (15.63 g, 154.46 mmol) at room temperature under argon. The clear solution was cooled to 5° C. (internal reaction temperature) (ice/water bath) and then added N-bromosuccinimide (NBS) (6) (27.49 g, 154.45 mmol) in one portion (slightly exothermic!, the internal temperature was raised to 10° C.). The bright yellow reaction mixture was stirred at 5° C. for 2 h and checked tlc (EtOAc/Hexane, 1:4). The reaction mixture became almost colorless or slightly pale yellow). The mixture was quenched with water (200 mL). The organic layer (dichloromethane) was separated and evaporated in vacuo toremove dichloromethane. The residue was dissolved in MTBE (300 mL) and then washed with water (2×150 mL), 2N hydrochloric acid (1×25 mL), water (2×150 mL), brine (1×25 mL), dried ($Na_2SO_4$), filtered and concentrated in vacuo to give 2-bromophenol-6-carbomethoxypropane (8) as a pale yellow viscous liquid (41.50 g). The HPLC of the crude product showed 2-bromo, 4-bromo, 2,4-dibromo compounds and starting material in 88.7, 0.1 , 6.9 and 3.7% respectively. The crystallization of the crude product from cyclopentane gave off-white crystals with purity of 94.7% 2-bromo compound. Further crystallization gave 97.1% of pure 2-bromo compound (8) as white crystals, mp 31-32° C. (25.91 g, 61.4% yield) and characterized by spectral data (IR, $^1$H NMR, $^{13}$CNMR, MS).

(E) Synthesis of
2,4-Dibromophenol-6-carbomethoxypropane (11)

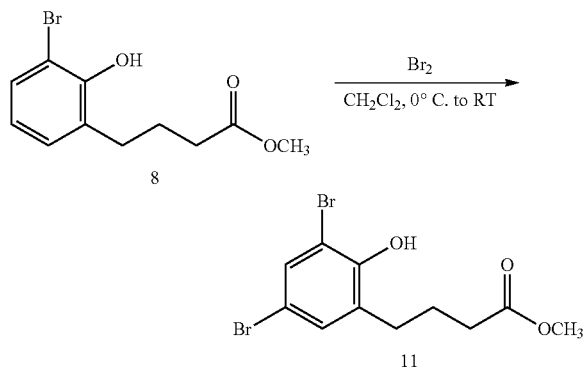

To a solution of 2-bromophenol-6-carbomethoxypropane (8) (4.68 g, 17.13 mmol) in dichloromethane (50 mL) was added a solution of bromine (4.1 g, 25.65 mmol) in dichloromethane (10 mL) at 0° C. to 5° C. (ice/water bath) under argon. The reaction mixture (light bromine color) was stirred at this temperature for 2 h and at room temperature overnight. After 16 h, the reaction mixture was checked by tlc (EtOAc/Hexane, 1:4). The reaction mixture was treated with a 5% solution of sodium thiosulfate (50 mL) and then separated the layers. The dichloromethane layer was washed with water (1×50 mL), saturated sodium bicarbonate (1×30 mL), water (1×50 mL), brine (1×15 mL), dried (Na$_2$SO$_4$), filtered and concentrated in vacuo to give light yellow viscous liquid (5,78 g). The crude product was recrystallized from hexane and ethyl acetate at −18° C. to afford a pure 2,4-dibromophenol-6-carbomethoxypropane (11) as an off-white solid (2.84 g, 47.1%), mp 55-57° C., purity 93 .7% by HPLC and characterized by spectral data (IR, $^1$H NMR and $^{13}$CNMR).

Example 5

Large Scale Synthesis of
2-Bromophenol-6-carbomethoxypropane (8)

The 2-bromopheno1-6-carbomethoxypropane (8) was synthesized from a-tetralone (1) in three steps.

(A) Synthesis of Benzolactone (3)

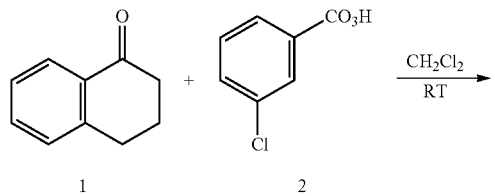

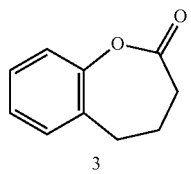

To a solution of α-tetralone (1) (102.58 g, 701.69 mmol) in dichloromethane (1700 mL) was added 3-chloroperbenzoic acid (2) (~77%, 192.0 g, 842.06 mmol) under argon at room temperature (slightly endothermic reaction was observed during the addition of 3-chloroperbenzoic acid). The reaction mixture was stin-ed at room temperature and monitored by tlc (EtOAc/Hexane, 1:4). After 140 h, there was a very little starting material left. The reaction mixture was filtered to remove 3-chlorobenzoic acid (solid) and washed the solid with dichloromethane. The dichloromethane filtrate was washed with 10% aqueous solution of sodium bisulfite (1×300 mL), 10% aqueous solution of sodium carbonate (1×1000 mL), brine (1×50 mL), dried (Na$_2$SO$_4$), filtered and concentrated in vacuo to give crude benzolactone (3) as a pale yellow liquid (122.6 g). The crude compound contained some starting material (~5% by $^1$H NMR and tlc) was used in the next step without further purification.

(B) Synthesis of Methyl
4-(2-hydroxyphenyl)butanoate (5)

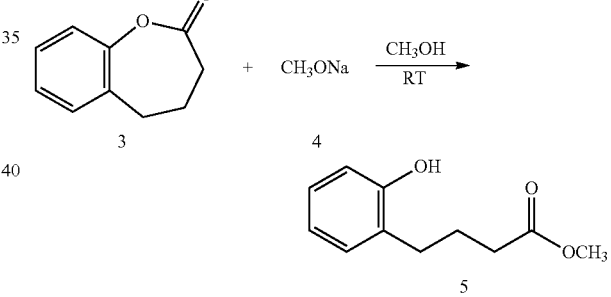

To a solution of crude benzolactone (3) (122.6 g, crude calculated as 113.80 g, 701.69 mmol) in methanol (1000 mL) was added solid sodium methoxide (4) (45.5 g, 842.28 mmol) in small portions (slightly exothermic!) at room temperature under argon. The reaction mixture was stirred at room temperature for 1 hand checked by tlc (EtOAc/ Hexane, 1:4). The mixture was acidified with 3N hydrochloric acid (300 mL) to pH 1-2. The mixture was evaporated in vacuo to remove methanol and the aqueous residue was diluted with water (300 mL). The mixture was extracted with ethyl acetate (3×150 mL). The combined ethyl acetate extracts were washed with water (2×100 mL), saturated sodium bicarbonate solution (2×40 mL), brine (1×30 mL), dried (Na$_2$SO$_4$), filtered and concentrated in vacuo to give crude methyl 4-(2-hydroxyphenyl)butanoate (5) as a light-brown liquid (126.11 g). The filtration type chromatography of the crude product on silica gel (398.11 g) using ethyl acetate in hexanes (2-15%) gave methyl 4-(2-hydroxyphenyl)butanoate (5) as a light amber liquid (119.3 g, 87.3% in two steps), purity 95.44% by HPLC and characterized by $^1$HNMR spectrum.

(C) Synthesis of
2-Bromophenol-6-carbomethoxypropane (8)

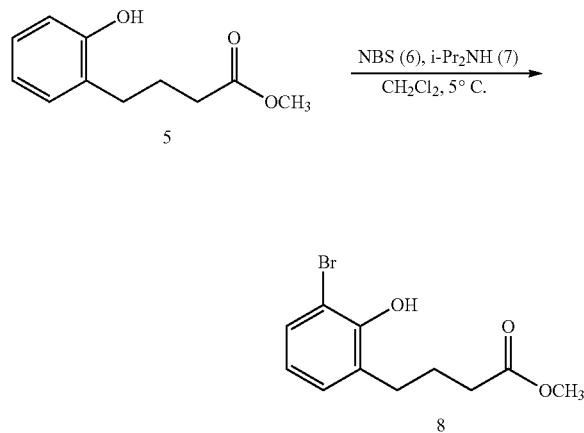

To a solution of methyl 4-(2-hydroxyphenyl)butanoate (5) (118.2 g, 608.59 mmol) in anhydrous dichloromethane (2955 mL) was added diisopropylamine (7) (61.58 g, 608.56 mmol) at room temperature under argon. The clear solution was cooled to 5° C. (internal reaction temperature) (dry ice/acetone, controlled bath temperature) and then added N-bromosuccinimide (NBS) (6) (108.32 g, 608.57 mmol) in one portion (slightly exothermic, the internal temperature was raised to 10° C.). The bright yellow reaction mixture was stirred at 5 to 10° C. for 2 h and checked by tlc (EtOAc/Hexane, 1:4). The reaction mixture became almost colorless or slightly pale yellow. The mixture was quenched with water (1000 mL). The organic layer (dichloromethane) was separated and evaporated in vacuo to remove dichloromethane. The residue (obtained after dichloromethane evaporation) containing organic compound was dissolved in MTBE (750 mL) and washed with water (2×150 mL), 2N hydrochloric acid (1×30 mL), water (2×150 mL), brine (1×25 mL), dried ($Na_2SO_4$), filtered and concentrated in vacuo to give 2-bromophenol-6-carbomethoxypropane (8) as a pale yellow viscous liquid (162.8 g). The crude product contained 90% of 2-bromo and 10% of 2,4-dibromo compounds (by HPLC). The recrystallization of the crude product from cyclopentane (1600 mL) and ethyl acetate (16 mL) at −40° C. gave off-white crystals (81.68%) with purity of 97.4% of 2-bromo compound and 1.94% of 2,4-dibromo compound. The mother liquor residue (85.4 g) was recrystallized three times with cyclopentane and ethyl acetate at −40° C. to afford off-white crystals (26.89 g) with purity of 96.6% of 2-bromo compound and 1.99% of 2,4-dibromo compound. The total combined weight of 2-bromophenol-6-carbomethoxypropane (8) was 108.6 g (56.6% in three steps). The compound was characterized by $^1$HNMR spectrum.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While certain embodiments have been illustrated and described, it should be understood that changes and modifications can be made therein in accordance with ordinary skill in the art without departing from the technology in its broader aspects as defined in the following claims.

What is claimed is:

1. A method of preparing a beraprost ester diol compound represented by the structural Formula (IX):

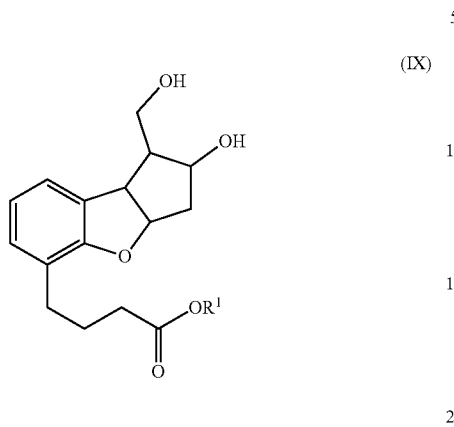

(IX)

comprising:

(i) reacting a substituted halophenol with 6-oxabicyclo[3.1.0]hex-2-ene in presence of a palladium catalyst to form an ether compound represented by structural Formula (III):

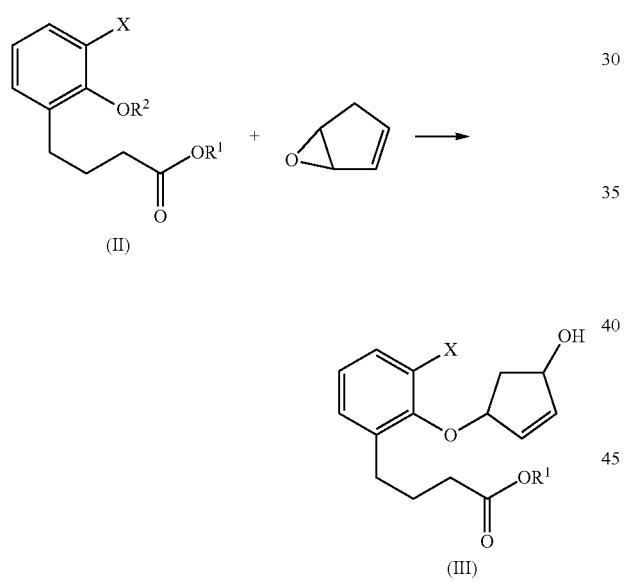

(ii) allylating the compound of Formula (III) with an allylating reagent in presence of a radical initiator to form the allylation product (VA)

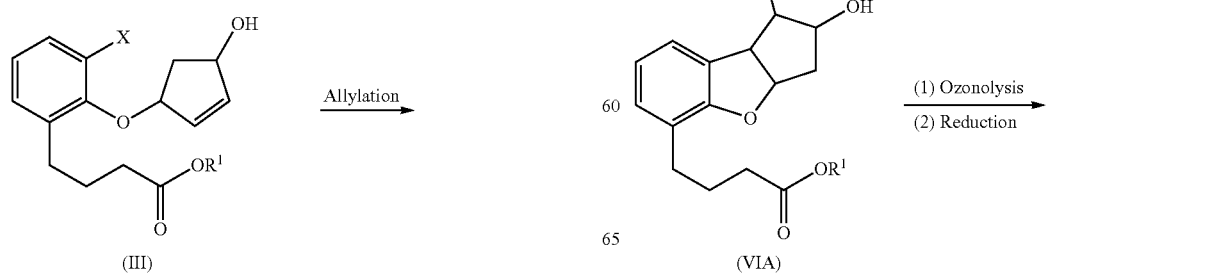

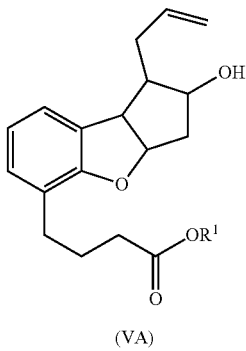

(VA)

(iii) subjecting the terminal alkene compound of Formula (VA) to terminal olefin isomerization to form a compound of Formula (VIA); and

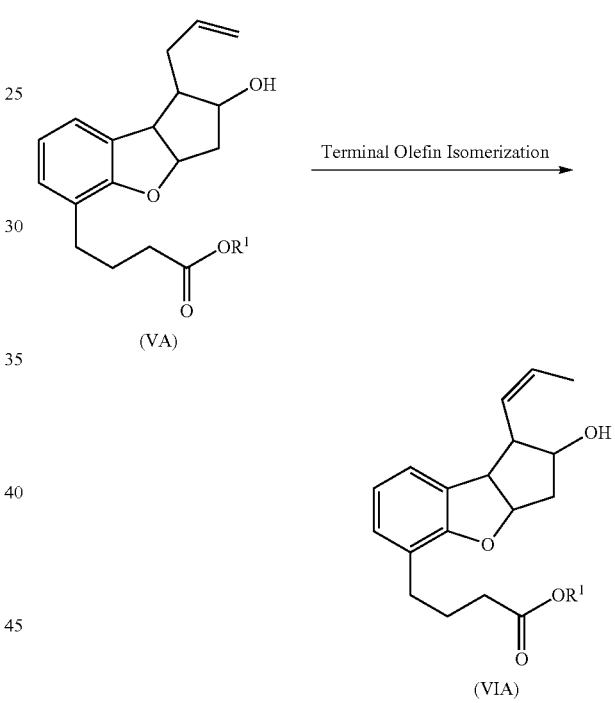

(iv) ozonolyzing and reducing the compound of Formula (VIA) to provide a diol of Formula (IX)

-continued

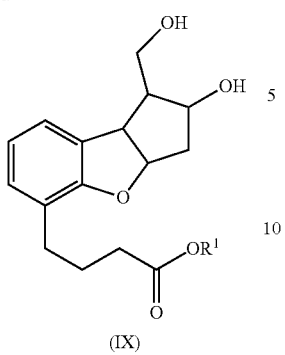

wherein:

X is F, Cl, Br or I;

$R^1$ is an alkyl, cycloalkyl or TBDMS; and $R^2$ is independently H or an alcohol protecting group.

2. The method of claim 1, further comprising converting the beraprost ester diol compound of Formula (IX) to a compound represented by the structural Formula (I):

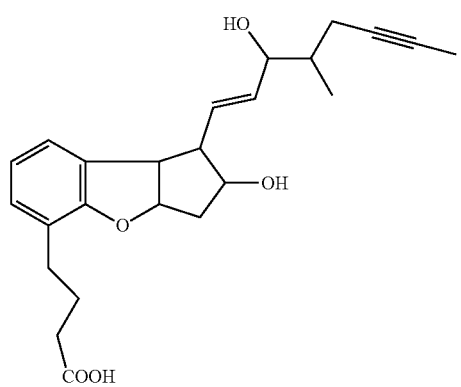

or a salt thereof; comprising:

(v) converting the diol of Formula (IX) to a protected aldehyde of Formula (VIIIA); and

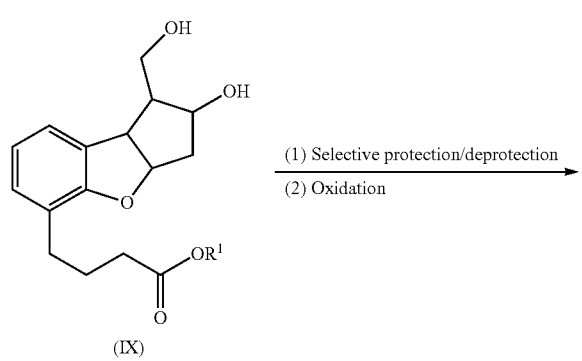

-continued (vi) reacting the protected aldehyde of Formula (VIIIA) with a phosphonate of Formula (X) to obtain a compound of Formula (I)

wherein:

$R^1$ is an alkyl, cycloalkyl or TBDMS;

$R^3$ is a straight or branched alkyl group having 1-4 carbon atoms; and $R^6$ is an alcohol protecting group.

3. The method of claim 1, wherein $R^1$ is methyl or ethyl.

4. The method of claim 1, wherein the palladium catalyst is $PdCl_2(PPh_3)_2$.

5. The method of claim 1, wherein the terminal olefin isomerization reaction is carried out in the presence of a transition metal catalyst.

6. The method of claim 1, wherein the palladium catalyst is $PdCl_2(PPh_3)_2$, $Pd(Ph_3)_4$, and $PdCl_2(dppf)_2$, $Pd(OAc)_2$, $Pd_2(dba)_3$.

7. The method of claim 1 wherein the allylating reagent is allyltributyltin (allyl-BusSn), allylmagnesium bromide (allyl-MgBr); allyl halide; allyltrihalosilane; allyl carboxylate; allyl carbonate; diallyl carboxylate; diallyl sulfate; metalallyl reagent or a combination thereof.

8. The method of claim 1, wherein the allylating reagent is allyltributyltin.

9. The method of claim 1, wherein the allylating is Keck radical allylation.

10. The method of claim 1, wherein the radical initiator is azobis-iso-butyronitrile, di-tert-butyl, dilauroyl, or dibenzoyl peroxide.

11. The method of claim 1, wherein the allylating reagent is allyltributyltin and the radical initiator is azobis iso butyronitrile.

12. The method of claim 1, wherein X is Br or I, $R^1$ is $C_1$-$C_4$ alkyl and $R^2$ is H.

13. The method of claim 1, wherein X is Br, $R^1$ is methyl and $R^2$ is H.

\* \* \* \* \*